(12) United States Patent
Cheng et al.

(10) Patent No.: US 7,232,665 B2
(45) Date of Patent: Jun. 19, 2007

(54) MUTATIONS AFFECTING CAROTENOID PRODUCTION

(75) Inventors: Qiong Cheng, Wilmington, DE (US); Pierre E. Rouviere, Wilmington, DE (US); Luan Tao, Claymont, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 300 days.

(21) Appl. No.: 10/735,008

(22) Filed: Dec. 12, 2003

(65) Prior Publication Data

US 2004/0146966 A1   Jul. 29, 2004

Related U.S. Application Data

(60) Provisional application No. 60/435,612, filed on Dec. 19, 2002.

(51) Int. Cl.
*C12P 23/00* (2006.01)
*C12N 1/20* (2006.01)

(52) U.S. Cl. ............... 435/67; 435/183; 435/252.3; 435/320.1; 536/23.2

(58) Field of Classification Search ............ 435/67, 435/183, 252.2, 252.3, 252.31, 254.2; 536/23.2
See application file for complete search history.

(56) References Cited

U.S. PATENT DOCUMENTS

| | | | |
|---|---|---|---|
| 5,429,939 | A | 7/1995 | Misawa et al. |
| 5,530,188 | A | 6/1996 | Ausich et al. |
| 5,530,189 | A | 6/1996 | Ausich et al. |
| 5,545,816 | A | 8/1996 | Ausich et al. |
| 5,656,472 | A | 8/1997 | Ausich et al. |
| 2002/0115161 | A1 | 8/2002 | Farwick et al. |

OTHER PUBLICATIONS

Armstrong, In Comprehensive Natural Products Chemistry, Elsevier Press, vol. 2, pp. 321-352, 1999.
Armstrong et al., Eubacteria Show Their True Colors: Genetics of Carotenoid Pigment Biosynthesis from Microbes to Plants, J. Bact., vol. 176, 4795-4802, 1994.
Armstrong, Genetics of Eubacterial Carotenoid Biosynthesis: A Colorful Tale, Annu. Rev. Microbiol. vol. 51, pp. 629-659, 1997.
Kim et al., Metabolic Engineering of the Nonmevalonate Isopentenyl Diphosphate Synthesis Pathway in *Escherichia coli* Enhances Lyocpene Production, Biotech. Bioeng., vol. 72: pp. 408-415, 2001.
Mathews et al., Metabolic engineering of carotenoid accumulation in *Escherichia coli* by modulation of the isoprenoid precoursor pool with expression of deoxyxylulose phosphate synthase, Appl. Microbiol. Biotechnol., 53: 396-400, 2000.
Harker et al., Expression of prokaryotic 1-deoxy-D-xylulose-5-phosphatases in *Escherichia coli* increases carotenoid and ubiquinone biosynthesis, FEBS Letter., vol. 448: 115-119, 1999.
Misawa et al., Metabolic engineering for the production of carotenoids in non-carotenogenic bacteria and yeasts, vol. 59: pp. 169-181, 1998.
Kijiwara et al., Expression of an exogenous isopentenyl diphosphate isomerase gene enhances isoprenoid biosynthesis in *Escherichia coli*, Biochem. J., vol. 324: pp. 421-426, 1997.
Wang et al., Engineered Isoprenoid Pathway Enhances Astaxanthin Production in *Escherichia coli*, Biotech. Bioeng., vol. 62: pp. 235-241, 1999.
Wang et al., Directed Evolution of Metabolically Engineered *Escherichia coli* for Carotenoid Production, Biotechnol. Prog. vol. 16, 922-926, 2000.
Lagarde et al., Increased Production of Zeaxanthin and Other Pigments by Application of Genetic Engineering Techniques to Synechocystis sp. Strain PCC 6803, Appl. Env. Microbiol., vol. 66: pp. 64-72, 2000.
Szkopinska et al., Polyprenol formation in the yeast *Saccharomyces cerevisiae*: effect of farnesyl diphosphate synthase overexpression, J. Lipid Res., vol. 38, pp. 962-968, 1997.
Shimada et al.,Increased Carotenoid Production by the Food Yeast *Candids utilis* through Metabolic Engineering of the Isoprenoid Pathway, Appl. Env. Microb., vol. 64: pp. 2676-2680, 1998.
Yamano et al., Metabolic Engineering for Production of β-Carotene and Lycopene in *Saccharomyces cerevisiae*, Biosci. Biotech. Biochem., vol. 58, pp. 1112-1114, 1994.
Sandman, G., Genetic manipulation of carotenoids biosynthesis: strategies, problems and achievements, Trends in Plant Science, vol. 6: pp. 14-17, 2001.

*Primary Examiner*—Tekchand Saidha

(57) ABSTRACT

Mutations in genes having no direct relationship to the carotenoid biosynthetic pathway have been found to increase carbon flux through that pathway. Complete disruption in the deaD, mreC, and yfhE genes were effective. Additionally where genes of the lower carotenoid pathway reside on a plasmid having either a p15A or pMB1 replicon, mutations in the thrS, rspA, rpoC, yjeR, and rhoL were found effective.

9 Claims, 6 Drawing Sheets

SEQUENCE LISTING

<160> NUMBER OF SEQ ID NOS: 43

<210> SEQ ID NO 1
<211> LENGTH: 912
<212> TYPE: DNA
<213> ORGANISM: Pantoea stewartii
<220> FEATURE:
<221> NAME/KEY: misc_feature
<222> LOCATION: (1)..(3)
<223> OTHER INFORMATION: Alternative start code usage of TTG instead of ATG.

<400> SEQUENCE: 1

```
ttgacggtct gcgcaaaaaa acacgttcac cttactggca tttcggctga gcagttgctg     60
gctgatatcg atagccgcct tgatcagtta ctgccggttc agggtgagcg ggattgtgtg    120
ggtgccgcga tgcgtgaagg cacgctggca ccgggcaaac gtattcgtcc gatgctgctg    180
ttattaacag cgcgcgatct tggctgtgcg atcagtcacg ggggattact ggatttagcc    240
tgcgcggttg aaatggtgca tgctgcctcg ctgattctgg atgatatgcc ctgcatggac    300
gatgcgcaga tgcgtcgggg gcgtcccacc attcacacgc agtacggtga acatgtggcg    360
attctggcgg cggtcgcttt actcagcaaa gcgtttgggg tgattgccga ggctgaaggt    420
ctgacgccga tagccaaaac tcgcgcggtg tcggagctgt ccactgcgat tggcatgcag    480
ggtctggttc agggccagtt taaggacctc tcggaaggcg ataaaccccg cagcgccgat    540
gccatactgc taaccaatca gtttaaaacc agcacgctgt tttgcgcgtc aacgcaaatg    600
gcgtccattg cggccaacgc gtcctgcgaa gcgcgtgaga acctgcatcg tttctcgctc    660
gatctcggcc aggcctttca gttgcttgac gatcttaccg atggcatgac cgataccggc    720
aaagacatca atcaggatgc aggtaaatca acgctggtca atttattagg ctcaggcgcg    780
gtcgaagaac gcctgcgaca gcatttgcgc ctggccagtg aacacctttc cgcggcatgc    840
caaaacggcc attccaccac ccaactttt attcaggcct ggtttgacaa aaaactcgct    900
gccgtcagtt aa                                                         912
```

<210> SEQ ID NO 2
<211> LENGTH: 303
<212> TYPE: PRT
<213> ORGANISM: Pantoea stewartii

<400> SEQUENCE: 2

```
Met Thr Val Cys Ala Lys Lys His Val His Leu Thr Gly Ile Ser Ala
1               5                   10                  15

Glu Gln Leu Leu Ala Asp Ile Asp Ser Arg Leu Asp Gln Leu Leu Pro
            20                  25                  30

Val Gln Gly Glu Arg Asp Cys Val Gly Ala Ala Met Arg Glu Gly Thr
        35                  40                  45

Leu Ala Pro Gly Lys Arg Ile Arg Pro Met Leu Leu Leu Thr Ala
    50                  55                  60

Arg Asp Leu Gly Cys Ala Ile Ser His Gly Gly Leu Leu Asp Leu Ala
65                  70                  75                  80

Cys Ala Val Glu Met Val His Ala Ala Ser Leu Ile Leu Asp Asp Met
                85                  90                  95

Pro Cys Met Asp Asp Ala Gln Met Arg Arg Gly Arg Pro Thr Ile His
            100                 105                 110
```

```
Thr Gln Tyr Gly Glu His Val Ala Ile Leu Ala Ala Val Ala Leu Leu
            115                 120                 125

Ser Lys Ala Phe Gly Val Ile Ala Glu Ala Glu Gly Leu Thr Pro Ile
        130                 135                 140

Ala Lys Thr Arg Ala Val Ser Glu Leu Ser Thr Ala Ile Gly Met Gln
145                 150                 155                 160

Gly Leu Val Gln Gly Gln Phe Lys Asp Leu Ser Glu Gly Asp Lys Pro
                165                 170                 175

Arg Ser Ala Asp Ala Ile Leu Leu Thr Asn Gln Phe Lys Thr Ser Thr
                180                 185                 190

Leu Phe Cys Ala Ser Thr Gln Met Ala Ser Ile Ala Ala Asn Ala Ser
        195                 200                 205

Cys Glu Ala Arg Glu Asn Leu His Arg Phe Ser Leu Asp Leu Gly Gln
    210                 215                 220

Ala Phe Gln Leu Leu Asp Asp Leu Thr Asp Gly Met Thr Asp Thr Gly
225                 230                 235                 240

Lys Asp Ile Asn Gln Asp Ala Gly Lys Ser Thr Leu Val Asn Leu Leu
                245                 250                 255

Gly Ser Gly Ala Val Glu Arg Leu Arg Gln His Leu Arg Leu Ala
                260                 265                 270

Ser Glu His Leu Ser Ala Ala Cys Gln Asn Gly His Ser Thr Thr Gln
        275                 280                 285

Leu Phe Ile Gln Ala Trp Phe Asp Lys Lys Leu Ala Ala Val Ser
        290                 295                 300

<210> SEQ ID NO 3
<211> LENGTH: 1296
<212> TYPE: DNA
<213> ORGANISM: Pantoea stewartii
<220> FEATURE:
<221> NAME/KEY: CDS
<222> LOCATION: (1)..(1296)

<400> SEQUENCE: 3 atg agc cat ttt gcg gtg atc gca ccg ccc ttt ttc agc cat gtt cgc     48
Met Ser His Phe Ala Val Ile Ala Pro Pro Phe Phe Ser His Val Arg
1               5                   10                  15 gct ctg caa aac ctt gct cag gaa tta gtg gcc cgc ggt cat cgt gtt     96
Ala Leu Gln Asn Leu Ala Gln Glu Leu Val Ala Arg Gly His Arg Val
            20                  25                  30 acg ttt ttt cag caa cat gac tgc aaa gcg ctg gta acg ggc agc gat    144
Thr Phe Phe Gln Gln His Asp Cys Lys Ala Leu Val Thr Gly Ser Asp
        35                  40                  45 atc gga ttc cag acc gtc gga ctg caa acg cat cct ccc ggt tcc tta    192
Ile Gly Phe Gln Thr Val Gly Leu Gln Thr His Pro Pro Gly Ser Leu
    50                  55                  60 tcg cac ctg ctg cac ctg gcc gcg cac cca ctc gga ccc tcg atg tta    240
Ser His Leu Leu His Leu Ala Ala His Pro Leu Gly Pro Ser Met Leu
65                  70                  75                  80 cga ctg atc aat gaa atg gca cgt acc agc gat atg ctt tgc cgg gaa    288
Arg Leu Ile Asn Glu Met Ala Arg Thr Ser Asp Met Leu Cys Arg Glu
                85                  90                  95 ctg ccc gcc gct ttt cat gcg ttg cag ata gag ggc gtg atc gtt gat    336
Leu Pro Ala Ala Phe His Ala Leu Gln Ile Glu Gly Val Ile Val Asp
            100                 105                 110 caa atg gag ccg gca ggt gca gta gtc gca gaa gcg tca ggt ctg ccg    384
Gln Met Glu Pro Ala Gly Ala Val Val Ala Glu Ala Ser Gly Leu Pro
        115                 120                 125
```

|  |  |
|---|---|
| ttt gtt tcg gtg gcc tgc gcg ctg ccg ctc aac cgc gaa ccg ggt ttg<br>Phe Val Ser Val Ala Cys Ala Leu Pro Leu Asn Arg Glu Pro Gly Leu<br>130                        135                      140 | 432 |
| cct ctg gcg gtg atg cct ttc gag tac ggc acc agc gat gcg gct cgg<br>Pro Leu Ala Val Met Pro Phe Glu Tyr Gly Thr Ser Asp Ala Ala Arg<br>145                      150                      155                      160 | 480 |
| gaa cgc tat acc acc agc gaa aaa att tat gac tgg ctg atg cga cgt<br>Glu Arg Tyr Thr Thr Ser Glu Lys Ile Tyr Asp Trp Leu Met Arg Arg<br>                165                      170                      175 | 528 |
| cac gat cgt gtg atc gcg cat cat gca tgc aga atg ggt tta gcc ccg<br>His Asp Arg Val Ile Ala His His Ala Cys Arg Met Gly Leu Ala Pro<br>            180                      185                      190 | 576 |
| cgt gaa aaa ctg cat cat tgt ttt tct cca ctg gca caa atc agc cag<br>Arg Glu Lys Leu His His Cys Phe Ser Pro Leu Ala Gln Ile Ser Gln<br>                195                      200                      205 | 624 |
| ttg atc ccc gaa ctg gat ttt ccc cgc aaa gcg ctg cca gac tgc ttt<br>Leu Ile Pro Glu Leu Asp Phe Pro Arg Lys Ala Leu Pro Asp Cys Phe<br>210                        215                      220 | 672 |
| cat gcg gtt gga ccg tta cgg caa ccc cag ggg acg ccg ggg tca tca<br>His Ala Val Gly Pro Leu Arg Gln Pro Gln Gly Thr Pro Gly Ser Ser<br>225                        230                      235                      240 | 720 |
| act tct tat ttt ccg tcc ccg gac aaa ccc cgt att ttt gcc tcg ctg<br>Thr Ser Tyr Phe Pro Ser Pro Asp Lys Pro Arg Ile Phe Ala Ser Leu<br>                245                      250                      255 | 768 |
| ggc acc ctg cag gga cat cgt tat ggc ctg ttc agg acc atc gcc aaa<br>Gly Thr Leu Gln Gly His Arg Tyr Gly Leu Phe Arg Thr Ile Ala Lys<br>            260                      265                      270 | 816 |
| gcc tgc gaa gag gtg gat gcg cag tta ctg ttg gca cac tgt ggc ggc<br>Ala Cys Glu Glu Val Asp Ala Gln Leu Leu Leu Ala His Cys Gly Gly<br>                275                      280                      285 | 864 |
| ctc tca gcc acg cag gca ggt gaa ctg gcc cgg ggc ggg gac att cag<br>Leu Ser Ala Thr Gln Ala Gly Glu Leu Ala Arg Gly Gly Asp Ile Gln<br>290                        295                      300 | 912 |
| gtt gtg gat ttt gcc gat caa tcc gca gca ctt tca cag gca cag ttg<br>Val Val Asp Phe Ala Asp Gln Ser Ala Ala Leu Ser Gln Ala Gln Leu<br>305                        310                      315                      320 | 960 |
| aca atc aca cat ggt ggg atg aat acg gta ctg gac gct att gct tcc<br>Thr Ile Thr His Gly Gly Met Asn Thr Val Leu Asp Ala Ile Ala Ser<br>                325                      330                      335 | 1008 |
| cgc aca ccg cta ctg gcg ctg ccg ctg gca ttt gat caa cct ggc gtg<br>Arg Thr Pro Leu Leu Ala Leu Pro Leu Ala Phe Asp Gln Pro Gly Val<br>            340                      345                      350 | 1056 |
| gca tca cga att gtt tat cat ggc atc ggc aag cgt gcg tct cgg ttt<br>Ala Ser Arg Ile Val Tyr His Gly Ile Gly Lys Arg Ala Ser Arg Phe<br>                355                      360                      365 | 1104 |
| act acc agc cat gcg ctg gcg cgg cag att cga tcg ctg ctg act aac<br>Thr Thr Ser His Ala Leu Ala Arg Gln Ile Arg Ser Leu Leu Thr Asn<br>370                        375                      380 | 1152 |
| acc gat tac ccg cag cgt atg aca aaa att cag gcc gca ttg cgt ctg<br>Thr Asp Tyr Pro Gln Arg Met Thr Lys Ile Gln Ala Ala Leu Arg Leu<br>385                        390                      395                      400 | 1200 |
| gca ggc ggc aca cca gcc gcc gcc gat att gtt gaa cag gcg atg cgg<br>Ala Gly Gly Thr Pro Ala Ala Ala Asp Ile Val Glu Gln Ala Met Arg<br>                405                      410                      415 | 1248 |
| acc tgt cag cca gta ctc agt ggg cag gat tat gca acc gca cta tga<br>Thr Cys Gln Pro Val Leu Ser Gly Gln Asp Tyr Ala Thr Ala Leu<br>            420                      425                      430 | 1296 |

<210> SEQ ID NO 4

-continued

<211> LENGTH: 431
<212> TYPE: PRT
<213> ORGANISM: Pantoea stewartii

<400> SEQUENCE: 4

```
Met Ser His Phe Ala Val Ile Ala Pro Pro Phe Ser His Val Arg
1               5                   10                  15

Ala Leu Gln Asn Leu Ala Gln Glu Leu Val Ala Arg Gly His Arg Val
            20                  25                  30

Thr Phe Phe Gln Gln His Asp Cys Lys Ala Leu Val Thr Gly Ser Asp
        35                  40                  45

Ile Gly Phe Gln Thr Val Gly Leu Gln Thr His Pro Pro Gly Ser Leu
    50                  55                  60

Ser His Leu Leu His Leu Ala Ala His Pro Leu Gly Pro Ser Met Leu
65                  70                  75                  80

Arg Leu Ile Asn Glu Met Ala Arg Thr Ser Asp Met Leu Cys Arg Glu
                85                  90                  95

Leu Pro Ala Ala Phe His Ala Leu Gln Ile Glu Gly Val Ile Val Asp
            100                 105                 110

Gln Met Glu Pro Ala Gly Ala Val Val Ala Glu Ala Ser Gly Leu Pro
        115                 120                 125

Phe Val Ser Val Ala Cys Ala Leu Pro Leu Asn Arg Glu Pro Gly Leu
    130                 135                 140

Pro Leu Ala Val Met Pro Phe Glu Tyr Gly Thr Ser Asp Ala Ala Arg
145                 150                 155                 160

Glu Arg Tyr Thr Thr Ser Glu Lys Ile Tyr Asp Trp Leu Met Arg Arg
                165                 170                 175

His Asp Arg Val Ile Ala His His Ala Cys Arg Met Gly Leu Ala Pro
            180                 185                 190

Arg Glu Lys Leu His His Cys Phe Ser Pro Leu Ala Gln Ile Ser Gln
        195                 200                 205

Leu Ile Pro Glu Leu Asp Phe Pro Arg Lys Ala Leu Pro Asp Cys Phe
    210                 215                 220

His Ala Val Gly Pro Leu Arg Gln Pro Gln Gly Thr Pro Gly Ser Ser
225                 230                 235                 240

Thr Ser Tyr Phe Pro Ser Pro Asp Lys Pro Arg Ile Phe Ala Ser Leu
                245                 250                 255

Gly Thr Leu Gln Gly His Arg Tyr Gly Leu Phe Arg Thr Ile Ala Lys
            260                 265                 270

Ala Cys Glu Glu Val Asp Ala Gln Leu Leu Leu Ala His Cys Gly Gly
        275                 280                 285

Leu Ser Ala Thr Gln Ala Gly Glu Leu Ala Arg Gly Gly Asp Ile Gln
    290                 295                 300

Val Val Asp Phe Ala Asp Gln Ser Ala Ala Leu Ser Gln Ala Gln Leu
305                 310                 315                 320

Thr Ile Thr His Gly Gly Met Asn Thr Val Leu Asp Ala Ile Ala Ser
                325                 330                 335

Arg Thr Pro Leu Leu Ala Leu Pro Leu Ala Phe Asp Gln Pro Gly Val
            340                 345                 350

Ala Ser Arg Ile Val Tyr His Gly Ile Gly Lys Arg Ala Ser Arg Phe
        355                 360                 365

Thr Thr Ser His Ala Leu Ala Arg Gln Ile Arg Ser Leu Leu Thr Asn
    370                 375                 380

Thr Asp Tyr Pro Gln Arg Met Thr Lys Ile Gln Ala Ala Leu Arg Leu
```

-continued

```
            385                 390                 395                 400
Ala Gly Gly Thr Pro Ala Ala Asp Ile Val Glu Gln Ala Met Arg
                    405                 410                 415

Thr Cys Gln Pro Val Leu Ser Gly Gln Asp Tyr Ala Thr Ala Leu
                420                 425                 430

<210> SEQ ID NO 5
<211> LENGTH: 1149
<212> TYPE: DNA
<213> ORGANISM: Pantoea stewartii
<220> FEATURE:
<221> NAME/KEY: CDS
<222> LOCATION: (1)..(1149)

<400> SEQUENCE: 5 atg caa ccg cac tat gat ctc att ctg gtc ggt gcc ggt ctg gct aat        48
Met Gln Pro His Tyr Asp Leu Ile Leu Val Gly Ala Gly Leu Ala Asn
1               5                   10                  15 ggc ctt atc gcg ctc cgg ctt cag caa cag cat ccg gat atg cgg atc        96
Gly Leu Ile Ala Leu Arg Leu Gln Gln Gln His Pro Asp Met Arg Ile
            20                  25                  30 ttg ctt att gag gcg ggt cct gag gcg gga ggg aac cat acc tgg tcc       144
Leu Leu Ile Glu Ala Gly Pro Glu Ala Gly Gly Asn His Thr Trp Ser
        35                  40                  45 ttt cac gaa gag gat tta acg ctg aat cag cat cgc tgg ata gcg ccg       192
Phe His Glu Glu Asp Leu Thr Leu Asn Gln His Arg Trp Ile Ala Pro
    50                  55                  60 ctt gtg tca cat cac tgg ccc gac tac cag gtt cgt ttc ccc caa cgc       240
Leu Val Val His His Trp Pro Asp Tyr Gln Val Arg Phe Pro Gln Arg
65                  70                  75                  80 cgt cgc cat gtg aac agt ggc tac tac tgc gtg acc tcc cgg cat ttc       288
Arg Arg His Val Asn Ser Gly Tyr Tyr Cys Val Thr Ser Arg His Phe
                85                  90                  95 gcc ggg ata ctc cgg caa cag ttt gga caa cat tta tgg ctg cat acc       336
Ala Gly Ile Leu Arg Gln Gln Phe Gly Gln His Leu Trp Leu His Thr
            100                 105                 110 gcg gtt tca gcc gtt cat gct gaa tcg gtc cag tta gcg gat ggc cgg       384
Ala Val Ser Ala Val His Ala Glu Ser Val Gln Leu Ala Asp Gly Arg
        115                 120                 125 att att cat gcc agt aca gtg atc gac gga cgg gtt tac acg cct gat       432
Ile Ile His Ala Ser Thr Val Ile Asp Gly Arg Gly Tyr Thr Pro Asp
    130                 135                 140 tct gca cta cgc gta gga ttc cag gca ttt atc ggt cag gag tgg caa       480
Ser Ala Leu Arg Val Gly Phe Gln Ala Phe Ile Gly Gln Glu Trp Gln
145                 150                 155                 160 ctg agc gcg ccg cat ggt tta tcg tca ccg att atc atg gat gcg acg       528
Leu Ser Ala Pro His Gly Leu Ser Ser Pro Ile Ile Met Asp Ala Thr
                165                 170                 175 gtc gat cag caa aat ggc tac cgc ttt gtt tat acc ctg ccg ctt tcc       576
Val Asp Gln Gln Asn Gly Tyr Arg Phe Val Tyr Thr Leu Pro Leu Ser
            180                 185                 190 gca acc gca ctg ctg atc gaa gac aca cac tac att gac aag gct aat       624
Ala Thr Ala Leu Leu Ile Glu Asp Thr His Tyr Ile Asp Lys Ala Asn
        195                 200                 205 ctt cag gcc gaa cgg gcg cgt cag aac att cgc gat tat gct gcg cga       672
Leu Gln Ala Glu Arg Ala Arg Gln Asn Ile Arg Asp Tyr Ala Ala Arg
    210                 215                 220 cag ggt tgg ccg tta cag acg ttg ctg cgg gaa gaa cag ggt gca ttg       720
Gln Gly Trp Pro Leu Gln Thr Leu Leu Arg Glu Glu Gln Gly Ala Leu
225                 230                 235                 240
```

```
ccc att acg tta acg ggc gat aat cgt cag ttt tgg caa cag caa ccg      768
Pro Ile Thr Leu Thr Gly Asp Asn Arg Gln Phe Trp Gln Gln Gln Pro
            245                 250                 255 caa gct tgt agc gga tta cgc gcc ggg ctg ttt cat ccg aca acc ggc      816
Gln Ala Cys Ser Gly Leu Arg Ala Gly Leu Phe His Pro Thr Thr Gly
        260                 265                 270 tac tcc cta ccg ctc gcg gtg gcg ctg gcc gat cgt ctc agc gcg ctg      864
Tyr Ser Leu Pro Leu Ala Val Ala Leu Ala Asp Arg Leu Ser Ala Leu
    275                 280                 285 gat gtg ttt acc tct tcc tct gtt cac cag acg att gct cac ttt gcc      912
Asp Val Phe Thr Ser Ser Ser Val His Gln Thr Ile Ala His Phe Ala
290                 295                 300 cag caa cgt tgg cag caa cag ggg ttt ttc cgc atg ctg aat cgc atg      960
Gln Gln Arg Trp Gln Gln Gln Gly Phe Phe Arg Met Leu Asn Arg Met
305                 310                 315                 320 ttg ttt tta gcc gga ccg gcc gag tca cgc tgg cgt gtg atg cag cgt     1008
Leu Phe Leu Ala Gly Pro Ala Glu Ser Arg Trp Arg Val Met Gln Arg
                325                 330                 335 ttc tat ggc tta ccc gag gat ttg att gcc cgc ttt tat gcg gga aaa     1056
Phe Tyr Gly Leu Pro Glu Asp Leu Ile Ala Arg Phe Tyr Ala Gly Lys
            340                 345                 350 ctc acc gtg acc gat cgg cta cgc att ctg agc ggc aag ccg ccc gtt     1104
Leu Thr Val Thr Asp Arg Leu Arg Ile Leu Ser Gly Lys Pro Pro Val
        355                 360                 365 ccc gtt ttc gcg gca ttg cag gca att atg acg act cat cgt tga         1149
Pro Val Phe Ala Ala Leu Gln Ala Ile Met Thr Thr His Arg
    370                 375                 380

<210> SEQ ID NO 6
<211> LENGTH: 382
<212> TYPE: PRT
<213> ORGANISM: Pantoea stewartii

<400> SEQUENCE: 6

Met Gln Pro His Tyr Asp Leu Ile Leu Val Gly Ala Gly Leu Ala Asn
1               5                   10                  15

Gly Leu Ile Ala Leu Arg Leu Gln Gln Gln His Pro Asp Met Arg Ile
            20                  25                  30

Leu Leu Ile Glu Ala Gly Pro Glu Ala Gly Gly Asn His Thr Trp Ser
        35                  40                  45

Phe His Glu Glu Asp Leu Thr Leu Asn Gln His Arg Trp Ile Ala Pro
    50                  55                  60

Leu Val Val His His Trp Pro Asp Tyr Gln Val Arg Phe Pro Gln Arg
65                  70                  75                  80

Arg Arg His Val Asn Ser Gly Tyr Tyr Cys Val Thr Ser Arg His Phe
                85                  90                  95

Ala Gly Ile Leu Arg Gln Gln Phe Gly Gln His Leu Trp Leu His Thr
            100                 105                 110

Ala Val Ser Ala Val His Ala Glu Ser Val Gln Leu Ala Asp Gly Arg
        115                 120                 125

Ile Ile His Ala Ser Thr Val Ile Asp Gly Arg Gly Tyr Thr Pro Asp
    130                 135                 140

Ser Ala Leu Arg Val Gly Phe Gln Ala Phe Ile Gly Gln Glu Trp Gln
145                 150                 155                 160

Leu Ser Ala Pro His Gly Leu Ser Ser Pro Ile Ile Met Asp Ala Thr
                165                 170                 175

Val Asp Gln Gln Asn Gly Tyr Arg Phe Val Tyr Thr Leu Pro Leu Ser
            180                 185                 190
```

```
Ala Thr Ala Leu Leu Ile Glu Asp Thr His Tyr Ile Asp Lys Ala Asn
            195                 200                 205

Leu Gln Ala Glu Arg Ala Arg Gln Asn Ile Arg Asp Tyr Ala Ala Arg
        210                 215                 220

Gln Gly Trp Pro Leu Gln Thr Leu Leu Arg Glu Gln Gly Ala Leu
225                 230                 235                 240

Pro Ile Thr Leu Thr Gly Asp Asn Arg Gln Phe Trp Gln Gln Pro
                245                 250                 255

Gln Ala Cys Ser Gly Leu Arg Ala Gly Leu Phe His Pro Thr Thr Gly
            260                 265                 270

Tyr Ser Leu Pro Leu Ala Val Ala Leu Ala Asp Arg Leu Ser Ala Leu
        275                 280                 285

Asp Val Phe Thr Ser Ser Val His Gln Thr Ile Ala His Phe Ala
    290                 295                 300

Gln Gln Arg Trp Gln Gln Gln Gly Phe Phe Arg Met Leu Asn Arg Met
305                 310                 315                 320

Leu Phe Leu Ala Gly Pro Ala Glu Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Val Thr Asp Arg Leu Arg Ile Leu Ser Gly Lys Pro Pro Val
        355                 360                 365
Pro Val Phe Ala Ala Leu Gln Ala Ile Met Thr Thr His Arg
    370                 375                 380

<210> SEQ ID NO 7
<211> LENGTH: 1479
<212> TYPE: DNA
<213> ORGANISM: Pantoea stewartii
<220> FEATURE:
<221> NAME/KEY: CDS
<222> LOCATION: (1)..(1479)

<400> SEQUENCE: 7 atg aaa cca act acg gta att ggt gcg ggc ttt ggt ggc ctg gca ctg      48
Met Lys Pro Thr Thr Val Ile Gly Ala Gly Phe Gly Gly Leu Ala Leu
1               5                   10                  15 gca att cgt tta cag gcc gca ggt att cct gtt ttg ctg ctt gag cag      96
Ala Ile Arg Leu Gln Ala Ala Gly Ile Pro Val Leu Leu Leu Glu Gln
            20                  25                  30 cgc gac aag ccg ggt ggc cgg gct tat gtt tat cag gag cag ggc ttt     144
Arg Asp Lys Pro Gly Gly Arg Ala Tyr Val Tyr Gln Glu Gln Gly Phe
        35                  40                  45 act ttt gat gca ggc cct acc gtt atc acc gat ccc agc gcg att gaa     192
Thr Phe Asp Ala Gly Pro Thr Val Ile Thr Asp Pro Ser Ala Ile Glu
    50                  55                  60 gaa ctg ttt gct ctg gcc ggt aaa cag ctt aag gat tac gtc gag ctg     240
Glu Leu Phe Ala Leu Ala Gly Lys Gln Leu Lys Asp Tyr Val Glu Leu
65                  70                  75                  80 ttg ccg gtc acg ccg ttt tat cgc ctg tgc tgg gag tcc ggc aag gtc     288
Leu Pro Val Thr Pro Phe Tyr Arg Leu Cys Trp Glu Ser Gly Lys Val
                85                  90                  95 ttc aat tac gat aac gac cag gcc cag tta gaa gcg cag ata cag cag     336
Phe Asn Tyr Asp Asn Asp Gln Ala Gln Leu Glu Ala Gln Ile Gln Gln
            100                 105                 110 ttt aat ccg cgc gat gtt gcg ggt tat cga gcg ttc ctt gac tat tcg     384
Phe Asn Pro Arg Asp Val Ala Gly Tyr Arg Ala Phe Leu Asp Tyr Ser
        115                 120                 125
```

```
cgt gcc gta ttc aat gag ggc tat ctg aag ctc ggc act gtg cct ttt    432
Arg Ala Val Phe Asn Glu Gly Tyr Leu Lys Leu Gly Thr Val Pro Phe
    130             135                 140 tta tcg ttc aaa gac atg ctt cgg gcc gcg ccc cag ttg gca aag ctg    480
Leu Ser Phe Lys Asp Met Leu Arg Ala Ala Pro Gln Leu Ala Lys Leu
145             150                 155                 160 cag gca tgg cgc agc gtt tac agt aaa gtt gcc ggc tac att gag gat    528
Gln Ala Trp Arg Ser Val Tyr Ser Lys Val Ala Gly Tyr Ile Glu Asp
                165                 170                 175 gag cat ctt cgg cag gcg ttt tct ttt cac tcg ctc tta gtg ggg ggg    576
Glu His Leu Arg Gln Ala Phe Ser Phe His Ser Leu Leu Val Gly Gly
            180                 185                 190 aat ccg ttt gca acc tcg tcc att tat acg ctg att cac gcg tta gaa    624
Asn Pro Phe Ala Thr Ser Ser Ile Tyr Thr Leu Ile His Ala Leu Glu
        195                 200                 205 cgg gaa tgg ggc gtc tgg ttt cca cgc ggt gga acc ggt gcg ctg gtc    672
Arg Glu Trp Gly Val Trp Phe Pro Arg Gly Gly Thr Gly Ala Leu Val
    210                 215                 220 aat ggc atg atc aag ctg ttt cag gat ctg ggc ggc gaa gtc gtg ctt    720
Asn Gly Met Ile Lys Leu Phe Gln Asp Leu Gly Gly Glu Val Val Leu
225             230                 235                 240 aac gcc cgg gtc agt cat atg gaa acc gtt ggg gac aag att cag gcc    768
Asn Ala Arg Val Ser His Met Glu Thr Val Gly Asp Lys Ile Gln Ala
                245                 250                 255 gtg cag ttg gaa gac ggc aga cgg ttt gaa acc tgc gcg gtg gcg tcg    816
Val Gln Leu Glu Asp Gly Arg Arg Phe Glu Thr Cys Ala Val Ala Ser
            260                 265                 270 aac gct gat gtt gta cat acc tat cgc gat ctg ctg tct cag cat ccc    864
Asn Ala Asp Val Val His Thr Tyr Arg Asp Leu Leu Ser Gln His Pro
        275                 280                 285 gca gcc gct aag cag gcg aaa aaa ctg caa tcc aag cgt atg agt aac    912
Ala Ala Ala Lys Gln Ala Lys Lys Leu Gln Ser Lys Arg Met Ser Asn
    290                 295                 300 tca ctg ttt gta ctc tat ttt ggt ctc aac cat cat cac gat caa ctc    960
Ser Leu Phe Val Leu Tyr Phe Gly Leu Asn His His His Asp Gln Leu
305             310                 315                 320 gcc cat cat acc gtc tgt ttt ggg cca cgc tac cgt gaa ctg att cac   1008
Ala His His Thr Val Cys Phe Gly Pro Arg Tyr Arg Glu Leu Ile His
                325                 330                 335 gaa att ttt aac cat gat ggt ctg gct gag gat ttt tcg ctt tat tta   1056
Glu Ile Phe Asn His Asp Gly Leu Ala Glu Asp Phe Ser Leu Tyr Leu
            340                 345                 350 cac gca cct tgt gtc acg gat ccg tca ctg gca ccg gaa ggg tgc ggc   1104
His Ala Pro Cys Val Thr Asp Pro Ser Leu Ala Pro Glu Gly Cys Gly
        355                 360                 365 agc tat tat gtg ctg gcg cct gtt cca cac tta ggc acg gcg aac ctc   1152
Ser Tyr Tyr Val Leu Ala Pro Val Pro His Leu Gly Thr Ala Asn Leu
    370                 375                 380 gac tgg gcg gta gaa gga ccc cga ctg cgc gat cgt att ttt gac tac   1200
Asp Trp Ala Val Glu Gly Pro Arg Leu Arg Asp Arg Ile Phe Asp Tyr
385             390                 395                 400 ctt gag caa cat tac atg cct ggc ttg cga agc cag ttg gtg acg cac   1248
Leu Glu Gln His Tyr Met Pro Gly Leu Arg Ser Gln Leu Val Thr His
                405                 410                 415 cgt atg ttt acg ccg ttc gat ttc cgc gac gag ctc aat gcc tgg caa   1296
Arg Met Phe Thr Pro Phe Asp Phe Arg Asp Glu Leu Asn Ala Trp Gln
            420                 425                 430 ggt tcg gcc ttc tcg gtt gaa cct att ctg acc cag agc gcc tgg ttc   1344
Gly Ser Ala Phe Ser Val Glu Pro Ile Leu Thr Gln Ser Ala Trp Phe
        435                 440                 445
```

-continued

```
cga cca cat aac cgc gat aag cac att gat aat ctt tat ctg gtt ggc    1392
Arg Pro His Asn Arg Asp Lys His Ile Asp Asn Leu Tyr Leu Val Gly
    450                 455                 460 gca ggc acc cat cct ggc gcg ggc att ccc ggc gta atc ggc tcg gcg    1440
Ala Gly Thr His Pro Gly Ala Gly Ile Pro Gly Val Ile Gly Ser Ala
465                 470                 475                 480 aag gcg acg gca ggc tta atg ctg gag gac ctg att tga                1479
Lys Ala Thr Ala Gly Leu Met Leu Glu Asp Leu Ile
                485                 490

<210> SEQ ID NO 8
<211> LENGTH: 492
<212> TYPE: PRT
<213> ORGANISM: Pantoea stewartii

<400> SEQUENCE: 8

Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
            20                  25                  30

Arg Asp Lys Pro Gly Gly Arg Ala Tyr Val Tyr Gln Glu Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Asp Tyr Val Glu Leu
65                  70                  75                  80

Leu Pro Val Thr Pro Phe Tyr Arg Leu Cys Trp Glu Ser Gly Lys Val
                85                  90                  95

Phe Asn Tyr Asp Asn Asp Gln Ala Gln Leu Glu Ala Gln Ile Gln Gln
            100                 105                 110

Phe Asn Pro Arg Asp Val Ala Gly Tyr Arg Ala Phe Leu Asp Tyr Ser
        115                 120                 125

Arg Ala Val Phe Asn Glu Gly Tyr Leu Lys Leu Gly Thr Val Pro Phe
    130                 135                 140

Leu Ser Phe Lys Asp Met Leu Arg Ala Ala Pro Gln Leu Ala Lys Leu
145                 150                 155                 160

Gln Ala Trp Arg Ser Val Tyr Ser Lys Val Ala Gly Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Asn Gly Met Ile Lys Leu Phe Gln Asp Leu Gly Gly Glu Val Val Leu
225                 230                 235                 240

Asn Ala Arg Val Ser His Met Glu Thr Val Gly Asp Lys Ile Gln Ala
                245                 250                 255

Val Gln Leu Glu Asp Gly Arg Arg Phe Glu Thr Cys Ala Val Ala Ser
            260                 265                 270

Asn Ala Asp Val His Thr Tyr Arg Asp Leu Leu Ser Gln His Pro
        275                 280                 285

Ala Ala Ala Lys Gln Ala Lys Lys Leu Gln Ser Lys Arg Met Ser Asn
    290                 295                 300

Ser Leu Phe Val Leu Tyr Phe Gly Leu Asn His His His Asp Gln Leu
```

-continued

```
            305                 310                 315                 320
        Ala His His Thr Val Cys Phe Gly Pro Arg Tyr Arg Glu Leu Ile His
                        325                 330                 335

Glu Ile Phe Asn His Asp Gly Leu Ala Glu Asp Phe Ser Leu Tyr Leu
                        340                 345                 350

His Ala Pro Cys Val Thr Asp Pro Ser Leu Ala Pro Glu Gly Cys Gly
                        355                 360                 365

Ser Tyr Tyr Val Leu Ala Pro Val Pro His Leu Gly Thr Ala Asn Leu
                370                 375                 380

Asp Trp Ala Val Glu Gly Pro Arg Leu Arg Asp Arg Ile Phe Asp Tyr
        385                 390                 395                 400

Leu Glu Gln His Tyr Met Pro Gly Leu Arg Ser Gln Leu Val Thr His
                        405                 410                 415

Arg Met Phe Thr Pro Phe Asp Phe Arg Asp Glu Leu Asn Ala Trp Gln
                        420                 425                 430

Gly Ser Ala Phe Ser Val Glu Pro Ile Leu Thr Gln Ser Ala Trp Phe
                        435                 440                 445

Arg Pro His Asn Arg Asp Lys His Ile Asp Asn Leu Tyr Leu Val Gly
                        450                 455                 460

Ala Gly Thr His Pro Gly Ala Gly Ile Pro Gly Val Ile Gly Ser Ala
        465                 470                 475                 480

Lys Ala Thr Ala Gly Leu Met Leu Glu Asp Leu Ile
                        485                 490

<210> SEQ ID NO 9
<211> LENGTH: 891
<212> TYPE: DNA
<213> ORGANISM: Pantoea stewartii
<220> FEATURE:
<221> NAME/KEY: CDS
<222> LOCATION: (1)..(891)

<400> SEQUENCE: 9 atg gcg gtt ggc tcg aaa agc ttt gcg act gca tcg acg ctt ttc gac        48
Met Ala Val Gly Ser Lys Ser Phe Ala Thr Ala Ser Thr Leu Phe Asp
1               5                   10                  15 gcc aaa acc cgt cgc agc gtg ctg atg ctt tac gca tgg tgc cgc cac        96
Ala Lys Thr Arg Arg Ser Val Leu Met Leu Tyr Ala Trp Cys Arg His
                20                  25                  30 tgc gac gac gtc att gac gat caa aca ctg ggc ttt cat gcc gac cag       144
Cys Asp Asp Val Ile Asp Asp Gln Thr Leu Gly Phe His Ala Asp Gln
            35                  40                  45 ccc tct tcg cag atg cct gag cag cgc ctg cag cag ctt gaa atg aaa       192
Pro Ser Ser Gln Met Pro Glu Gln Arg Leu Gln Gln Leu Glu Met Lys
        50                  55                  60 acg cgt cag gcc tac gcc ggt tcg caa atg cac gag ccc gct ttt gcc       240
Thr Arg Gln Ala Tyr Ala Gly Ser Gln Met His Glu Pro Ala Phe Ala
65                  70                  75                  80 gcg ttt cag gag gtc gcg atg gcg cat gat atc gct ccc gcc tac gcg       288
Ala Phe Gln Glu Val Ala Met Ala His Asp Ile Ala Pro Ala Tyr Ala
                85                  90                  95 ttc gac cat ctg gaa ggt ttt gcc atg gat gtg cgc gaa acg cgc tac       336
Phe Asp His Leu Glu Gly Phe Ala Met Asp Val Arg Glu Thr Arg Tyr
                100                 105                 110 ctg aca ctg gac gat acg ctg cgt tat tgc tat cac gtc gcc ggt gtt       384
Leu Thr Leu Asp Asp Thr Leu Arg Tyr Cys Tyr His Val Ala Gly Val
            115                 120                 125 gtg ggc ctg atg atg gcg caa att atg ggc gtt cgc gat aac gcc acg       432
```

```
Val Gly Leu Met Met Ala Gln Ile Met Gly Val Arg Asp Asn Ala Thr
        130                 135                 140 ctc gat cgc gcc tgc gat ctc ggg ctg gct ttc cag ttg acc aac att    480
Leu Asp Arg Ala Cys Asp Leu Gly Leu Ala Phe Gln Leu Thr Asn Ile
145                 150                 155                 160 gcg cgt gat att gtc gac gat gct cag gtg ggc cgc tgt tat ctg cct    528
Ala Arg Asp Ile Val Asp Asp Ala Gln Val Gly Arg Cys Tyr Leu Pro
                165                 170                 175 gaa agc tgg ctg gaa gag gaa gga ctg acg aaa gcg aat tat gct gcg    576
Glu Ser Trp Leu Glu Glu Glu Gly Leu Thr Lys Ala Asn Tyr Ala Ala
            180                 185                 190 cca gaa aac cgg cag gcc tta agc cgt atc gcc ggg cga ctg gta cgg    624
Pro Glu Asn Arg Gln Ala Leu Ser Arg Ile Ala Gly Arg Leu Val Arg
        195                 200                 205 gaa gcg gaa ccc tat tac gta tca tca atg gcc ggt ctg gca caa tta    672
Glu Ala Glu Pro Tyr Tyr Val Ser Ser Met Ala Gly Leu Ala Gln Leu
210                 215                 220 ccc tta cgc tcg gcc tgg gcc atc gcg aca gcg aag cag gtg tac cgt    720
Pro Leu Arg Ser Ala Trp Ala Ile Ala Thr Ala Lys Gln Val Tyr Arg
225                 230                 235                 240 aaa att ggc gtg aaa gtt gaa cag gcc ggt aag cag gcc tgg gat cat    768
Lys Ile Gly Val Lys Val Glu Gln Ala Gly Lys Gln Ala Trp Asp His
                245                 250                 255 cgc cag tcc acg tcc acc gcc gaa aaa tta acg ctt ttg ctg acg gca    816
Arg Gln Ser Thr Ser Thr Ala Glu Lys Leu Thr Leu Leu Leu Thr Ala
            260                 265                 270 tcc ggt cag gca gtt act tcc cgg atg aag acg tat cca ccc cgt cct    864
Ser Gly Gln Ala Val Thr Ser Arg Met Lys Thr Tyr Pro Pro Arg Pro
        275                 280                 285 gct cat ctc tgg cag cgc ccg atc tag                                891
Ala His Leu Trp Gln Arg Pro Ile
        290                 295

<210> SEQ ID NO 10
<211> LENGTH: 296
<212> TYPE: PRT
<213> ORGANISM: Pantoea stewartii

<400> SEQUENCE: 10

Met Ala Val Gly Ser Lys Ser Phe Ala Thr Ala Ser Thr Leu Phe Asp
1               5                   10                  15

Ala Lys Thr Arg Arg Ser Val Leu Met Leu Tyr Ala Trp Cys Arg His
            20                  25                  30

Cys Asp Asp Val Ile Asp Asp Gln Thr Leu Gly Phe His Ala Asp Gln
        35                  40                  45

Pro Ser Ser Gln Met Pro Glu Gln Arg Leu Gln Gln Leu Glu Met Lys
    50                  55                  60

Thr Arg Gln Ala Tyr Ala Gly Ser Gln Met His Glu Pro Ala Phe Ala
65                  70                  75                  80

Ala Phe Gln Glu Val Ala Met Ala His Asp Ile Ala Pro Ala Tyr Ala
                85                  90                  95

Phe Asp His Leu Glu Gly Phe Ala Met Asp Val Arg Glu Thr Arg Tyr
            100                 105                 110

Leu Thr Leu Asp Asp Thr Leu Arg Tyr Cys Tyr His Val Ala Gly Val
        115                 120                 125

Val Gly Leu Met Met Ala Gln Ile Met Gly Val Arg Asp Asn Ala Thr
    130                 135                 140

Leu Asp Arg Ala Cys Asp Leu Gly Leu Ala Phe Gln Leu Thr Asn Ile
```

-continued

```
                145                 150                 155                 160
        Ala Arg Asp Ile Val Asp Asp Ala Gln Val Gly Arg Cys Tyr Leu Pro
                        165                 170                 175

Glu Ser Trp Leu Glu Glu Glu Gly Leu Thr Lys Ala Asn Tyr Ala Ala
                    180                 185                 190

Pro Glu Asn Arg Gln Ala Leu Ser Arg Ile Ala Gly Arg Leu Val Arg
                    195                 200                 205

Glu Ala Glu Pro Tyr Tyr Val Ser Ser Met Ala Gly Leu Ala Gln Leu
                210                 215                 220

Pro Leu Arg Ser Ala Trp Ala Ile Ala Thr Ala Lys Gln Val Tyr Arg
        225                 230                 235                 240

Lys Ile Gly Val Lys Val Glu Gln Ala Gly Lys Gln Ala Trp Asp His
                        245                 250                 255

Arg Gln Ser Thr Ser Thr Ala Glu Lys Leu Thr Leu Leu Thr Ala
                    260                 265                 270

Ser Gly Gln Ala Val Thr Ser Arg Met Lys Thr Tyr Pro Pro Arg Pro
                    275                 280                 285

Ala His Leu Trp Gln Arg Pro Ile
            290                 295

<210> SEQ ID NO 11
<211> LENGTH: 528
<212> TYPE: DNA
<213> ORGANISM: Pantoea stewartii
<220> FEATURE:
<221> NAME/KEY: CDS
<222> LOCATION: (1)..(528)

<400> SEQUENCE: 11 atg ttg tgg att tgg aat gcc ctg atc gtg ttt gtc acc gtg gtc ggc      48
Met Leu Trp Ile Trp Asn Ala Leu Ile Val Phe Val Thr Val Val Gly
1               5                   10                  15 atg gaa gtg gtt gct gca ctg gca cat aaa tac atc atg cac ggc tgg      96
Met Glu Val Val Ala Ala Leu Ala His Lys Tyr Ile Met His Gly Trp
                20                  25                  30 ggt tgg ggc tgg cat ctt tca cat cat gaa ccg cgt aaa ggc gca ttt     144
Gly Trp Gly Trp His Leu Ser His His Glu Pro Arg Lys Gly Ala Phe
            35                  40                  45 gaa gtt aac gat ctc tat gcc gtg gta ttc gcc att gtg tcg att gcc     192
Glu Val Asn Asp Leu Tyr Ala Val Val Phe Ala Ile Val Ser Ile Ala
        50                  55                  60 ctg att tac ttc ggc agt aca gga atc tgg ccg ctc cag tgg att ggt     240
Leu Ile Tyr Phe Gly Ser Thr Gly Ile Trp Pro Leu Gln Trp Ile Gly
65                  70                  75                  80 gca ggc atg acc gct tat ggt tta ctg tat ttt atg gtc cac gac gga     288
Ala Gly Met Thr Ala Tyr Gly Leu Leu Tyr Phe Met Val His Asp Gly
                85                  90                  95 ctg gta cac cag cgc tgg ccg ttc cgc tac ata ccg cgc aaa ggc tac     336
Leu Val His Gln Arg Trp Pro Phe Arg Tyr Ile Pro Arg Lys Gly Tyr
            100                 105                 110 ctg aaa cgg tta tac atg gcc cac cgt atg cat cat gct gta agg gga     384
Leu Lys Arg Leu Tyr Met Ala His Arg Met His His Ala Val Arg Gly
        115                 120                 125 aaa gag ggc tgc gtg tcc ttt ggt ttt ctg tac gcg cca ccg tta tct     432
Lys Glu Gly Cys Val Ser Phe Gly Phe Leu Tyr Ala Pro Pro Leu Ser
    130                 135                 140 aaa ctt cag gcg acg ctg aga gaa agg cat gcg gct aga tcg ggc gct     480
Lys Leu Gln Ala Thr Leu Arg Glu Arg His Ala Ala Arg Ser Gly Ala
145                 150                 155                 160
```

```
gcc aga gat gag cag gac ggg gtg gat acg tct tca tcc ggg aag taa       528
Ala Arg Asp Glu Gln Asp Gly Val Asp Thr Ser Ser Ser Gly Lys
                165                 170                 175

<210> SEQ ID NO 12
<211> LENGTH: 175
<212> TYPE: PRT
<213> ORGANISM: Pantoea stewartii

<400> SEQUENCE: 12

Met Leu Trp Ile Trp Asn Ala Leu Ile Val Phe Val Thr Val Gly
1               5                   10                  15

Met Glu Val Val Ala Ala Leu Ala His Lys Tyr Ile Met His Gly Trp
            20                  25                  30

Gly Trp Gly Trp His Leu Ser His Glu Pro Arg Lys Gly Ala Phe
        35                  40                  45

Glu Val Asn Asp Leu Tyr Ala Val Phe Ala Ile Val Ser Ile Ala
    50                  55                  60

Leu Ile Tyr Phe Gly Ser Thr Gly Ile Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His His Ala Val Arg Gly
        115                 120                 125

Lys Glu Gly Cys Val Ser Phe Gly Phe Leu Tyr Ala Pro Pro Leu Ser
    130                 135                 140

Lys Leu Gln Ala Thr Leu Arg Glu Arg His Ala Ala Arg Ser Gly Ala
145                 150                 155                 160

Ala Arg Asp Glu Gln Asp Gly Val Asp Thr Ser Ser Ser Gly Lys
                165                 170                 175

<210> SEQ ID NO 13
<211> LENGTH: 25
<212> TYPE: DNA
<213> ORGANISM: Artificial sequence
<220> FEATURE:
<223> OTHER INFORMATION: First primer used to amplify carotenoid gene
                        cluster.

<400> SEQUENCE: 13
atgacggtct gcgcaaaaaa acacg                                            25

<210> SEQ ID NO 14
<211> LENGTH: 28
<212> TYPE: DNA
<213> ORGANISM: Artificial sequence
<220> FEATURE:
<223> OTHER INFORMATION: Second primer used to amplify carotenoid gene
                        cluster.

<400> SEQUENCE: 14
gagaaattat gttgtggatt tggaatgc                                         28

<210> SEQ ID NO 15
<211> LENGTH: 21
<212> TYPE: DNA
<213> ORGANISM: Artificial sequence
<220> FEATURE:
<223> OTHER INFORMATION: Primer Tn5PCRF.
```

```
<400> SEQUENCE: 15
gctgagttga aggatcagat c                                              21

<210> SEQ ID NO 16
<211> LENGTH: 21
<212> TYPE: DNA
<213> ORGANISM: Artificial sequence
<220> FEATURE:
<223> OTHER INFORMATION: Primer Tn5PCRR.

<400> SEQUENCE: 16
cgagcaagac gtttcccgtt g                                              21

<210> SEQ ID NO 17
<211> LENGTH: 25
<212> TYPE: DNA
<213> ORGANISM: Artificial sequence
<220> FEATURE:
<223> OTHER INFORMATION: Primer Kan-2 FP-1

<400> SEQUENCE: 17
acctacaaca aagctctcat caacc                                          25

<210> SEQ ID NO 18
<211> LENGTH: 25
<212> TYPE: DNA
<213> ORGANISM: Artificial sequence
<220> FEATURE:
<223> OTHER INFORMATION: Primer Kan-2 RP-1

<400> SEQUENCE: 18
gcaatgtaac atcagagatt ttgag                                          25

<210> SEQ ID NO 19
<211> LENGTH: 20
<212> TYPE: DNA
<213> ORGANISM: Artificial sequence
<220> FEATURE:
<223> OTHER INFORMATION: Primer Y1_F

<400> SEQUENCE: 19
agcaccatga tcatctggcg                                                20

<210> SEQ ID NO 20
<211> LENGTH: 20
<212> TYPE: DNA
<213> ORGANISM: Artificial sequence
<220> FEATURE:
<223> OTHER INFORMATION: Primer Y1_R

<400> SEQUENCE: 20
cggttgcgct ggaagaaaac                                                20

<210> SEQ ID NO 21
<211> LENGTH: 20
<212> TYPE: DNA
<213> ORGANISM: Artificial sequence
<220> FEATURE:
<223> OTHER INFORMATION: Primer Y4_F

<400> SEQUENCE: 21
caccctgtgc cattttcagc                                                20

<210> SEQ ID NO 22
```

```
<211> LENGTH: 20
<212> TYPE: DNA
<213> ORGANISM: Artificial sequence
<220> FEATURE:
<223> OTHER INFORMATION: Primer Y4_R

<400> SEQUENCE: 22
cgttctgggt atggcccaga                                               20

<210> SEQ ID NO 23
<211> LENGTH: 20
<212> TYPE: DNA
<213> ORGANISM: Artificial sequence
<220> FEATURE:
<223> OTHER INFORMATION: Primer Y8_1_F

<400> SEQUENCE: 23
aaagctaacc cgtggcagca                                               20

<210> SEQ ID NO 24
<211> LENGTH: 20
<212> TYPE: DNA
<213> ORGANISM: Artificial sequence
<220> FEATURE:
<223> OTHER INFORMATION: Primer Y8_1_R

<400> SEQUENCE: 24
tttgcgttcc ccgaggcata                                               20

<210> SEQ ID NO 25
<211> LENGTH: 20
<212> TYPE: DNA
<213> ORGANISM: Artificial sequence
<220> FEATURE:
<223> OTHER INFORMATION: Primer Y12_F

<400> SEQUENCE: 25
ttccgaaatg gcgtcagctc                                               20

<210> SEQ ID NO 26
<211> LENGTH: 25
<212> TYPE: DNA
<213> ORGANISM: Artificial sequence
<220> FEATURE:
<223> OTHER INFORMATION: Primer Y12_R

<400> SEQUENCE: 26
atctctacat tgattatgag tattc                                         25

<210> SEQ ID NO 27
<211> LENGTH: 20
<212> TYPE: DNA
<213> ORGANISM: Artificial sequence
<220> FEATURE:
<223> OTHER INFORMATION: Primer Y15_F

<400> SEQUENCE: 27
ggatcgatct tgagatgacc                                               20

<210> SEQ ID NO 28
<211> LENGTH: 24
<212> TYPE: DNA
<213> ORGANISM: Artificial sequence
<220> FEATURE:
<223> OTHER INFORMATION: Primer Y15_R

<400> SEQUENCE: 28
```
gctttcgtaa ttttcgcatt tctg                                          24

<210> SEQ ID NO 29
<211> LENGTH: 20
<212> TYPE: DNA
<213> ORGANISM: Artificial sequence
<220> FEATURE:
<223> OTHER INFORMATION: Primer Y16_F

<400> SEQUENCE: 29
cacgccaagt tgcgcaagta                                               20

<210> SEQ ID NO 30
<211> LENGTH: 20
<212> TYPE: DNA
<213> ORGANISM: Artificial sequence
<220> FEATURE:
<223> OTHER INFORMATION: Primer Y16_R

<400> SEQUENCE: 30
gcagaaaatg gtgactcagg                                               20

<210> SEQ ID NO 31
<211> LENGTH: 20
<212> TYPE: DNA
<213> ORGANISM: Artificial sequence
<220> FEATURE:
<223> OTHER INFORMATION: Primer Y17_F

<400> SEQUENCE: 31
ggcgatcctc gtcgatttct                                               20

<210> SEQ ID NO 32
<211> LENGTH: 20
<212> TYPE: DNA
<213> ORGANISM: Artificial sequence
<220> FEATURE:
<223> OTHER INFORMATION: Primer Y17_R

<400> SEQUENCE: 32
acgcagacga gagtttgcgt                                               20

<210> SEQ ID NO 33
<211> LENGTH: 20
<212> TYPE: DNA
<213> ORGANISM: Artificial sequence
<220> FEATURE:
<223> OTHER INFORMATION: Primer Y21_F

<400> SEQUENCE: 33
accgaatgcc cttgctgttg                                               20

<210> SEQ ID NO 34
<211> LENGTH: 20
<212> TYPE: DNA
<213> ORGANISM: Artificial sequence
<220> FEATURE:
<223> OTHER INFORMATION: Primer Y21_R

<400> SEQUENCE: 34
gggtgttcag gtatggctta                                               20

<210> SEQ ID NO 35
<211> LENGTH: 3159
<212> TYPE: DNA

<213> ORGANISM: Escherichia coli

<400> SEQUENCE: 35

| | | | | | | |
|---|---|---|---|---|---|---|
| atgcctgtta | taactcttcc | tgatggcagc | caacgccatt | acgatcacgc | tgtaagcccc | 60 |
| atggatgttg | cgctggacat | tggtccaggt | ctggcgaaag | cctgtatcgc | agggcgcgtt | 120 |
| aatggcgaac | tggttgatgc | ttgcgatctg | attgaaaacg | acgcacaact | gtcgatcatt | 180 |
| accgccaaag | acgaagaagg | tctggagatc | attcgtcact | cctgtgcgca | cctgttaggg | 240 |
| cacgcgatta | acaactttg | ccgcatacc | aaaatggcaa | tcggcccggt | tattgacaac | 300 |
| ggttttatt | acgacgttga | tcttgaccgc | acgttaaccc | aggaagatgt | cgaagcactc | 360 |
| gagaagcgga | tgcatgagct | tgctgagaaa | aactacgacg | tcattaagaa | gaaagtcagc | 420 |
| tggcacgaag | cgcgtgaaac | tttcgccaac | cgtggggaga | gctacaaagt | ctccattctt | 480 |
| gacgaaaaca | tcgcccatga | tgacaagcca | ggtctgtact | ccatgaaga | atatgtcgat | 540 |
| atgtgccgcg | gtccgcacgt | accgaacatg | cgtttctgcc | atcatttcaa | actaatgaaa | 600 |
| acggcagggg | cttactggcg | tggcgacagc | aacaacaaaa | tgttgcaacg | tatttacggt | 660 |
| acggcgtggg | cagacaaaaa | agcacttaac | gcttacctgc | agcgcctgga | agaagccgcg | 720 |
| aaacgcgacc | accgtaaaat | cggtaaacag | ctcgacctgt | accatatgca | ggaagaagcg | 780 |
| ccgggtatgg | tattctggca | aacgacggc | tggaccatct | tccgtgaact | ggaagtgttt | 840 |
| gttcgttcta | aactgaaaga | gtaccagtat | caggaagtta | aggtccgtt | catgatggac | 900 |
| cgtgtccctgt | gggaaaaaac | cggtcactgg | gacaactaca | agatgcaat | gttcaccaca | 960 |
| tcttctgaga | accgtgaata | ctgcattaag | ccgatgaact | gcccgggtca | cgtacaaatt | 1020 |
| ttcaaccagg | ggctgaagtc | ttatcgcgat | ctgccgctgc | gtatggccga | gtttggtagc | 1080 |
| tgccaccgta | acgagccgtc | aggttcgctg | catggcctga | tgcgcgtgcg | tggatttacc | 1140 |
| caggatgacg | cgcatatctt | ctgtactgaa | gaacaaattc | gcgatgaagt | taacggatgt | 1200 |
| atccgtttag | tctatgatat | gtacagcact | tttggcttcg | agaagatcgt | cgtcaaactc | 1260 |
| tccactcgtc | ctgaaaaacg | tattggcagc | gacgaaatgt | gggatcgtgc | tgaggcggac | 1320 |
| ctggcggttg | cgctggaaga | aaacaacatc | ccgtttgaat | atcaactggg | tgaaggcgct | 1380 |
| ttctacggtc | cgaaaattga | atttacccctg | tatgactgcc | tcgatcgtgc | atggcagtgc | 1440 |
| ggtacagtac | agctggactt | ctctttgccg | tctcgtctga | gcgcttctta | tgtaggcgaa | 1500 |
| gacaatgaac | gtaaagtacc | ggtaatgatt | caccgcgcaa | ttctggggtc | gatggaacgt | 1560 |
| ttcatcggta | tcctgaccga | agagttcgct | ggtttcttcc | cgacctggct | tgcgccggtt | 1620 |
| caggttgtta | tcatgaatat | taccgattca | cagtctgaat | acgttaacga | attgacgcaa | 1680 |
| aaactatcaa | atgcgggcat | tcgtgttaaa | gcagacttga | gaaatgagaa | gattggcttt | 1740 |
| aaaatccgcg | agcacacttt | gcgtcgcgtc | ccatatatgc | tggtctgtgg | tgataaagag | 1800 |
| gtggaatcag | gcaaagttgc | cgttcgcacc | cgccgtggta | aagacctggg | aagcatggac | 1860 |
| gtaaatgaag | tgatcgagaa | gctgcaacaa | gagattcgca | gccgcagtct | taaacctgtc | 1920 |
| tcttatacac | atctcaacca | tcatcgatga | attgtgtctc | aaaatctctg | atgttacatt | 1980 |
| gcacaagata | aaaatatatc | atcatgaaca | ataaaactgt | ctgcttacat | aaacagtaat | 2040 |
| acaagggggtg | ttatgagcca | tattcaacgg | gaaacgtctt | gctcgaggcc | gcgattaaat | 2100 |
| tccaacatgg | atgctgattt | atatgggtat | aaatgggctc | gcgataatgt | cggcaatca | 2160 |
| ggtgcgacaa | tctatcgatt | gtatgggaag | cccgatgcgc | cagagttgtt | tctgaaacat | 2220 |
| ggcaaaggta | gcgttgccaa | tgatgttaca | gatgagatgg | tcagactaaa | ctggctgacg | 2280 |

```
gaatttatgc ctcttccgac catcaagcat tttatccgta ctcctgatga tgcatggtta    2340
ctcaccactg cgatccccgg aaaaacagca ttccaggtat tagaagaata tcctgattca    2400
ggtgaaaata ttgttgatgc gctggcagtg ttcctgcgcc ggttgcattc gattcctgtt    2460
tgtaattgtc cttttaacag cgatcgcgta tttcgtctcg ctcaggcgca atcacgaatg    2520
aataacggtt tggttgatgc gagtgatttt gatgacgagc gtaatggctg gcctgttgaa    2580
caagtctgga agaaatgca taaacttttg ccattctcac cggattcagt cgtcactcat    2640
ggtgatttct cacttgataa ccttattttt gacgagggga aattaatagg ttgtattgat    2700
gttggacgag tcggaatcgc agaccgatac caggatcttg ccatcctatg gaactgcctc    2760
ggtgagtttt ctccttcatt acagaaacgg ctttttcaaa aatatggtat tgataatcct    2820
gatatgaata aattgcagtt tcatttgatg ctcgatgagt ttttctaatc agaattggtt    2880
aattggttgt aacactggca gagcattacg ctgacttgac gggacggcgg ctttgttgaa    2940
taaatcgaac ttttgctgag ttgaaggatc agatcacgca tcttcccgac aacgcagacc    3000
gttccgtggc aaagcaaaag ttcaaaatca ccaactggtc cacctacaac aaagctctca    3060
tcaaccgtgg cggggatcct ctagagtcga cctgcaggca tgcaagcttc agggttgaga    3120
tgtgtataag agacaggtct taaacaattg gaggaataa                          3159

<210> SEQ ID NO 36
<211> LENGTH: 3171
<212> TYPE: DNA
<213> ORGANISM: Escherichia coli

<400> SEQUENCE: 36
atgatgagtt atgtagactg gccgccatta attttgaggc acacgtacta catggctgaa      60
ttcgaaacca ctttttgcaga tctgggcctg aaggctccta tccttgaagc ccttaacgat     120
ctgggttacg aaaaaccatc tccaattcag gcagagtgta ttccacatct gctgaatggc     180
cgcgacgttc tgggtatggc ccagacgggg agcggaaaaa ctgcagcatt ctctttacct     240
ctgttgcaga atcttgatcc tgagctgaaa gcaccacaga ttctggtgct ggcaccgacc     300
cgcgaactgg cggtacaggt tgctgaagca atgacggatt tctctaaaca catgcgcggc     360
gtaaatgtgg ttgctctgta cggcggccag cgttatgacg tgcaattacg cgccctgcgt     420
caggggccgc agatcgttgt cggtactccg ggccgtctgc tggaccacct gaaacgtggc     480
actctggacc tctctaaact gagcggtctg gttctggatg aagctgacga aatgctgcgc     540
atgggcttca tcgaagacgt tgaaaccatt atggcgcaga tcccggaagg tcatcagacc     600
gctctgttct ctgcaaccat gccggaagcg attcgtcgca ttacccgccg ctttatgaaa     660
gagccgcagg aagtgcgcat tcagtccagc gtgactaccc gtcctgacat cagccagagc     720
tactggactg tctggggtat gcgcaaaaac gaagcactgg tacgctgtct cttatacaca     780
tctcaaccat catcgatgaa ttgtgtctca aaatctctga tgttacattg cacaagataa     840
aaatatatca tcatgaacaa taaaactgtc tgcttacata acagtaata caagggggtgt     900 tatgagccat attcaacggg aaacgtcttg ctcgaggccg cgattaaatt ccaacatgga     960
tgctgattta tatgggtata atgggctcg cgataatgtc gggcaatcag gtgcgacaat    1020
ctatcgattg tatgggaagc ccgatgcgcc agagttgttt ctgaaacatg gcaaaggtag    1080
cgttgccaat gatgttacag atgagatggt cagactaaac tggctgacgg aatttatgcc    1140
tcttccgacc atcaagcatt ttatccgtac tcctgatgat gcatggttac tcaccactgc    1200
```

-continued

```
gatccccgga aaaacagcat tccaggtatt agaagaatat cctgattcag gtgaaaatat    1260
tgttgatgcg ctggcagtgt tcctgcgccg gttgcattcg attcctgttt gtaattgtcc    1320
ttttaacagc gatcgcgtat ttcgtctcgc tcaggcgcaa tcacgaatga ataacggttt    1380
ggttgatgcg agtgattttg atgacgagcg taatggctgg cctgttgaac aagtctggaa    1440
agaaatgcat aaacttttgc cattctcacc ggattcagtc gtcactcatg gtgatttctc    1500
acttgataac cttatttttg acgaggggaa attaataggt tgtattgatg ttggacgagt    1560
cggaatcgca gaccgatacc aggatcttgc catcctatgg aactgcctcg gtgagttttc    1620
tccttcatta cagaaacggc ttttcaaaa atatggtatt gataatcctg atatgaataa    1680
attgcagttt catttgatgc tcgatgagtt tttctaatca gaattggtta attggttgta    1740
acactggcag agcattacgc tgacttgacg ggacggcggc tttgttgaat aaatcgaact    1800
tttgctgagt tgaaggatca gatcacgcat cttcccgaca acgcagaccg ttccgtggca    1860
aagcaaaagt tcaaaatcac caactggtcc acctacaaca aagctctcat caaccgtggc    1920
ggggatcctc tagagtcgac ctgcaggcat gcaagcttca gggttgagat gtgtataaga    1980
gacagactgg tacgtttcct ggaagcggaa gattttgatg cggcgattat cttcgttcgt    2040
accaaaaacg cgactctgga agtggctgaa gctcttgagc gtaacggcta caacagcgcc    2100
gcgctgaacg tgacatgaa ccaggcgctg cgtgaacaga cactggaacg cctgaaagat    2160
ggtcgtctgg acatcctgat tgcgaccgac gttgcagccc gtggcctgga cgttgagcgt    2220
atcagcctgg tagttaacta cgatatcccg atggattctg agtcttacgt tcaccgtatc    2280
ggtcgtaccg gtcgtgcggg tcgtgctggc cgcgcgctgc tgttcgttga gaaccgcgag    2340
cgtcgtctgc tgcgcaacat tgaacgtact atgaagctga ctattccgga agtagaactg    2400
ccgaacgcag aactgctagg caaacgccgt ctggaaaaat cgccgctaa agtacagcag    2460 cagctggaaa gcagcgatct ggatcaatac cgcgcactgc tgagcaaaat tcagccgact    2520
gctgaaggtg aagagctgga tctcgaaact ctggctgcgg cactgctgaa aatggcacag    2580
ggtgaacgta ctctgatcgt accgccagat gcgccgatgc gtccgaaacg tgaattccgt    2640
gaccgtgatg accgtggtcc gcgcgatcgt aacgaccgtg gcccgcgtgg tgaccgtgaa    2700
gatcgtccgc gtcgtgaacg tcgtgatgtt ggcgatatgc agctgtaccg cattgaagtg    2760
ggccgcgatg atggtgttga agttcgtcat atcgttggtg cgattgctaa cgaaggcgac    2820
atcagcagcc gttacattgg taacatcaag ctgtttgctt ctcactccac catcgaactg    2880
ccgaaaggta tgccgggtga agtgctgcaa cactttacgc gcactcgcat tctcaacaag    2940
ccgatgaaca tgcagttact gggcgatgca cagccgcata ctggcggtga gcgtcgtggc    3000
ggtggtcgtg gtttcggtgg cgaacgtcgt gaaggcggtc gtaacttcag cggtgaacgc    3060
cgtgaaggtg gccgtggtga tggtcgtcgt tttagcggcg aacgtcgtga aggccgcgct    3120
ccgcgtcgtg atgattctac cggtcgtcgt cgtttcggtg gtgatgcgta a             3171
```

<210> SEQ ID NO 37
<211> LENGTH: 2904
<212> TYPE: DNA
<213> ORGANISM: Escherichia coli

<400> SEQUENCE: 37

```
atgactgaat cttttgctca actctttgaa gagtccttaa agaaatcga aaccccgcccg      60 ggttctatcg ttcgtggcgt tgttgttgct atcgacaaag acgtagtact ggttgacgct     120
ggtctgaaat ctgagtccgc catcccggct gagcagttca aaaacgccca gggcgagctg     180
```

-continued

```
gaaatccagg taggtgacga agttgacgtt gctctggacg cagtagaaga cggcttcggt    240
gaaactctgc tgtcccgtga aaagctaaa cgtcacgaag cctggatcac gctggaaaaa    300
gcttacgaag atgctgaaac tgttaccggt gttatcaacg gcaaagttaa gggcggcttc    360
actgttgagc tgaacggtat tcgtgcgttc ctgccaggtt ctctggtaga cgttcgtccg    420
gtgcgtgaca ctctgcacct ggaaggcaaa gagcttgaat ttaaagtaat caagctggat    480
cagaagcgca caacgttgt tgtttctcgt cgtgccgtta tcgaatccga aaacagcgca    540
gagcgcgatc agctgctgga aaacctgcag gaaggcatgg aagttaaagg tatcgttaag    600
aacctcactg actacggtgc attcgttgat ctgggcggcg ttgacggcct gctgcacatc    660
actgacatgg cctggaaacg cgttaagcat ccgagcgaaa tcgtcaacgt gggcgacgaa    720
atcactgtta aagtgctgaa gttcgaccgc gaacgtaccc gtgtatccct gggcctgaaa    780
cagctgggcg aagatccgtg gtagctatc gctaaacgtt atccggaagg taccaaactg    840
actggtcgcg tgaccaacct gaccgactac ggctgcttcg ttgaaatcga agaaggcgtt    900
gaaggcctgg tacacgtttc cgaaatggac tggaccaaca aaaacatcca cccgtccaaa    960
gttgttaacg ttggcgatgt agtggaagtt atggttctgg atatcgacga agaacgtcgt   1020
cgtatctccc tgggtctgaa acagtgcaaa gctaacccgt ggcagcagtt cgcggaaacc   1080
cacaacaagg gcgaccgtgt tgaaggtaaa atcaagtcta tcactgactt cggtatcttc   1140
atcggcttgg acggcggcat cgacggcctg gttcacctgt ctgacatctc ctggaacgtt   1200
gcaggcgaag aagcagttcg tgaatacaaa aaaggcgacg aaatcgctgc agttgttctg   1260
caggttgacg cagaacgtga acgtatctcc ctgggcgtta aacagctcgc agaagatccg   1320
ttcaacaact gggttgctct gaacaagaaa ggcgctatcg taaccggtaa agtaactgca   1380
gttgacgcta aaggcgcaac cgtagaactg gctgacggcg ttgaaggtta cctgcgtgct   1440
tctgaagcat cccgtgaccg cgttgaagac gctaccctgg ttctgagcgt tggcgacgaa   1500
gttgaagcta aattcaccgg cgttgatcgt aaaaaccgcg caatcagcct gtctgttcgt   1560
gcgaaagacg aagctgacga gaaagatgca atcgcaactg tctcttatac acatctcaac   1620
cctgaagctt gcatgcctgc aggtcgactc tagaggatcc ccgccacggt tgatgagagc   1680
tttgttgtag gtggaccagt tggtgatttt gaacttttgc tttgccacgg aacggtctgc   1740
gttgtcggga agatgcgtga tctgatcctt caactcagca aaagttcgat ttattcaaca   1800
aagccgccgt cccgtcaagt cagcgtaatg ctctgccagt gttacaacca attaaccaat   1860
tctgattaga aaaactcatc gagcatcaaa tgaaactgca atttattcat atcaggatta   1920
tcaataccat attttgaaa aagccgtttc tgtaatgaag gagaaaactc accgaggcag   1980
ttccatagga tggcaagatc ctggtatcgg tctgcgattc cgactcgtcc aacatcaata   2040
caacctatta atttccctc gtcaaaaata aggttatcaa gtgagaaatc accatgagtg   2100
acgactgaat ccggtgagaa tggcaaaagt ttatgcattt ctttccagac ttgttcaaca   2160
ggccagccat tacgctcgtc atcaaaatca ctcgcatcaa ccaaaccgtt attcattcgt   2220
gattgcgcct gagcgagacg aaatacgcga tcgctgttaa aaggacaatt acaaacagga   2280
atcgaatgca accggcgcag gaacactgcc agcgcatcaa caatatttc acctgaatca   2340 ggatattctt ctaatacctg gaatgctgtt tttccgggga tcgcagtggt gagtaaccat   2400
gcatcatcag gagtacggat aaaatgcttg atggtcggaa gaggcataaa ttccgtcagc   2460
cagtttagtc tgaccatctc atctgtaaca tcattggcaa cgctacctt gccatgtttc   2520
```

| | |
|---|---:|
| agaaacaact ctggcgcatc gggcttccca tacaatcgat agattgtcgc acctgattgc | 2580 |
| ccgacattat cgcgagccca tttatacccca tataaatcag catccatgtt ggaatttaat | 2640 |
| cgcggcctcg agcaagacgt ttcccgttga atatggctca taacaccect tgtattactg | 2700 |
| tttatgtaag cagacagttt tattgttcat gatgatatat ttttatcttg tgcaatgtaa | 2760 |
| catcagagat tttgagacac aattcatcga tgatggttga gatgtgtata agagacagca | 2820 |
| atcgcaactg ttaacaaaca ggaagatgca aacttctcca caacgcaat ggctgaagct | 2880 |
| ttcaaagcag ctaaaggcga gtaa | 2904 |

<210> SEQ ID NO 38
<211> LENGTH: 5454
<212> TYPE: DNA
<213> ORGANISM: Escherichia coli

<400> SEQUENCE: 38

| | |
|---|---:|
| gtgaaagatt tattaaagtt tctgaaagcg cagactaaaa ccgaagagtt tgatgcgatc | 60 |
| aaaattgctc tggcttcgcc agacatgatc cgttcatggt ctttcggtga agttaaaaag | 120 |
| ccggaaacca tcaactaccg tacgttcaaa ccagaacgtg acggccttt ctgcgcccgt | 180 |
| atctttgggc cggtaaaaga ttacgagtgc ctgtgcggta agtacaagcg cctgaaacac | 240 |
| cgtggcgtca tctgtgagaa gtgcggcgtt gaagtgaccc agactaaagt acgccgtgag | 300 |
| cgtatgggcc acatcgaact ggcttccccg actgcgcaca tctggttcct gaaatcgctg | 360 |
| ccgtcccgta tcggtctgct gctcgatatg ccgctgcgcg atatcgaacg cgtactgtac | 420 |
| tttgaatcct atgtggttat cgaaggcggt atgaccaacc tggaacgtca gcagatcctg | 480 |
| actgaagagc agtatctgga cgcgctggaa gagttcggtg acgaattcga cgcgaagatg | 540 |
| ggggcggaag caatccaggc tctgctgaag agcatggatc tggagcaaga gtgcgaacag | 600 |
| ctgcgtgaag agctgaacga aaccaactcc gaaaccaagc gtaaaaagct gaccaagcgt | 660 |
| atcaaactgc tggaagcgtt cgttcagtct ggtaacaaac cagagtggat gatcctgacc | 720 |
| gttctgccgg tactgccgcc agatctgcgt ccgctggttc cgctggatgg tggtcgtttc | 780 |
| gcgacttctg acctgaacga tctgtatcgt cgcgtcatta accgtaacaa ccgtctgaaa | 840 |
| cgtctgctgg atctggctgc gccggacatc atcgtacgta acgaaaaacg tatgctgcag | 900 |
| gaagcggtag acgccctgct ggataacggt cgtcgcggtc gtgcgatcac cggttctaac | 960 |
| aagcgtcctc tgaaatcttt ggccgacatg atcaaaggta acagggtcg tttccgtcag | 1020 |
| aacctgctcg gtaagcgtgt tgactactcc ggtcgttctg taatcaccgt aggtccatac | 1080 |
| ctgcgtctgc atcagtgcgg tctgccgaag aaaatggcac tggagctgtt caaaccgttc | 1140 |
| atctacggca agtggaact gcgtggtctt gctaccacca ttaaagctgc gaagaaaatg | 1200 |
| gttgagcgcg aagaagctgt cgtttgggat atcctggacg aagttatccg cgaacacccg | 1260 |
| gtactgctga accgtgcacc gactctgcac cgtctgggta tccaggcatt tgaaccggta | 1320 |
| ctgatcgaag gtaaagctat ccagctgcac ccgctggttt gtgcggcata taacgccgac | 1380 |
| ttcgatggtg accagatggc tgttcacgta ccgctgacgc tggaagccca gctggaagcg | 1440 |
| cgtgcgctga tgatgtctac caacaacatc ctgtccccgg cgaacggcga accaatcatc | 1500 |
| gttccgtctc aggacgttgt actgggtctg tactacatga cccgtgactg tgttaacgcc | 1560 |
| aaaggcgaag gcatggtgct gactggcccg aaagaagcag aacgtctgta cgctctggt | 1620 |
| ctggcttctc tgcatgcgcg cgttaaagtg cgtatcaccg agtatgaaaa agatgctaac | 1680 |
| ggtgaattag tagcgaaaac cagcctgaaa gacacgactg ttggccgtgc cattctgtgg | 1740 |

-continued

| | |
|---|---|
| atgattgtac cgaaaggtct gccttactcc atcgtcaacc aggcgctggg taaaaaagca | 1800 |
| atctccaaaa tgctgaacac ctgctaccgc attctcggtc tgaaaccgac cgttattttt | 1860 |
| gcggaccaga tcatgtacac cggcttcgcc tatgcagcgc gttctggtgc atctgttggt | 1920 |
| atcgatgaca tggtcatccc ggagaagaaa cacgaaatca tctccgaggc agaagcagaa | 1980 |
| gttgctgaaa ttcaggagca gttccagtct ggtctggtaa ctgcgggcga acgctacaac | 2040 |
| aaagttatcg atatctgggc tgcggcgaac gatcgtgtat ccaaagcgat gatggataac | 2100 |
| ctgcaaactg aaaccgtgat taaccgtgac ggtcaggaag agaagcaggt ttccttcaac | 2160 |
| agcatctaca tgatggccga ctccggtgcg cgtggttctg cggcacagat tcgtcagctt | 2220 |
| gctggtatgc gtggtctgat ggcgaagccg atggctcca tcatcgaaac gccaatcacc | 2280 |
| gcgaacttcc gtgaaggtct gaacgtactc cagtacttca tctccaccca cggtgctcgt | 2340 |
| aaaggtctgg cggataccgc actgaaaact gcgaactccg gttacctgac tcgtcgtctg | 2400 |
| gttgacgtgg cgcaggacct ggtggttacc gaagacgatt gtggtaccca tgaaggtatc | 2460 |
| atgatgactc cggttatcga gggtggtgac gttaaagagc cgctgcgcga tcgcgtactg | 2520 |
| ggtcgtgtaa ctgctgaaga cgttctgaag ccgggtactg ctgatatcct cgttccgcgc | 2580 |
| aacacgctgc tgcacgaaca gtggtgtgac ctgctggaag agaactctgt cgacgcggtt | 2640 |
| aaagtacgtt ctgttgtatc ttgtgacacc gactttggtg tatgtgcgca ctgctacggt | 2700 |
| cgtgacctgg cgcgtggcca catcatcaac aagggtgaag caatcggtgt tatcgcggca | 2760 |
| cagtccatcg gtgaaccggg tacacagctg accatgcgta cgttccacat cggtggtgcg | 2820 |
| gcatctcgtg cggctgctga atccagcatc caagtgaaaa acaaaggtag catcaagctc | 2880 |
| agcaacgtga agtcggttgt gaactccagc ggtaaactgg ttatcacttc ccgtaatact | 2940 |
| gaactgaaac tgatcgacga attcggtcgt actaaagaaa gctacaaagt accttacggt | 3000 |
| gcggtactgg cgaaaggcga tggcgaacag gttgctggcg gcgaaaccgt tgcaaactgg | 3060 |
| gacccgcaca ccatgccggt tatcaccgaa gtaagcggtt ttgtacgctt tactgacatg | 3120 |
| atcgacggcc agaccattac gcgtcagacc gacgaactga ccggtctgtc ttcgctggtg | 3180 |
| gttctggatt ccgcagaacg taccgcaggt ggtaaagatc tgcgtccggc actgaaaatc | 3240 |
| gttgatgctc agggtaacga cgttctgatc ccaggtaccg atatgccagc gcagtacttc | 3300 |
| ctgccgggta agcgattgt tcagctggaa gatggcgtac agatcagctc tggtgacacc | 3360 |
| ctggcgcgta ttccgcagga atccggcggt accaaggaca tcaccggtgg tctgccgcgc | 3420 |
| gttgcggacc tgttcgaagc acgtcgtccg aaagagccgg caatcctggc tgaaatcagc | 3480 |
| ggtatcgttt ccttcggtaa agaaaccaaa ggtaaacgtc gtctggttat caccccggta | 3540 |
| gacggtagcg atccgtacga agagatgatt ccgaaatggc gtcagctcaa cgtgttcgaa | 3600 |
| ggtgaacgtg tagaacgtgg tgacgtaatt tccgacggtc cggaagcgcc gcacgacatt | 3660 |
| ctgcgtctgc gtggtgttca tgctgttact cgttacatcg ttaacgaagt acaggacgta | 3720 |
| taccgtctgc agggcgttaa gattaacgat aaacacatcg aagttatcgt tcgtcagatg | 3780 |
| ctgcgtaaag ctaccatcgt taacgcgggt agctccgact tcctggaagg cgaacaggtt | 3840 |
| gaatactctc gcgtcaagat cgcaaaccgc gaactggaag cgaacggcaa agtgggtgca | 3900 |
| acttactccc gcgatctgct gggtatcacc aaagcgtctc tggcaaccga gtccttcatc | 3960 |
| tccgcggcat cgttccagga gaccactcgc gtgctgaccg aagcagccgt tgcgggcaaa | 4020 |
| cgcgacgaac tgcgcggcct gaaagagaac gttatcgtgg gtcgtctgat cccggcaggt | 4080 |

```
accggttacg cgtaccacca ggatcgtatg cgtcgccgtg ctgcgggtga agctctgtct    4140
cttatacaca tctcaaccct gaagcttgca tgcctgcagg tcgactctag aggatccccg    4200
ccacggttga tgagagcttt gttgtaggtg gaccagttgg tgattttgaa cttttgcttt    4260
gccacggaac ggtctgcgtt gtcgggaaga tgcgtgatct gatccttcaa ctcagcaaaa    4320
gttcgattta ttcaacaaag ccgccgtccc gtcaagtcag cgtaatgctc tgccagtgtt    4380
acaaccaatt aaccaattct gattagaaaa actcatcgag catcaaatga aactgcaatt    4440
tattcatatc aggattatca ataccatatt tttgaaaaag ccgtttctgt aatgaaggag    4500
aaaactcacc gaggcagttc cataggatgg caagatcctg gtatcggtct gcgattccga    4560
ctcgtccaac atcaatacaa cctattaatt tcccctcgtc aaaataagg ttatcaagtg     4620 agaaatcacc atgagtgacg actgaatccg gtgagaatgg caaaagttta tgcatttctt    4680
tccagacttg ttcaacaggc cagccattac gctcgtcatc aaaatcactc gcatcaacca    4740
aaccgttatt cattcgtgat tgcgcctgag cgagacgaaa tacgcgatcg ctgttaaaag    4800
gacaattaca acaggaatc gaatgcaacc ggcgcaggaa cactgccagc gcatcaacaa     4860
tattttcacc tgaatcagga tattcttcta atacctggaa tgctgttttt ccggggatcg    4920
cagtggtgag taaccatgca tcatcaggag tacggataaa atgcttgatg gtcggaagag    4980
gcataaattc cgtcagccag tttagtctga ccatctcatc tgtaacatca ttggcaacgc    5040
tacctttgcc atgtttcaga acaactctg gcgcatcggg cttcccatac aatcgataga     5100
ttgtcgcacc tgattgcccg acattatcgc gagcccattt ataccatat aaatcagcat     5160 ccatgttgga atttaatcgc ggcctcgagc aagacgtttc ccgttgaata tggctcataa    5220
caccccttgt attactgttt atgtaagcag acagttttat tgttcatgat gatatatttt    5280
tatcttgtgc aatgtaacat cagagatttt gagacacaat tcatcgatga tggttgagat    5340
gtgtataaga gacagggtga agctccggct gcaccgcagg tgactgcaga agacgcatct    5400
gccagcctgg cagaactgct gaacgcaggt ctgggcggtt ctgataacga gtaa          5454
```

<210> SEQ ID NO 39
<211> LENGTH: 1845
<212> TYPE: DNA
<213> ORGANISM: Escherichia coli

<400> SEQUENCE: 39

```
atgggcaaaa catctatgat acacgcaatt gtggatcaat atagtcactg tgaatgggtg      60
gaaaatagca tgagtgccaa tgaaaacaac ctgatttgga tcgatcttga gatgaccggt     120
ctggatcccg agcgcgatcg cattattgag attgccacgc tggtgaccga tgccaacctg     180
aatattctgg cagaagggcc gaccattgca gtacaccagt ctgatgaaca gctggcgctg     240
atggatgact ggaacgtgcg cacccatacc gccagcgggc tggtagagcg cgtgaaagcg     300
agcacgatgg gcgatcggga agctgaactg caacgctcg aatttttaaa acagtgggtg      360
cctgcgggaa aatcgccgat tgcggtaac agcatcggtc aggaccgtcg tttcctgttt      420
aaatacatgc cggagctgga agcctacttc cactaccgtt atctcgatgt cagcaccctg     480
aaagagctgg cgcgccgctg aagccggaa attctggatg gttttaccaa gcaggggacg      540
catcaggcga tggatgatat ccgtgaatcg gtggcggagc tggcttacta cctgtctctt     600
atacacatct caaccctgaa gcttgcatgc ctgcaggtcg actctagagg atccccgcca     660
cggttgatga gagcttttgtt gtaggtggac cagttggtga ttttgaactt ttgctttgcc    720
acggaacggt ctgcgttgtc gggaagatgc gtgatctgat ccttcaactc agcaaaagtt    780
```

```
cgatttattc aacaaagccg ccgtcccgtc aagtcagcgt aatgctctgc cagtgttaca      840
accaattaac caattctgat tagaaaaact catcgagcat caaatgaaac tgcaatttat      900
tcatatcagg attatcaata ccatattttt gaaaaagccg tttctgtaat gaaggagaaa      960
actcaccgag gcagttccat aggatggcaa gatcctggta tcggtctgcg attccgactc     1020
gtccaacatc aatacaacct attaatttcc cctcgtcaaa ataaggttta tcaagtgaga     1080
aatcaccatg agtgacgact gaatccggtg agaatggcaa aagtttatgc atttctttcc     1140
agacttgttc aacaggccag ccattacgct cgtcatcaaa atcactcgca tcaaccaaac     1200
cgttattcat tcgtgattgc gcctgagcga gacgaaatac gcgatcgctg ttaaaaggac     1260
aattacaaac aggaatcgaa tgcaaccggc gcaggaacac tgccagcgca tcaacaatat     1320
tttcacctga atcaggatat tcttctaata cctggaatgc tgttttccg gggatcgcag      1380 tggtgagtaa ccatgcatca tcaggagtac ggataaaatg cttgatggtc ggaagaggca     1440
taaattccgt cagccagttt agtctgacca tctcatctgt aacatcattg gcaacgctac     1500 cttgccatg  tttcagaaac aactctggcg catcgggctt cccatacaat cgatagattg     1560
tcgcacctga ttgcccgaca ttatcgcgag cccatttata cccatataaa tcagcatcca     1620
tgttggaatt taatcgcggc ctcgagcaag acgtttcccg ttgaatatgg ctcataacac     1680
cccttgtatt actgtttatg taagcagaca gtttttattgt tcatgatgat atattttat    1740 cttgtgcaat gtaacatcag agattttgag acacaattca tcgatgatgg ttgagatgtg     1800
tataagagac aggcttacta ccgcgagcat tttatcaagc tgtaa                     1845

<210> SEQ ID NO 40
<211> LENGTH: 2334
<212> TYPE: DNA
<213> ORGANISM: Escherichia coli

<400> SEQUENCE: 40
atgaagccaa ttttagccg  tggcccgtcg ctacagattc gccttattct ggcggtgctg       60
gtggcgctcg gcattattat tgccgacagc cgcctgggga cgttcagtca atccgtact      120 tatatggata ccgccgtcag tcctttctac tttgtttcca atgctcctcg tgaattgctg     180
gatggcgtat cgcagacgct ggcctcgcgt gaccaattag aacttgaaaa ccgggcgtta     240
cgtcaggaac tgttgctgaa aaacagtgaa ctgctgatgc ttgacaata  caaacaggag     300 aacgcgcgtc tgcgcgagct gctgggttcc ccgctgcgtc aggatgagca gaaaatggtg     360
actcaggtta tctccacggt taacgatcct tatagcgatc aagttgttat cgataaaggt     420
agcgttaatg gcgtttatga aggccagccg gtcatcagcg acaaaggtgt tgttggtcag     480
gtggtggccg tcgctaaact gaccagtcgc gtgctgctga tttgtgatgc gacccacgcg     540
ctgccaatcc aggtgctgcg caacgatatc gcgtaattg  cagccggtaa cggttgtacg     600
gatgatttgc agcttgagca tctgccggcg aatacggata ttcgtgttgg tgatgtgctg     660
gtgacttccg gtctgggcgg tcgtttcccg gaaggctatc cggtcgcggt tgtctcttcc     720
gtaaaactcg atacccagcg cgcttatact gtgattcagg cgcgtccgac tgcagggctg     780
caacgtttgc gttatctgct gctgctgtgg gggcagatc  gtaacggcgc taacccgatg     840
acgccggaag aggtgcatcg tgttgctaat gaacgtctga tgcagatgat gccgcaggta     900
ttgccttcgc cagacgcgat ggggccaaag ttacctgaac cggcaacggg gatcgctcag     960
ccgactccgc agcaaccggc gacaggaaat gcagctactg cgcctgctgc gccgacacag    1020
```

-continued

```
cctctgtctc ttatacacat ctcaaccatc atcgatgaat tgtgtctcaa aatctctgat        1080
gttacattgc acaagataaa aatatatcat catgaacaat aaaactgtct gcttacataa        1140
acagtaatac aagggtgtt atgagccata ttcaacggga acgtcttgc tcgaggccgc         1200 gattaaattc caacatggat gctgatttat atgggtataa atgggctcgc gataatgtcg        1260
ggcaatcagg tgcgacaatc tatcgattgt atgggaagcc cgatgcgcca gagttgtttc        1320
tgaaacatgg caaaggtagc gttgccaatg atgttacaga tgagatggtc agactaaact        1380
ggctgacgga atttatgcct cttccgacca tcaagcattt tatccgtact cctgatgatg        1440
catggttact caccactgcg atccccggaa aaacagcatt ccaggtatta agaatatc          1500 ctgattcagg tgaaaatatt gttgatgcgc tggcagtgtt cctgcgccgg ttgcattcga        1560
ttcctgtttg taattgtcct tttaacagcg atcgcgtatt tcgtctcgct caggcgcaat        1620
cacgaatgaa taacggtttg gttgatgcga gtgattttga tgacgagcgt aatggctggc        1680
ctgttgaaca agtctggaaa gaaatgcata acttttgcc attctcaccg gattcagtcg         1740
tcactcatgg tgatttctca cttgataacc ttatttttga cgaggggaaa ttaataggtt        1800
gtattgatgt tggacgagtc ggaatcgcag accgatacca ggatcttgcc atcctatgga       1860
actgcctcgg tgagttttct ccttcattac agaaacggct ttttcaaaaa tatggtattg        1920
ataatcctga tatgaataaa ttgcagtttc atttgatgct cgatgagttt ttctaatcag        1980
aattggttaa ttggttgtaa cactggcaga gcattacgct gacttgacgg gacggcggct        2040
ttgttgaata atcgaacttt tgctgagtt gaaggatcag atcacgcatc ttcccgacaa         2100
cgcagaccgt tccgtggcaa agcaaaagtt caaaatcacc aactggtcca cctacaacaa        2160
agctctcatc aaccgtggcg gggatcctct agagtcgacc tgcaggcatg caagcttcag        2220
ggttgagatg tgtataagag acagacacag cctgctgcta atcgctctcc acaaagggct       2280
acgccgccgc aaagtggtgc tcaaccgcct gcgcgtgcgc cgggagggca atag             2334
```

<210> SEQ ID NO 41
<211> LENGTH: 2676
<212> TYPE: DNA
<213> ORGANISM: Escherichia coli

<400> SEQUENCE: 41

```
atgcgaagtg aacagatttc tggctcgtca ctcaatccgt cttgtcgttt cagttcctgt          60
ctcttataca catctcaacc atcatcgatg aattgtgtct caaatctct gatgttacat         120 tgcacaagat aaaaatatat catcatgaac aataaaactg tctgcttaca taacagtaa         180 tacaagggt gttatgagcc atattcaacg ggaaacgtct tgctcgaggc cgcgattaaa         240
ttccaacatg gatgctgatt tatatgggta taatgggc cgcgataatg tcgggcaatc          300
aggtgcgaca atctatcgat tgtatgggaa gcccgatgcg ccagagttgt ttctgaaaca        360
tggcaaaggt agcgttgcca atgatgttac agatgagatg gtcagactaa actggctgac        420
ggaatttatg cctcttccga ccatcaagca ttttatccgt actcctgatg atgcatggtt        480
actcaccact gcgatcccg gaaaaacagc attccaggta ttagaagaat atcctgattc        540
aggtgaaaat attgttgatg cgctggcagt gttcctgcgc cggttgcatt cgattcctgt        600
ttgtaattgt cctttaaca gcgatcgcgt atttcgtctc gctcaggcgc aatcacgaat        660
gaataacggt ttggttgatg cgagtgattt tgatgacgag cgtaatggct ggcctgttga        720
acaagtctgg aaagaaatgc ataaactttt gccattctca ccggattcag tcgtcactca        780
tggtgatttc tcacttgata accttatttt tgacgagggg aaattaatag gttgtattga        840
```

-continued

```
tgttggacga gtcggaatcg cagaccgata ccaggatctt gccatcctat ggaactgcct      900
cggtgagttt tctccttcat tacagaaacg ctttttcaa aaatatggta ttgataatcc      960
tgatatgaat aaaattgcagt ttcatttgat gctcgatgag tttttctaat cagaattggt   1020
taattggttg taacactggc agagcattac gctgacttga cgggacggcg ctttgttga    1080 ataaatcgaa cttttgctga gttgaaggat cagatcacgc atcttcccga caacgcagac   1140
cgttccgtgg caaagcaaaa gttcaaaatc accaactggt ccacctacaa caaagctctc   1200
atcaaccgtg gcggggatcc tctagagtcg acctgcaggc atgcaagctt cagggttgag   1260
atgtgtataa gagacagttt cagttctgcg tactctcctg tgaccaggca gcgaaaagac   1320
atgagtcgat gaccgtaaac aggcatggat gatcctgcca taccattcac aacattaagt   1380
tcgagattta ccccaagttt aagaactcac accactatga atcttaccga attaaagaat   1440
acgccggttt ctgagctgat cactctcggc gaaaatatgg ggctggaaaa cctggctcgt   1500
atgcgtaagc aggacattat ttttgccatc ctgaagcagc acgcaaagag tggcgaagat   1560
atctttggtg atggcgtact ggagatattg caggatggat ttggtttcct ccgttccgca   1620
gacagctcct acctcgccgg tcctgatgac atctacgttt ccctagcca aatccgccgt     1680 ttcaacctcc gcactggtga taccatctct ggtaagattc gcccgccgaa agaaggtgaa   1740
cgctattttg cgctgctgaa agttaacgaa gttaacttcg acaaacctga aaacgccgc     1800 aacaaaatcc tctttgagaa cttaaccccg ctgcacgcaa actctcgtct gcgtatggaa   1860
cgtggtaacg ttctactga agatttaact gctcgcgtac tggatctggc atcacctatc    1920
ggtcgtggtc agcgtggtct gattgtggca ccgccgaaag ccgtaaaaac catgctgctg   1980
cagaacattg ctcagagcat tgcttacaac cacccggatt gtgtgctgat ggttctgctg   2040
atcgacgaac gtccggaaga gtaaccgag atgcagcgtc tggtaaaagg tgaagttgtt    2100
gcttctacct ttgacgaacc cgcatctcgc cacgttcagg ttgcgaaaat ggtgatcgag   2160
aaggccaaac gcctggttga gcacaagaaa gacgttatca ttctgctcga ctccatcact   2220
cgtctggcgc gcgcttacaa caccgttgtt ccggcgtcag gtaaagtgtt gaccggtggt   2280
gtggatgcca acgccctgca tcgtccgaaa cgcttctttg gtgcggcgcg taacgtggaa   2340
gagggcggca gcctgaccat tatcgcgacg gcgcttatcg ataccggttc taaaatggac   2400
gaagttatct acgaagagtt taaaggtaca ggcaacatgg aactgcacct ctctcgtaag   2460
atcgctgaaa aacgcgtctt cccggctatc gactacaacc gttctggtac ccgtaaagaa   2520
gagctgctca cgactcagga agaactgcag aaaatgtgga tcctgcgcaa aatcattcac   2580
ccgatgggcg aaatcgatgc aatggaattc ctcattaata aactggcaat gaccaagacc   2640
aatgacgatt tcttcgaaat gatgaaacgc tcataa                              2676
```

<210> SEQ ID NO 42
<211> LENGTH: 1746
<212> TYPE: DNA
<213> ORGANISM: Escherichia coli

<400> SEQUENCE: 42

```
atggattact tcaccctctt tggcttgcct gcccgctatc aactcgatac ccaggcgctg      60
agcctgcgtt ttcaggatct acaacgtcag tatcatcctg ataaattcgc cagcggaagc     120
caggcggaac aactcgccgc cgtacagcaa tctgcaacca ttaaccaggc ctggcaaacg    180
ctgcgtcatc cgttaatgcg cgcggaatat ttgctttctt tgcacggctt tgatctcgcc    240
```

-continued

```
agcgagcagc atacctgtct cttatacaca tctcaaccat catcgatgaa ttgtgtctca    300
aaatctctga tgttacattg cacaagataa aaatatatca tcatgaacaa taaaactgtc    360
tgcttacata aacagtaata caaggggtgt tatgagccat attcaacggg aaacgtcttg    420
ctcgaggccg cgattaaatt ccaacatgga tgctgattta tatgggtata aatgggctcg    480
cgataatgtc gggcaatcag gtgcgacaat ctatcgattg tatgggaagc ccgatgcgcc    540
agagttgttt ctgaaacatg gcaaaggtag cgttgccaat gatgttacag atgagatggt    600
cagactaaac tggctgacgg aatttatgcc tcttccgacc atcaagcatt ttatccgtac    660
tcctgatgat gcatggttac tcaccactgc gatccccgga aaaacagcat tccaggtatt    720
agaagaatat cctgattcag gtgaaaatat tgttgatgcg ctggcagtgt tcctgcgccg    780
gttgcattcg attcctgttt gtaattgtcc ttttaacagc gatcgcgtat ttcgtctcgc    840
tcaggcgcaa tcacgaatga ataacggttt ggttgatgcg agtgattttg atgacgagcg    900
taatggctgg cctgttgaac aagtctggaa agaaatgcat aaacttttgc cattctcacc    960
ggattcagtc gtcactcatg gtgatttctc acttgataac cttattttg acgaggggaa   1020 attaataggt tgtattgatg ttggacgagt cggaatcgca gaccgatacc aggatcttgc   1080
catcctatgg aactgcctcg gtgagttttc tccttcatta cagaaacggc ttttcaaaa    1140 atatggtatt gataatcctg atatgaataa attgcagttt catttgatgc tcgatgagtt   1200
tttctaatca gaattggtta attggttgta acactggcag agcattacgc tgacttgacg   1260
ggacggcggc tttgttgaat aaatcgaact tttgctgagt tgaaggatca gatcacgcat   1320
cttcccgaca acgcagaccg ttccgtggca aagcaaaagt tcaaaatcac caactggtcc   1380
acctacaaca aagctctcat caaccgtggc ggggatcctc tagagtcgac ctgcaggcat   1440
gcaagcttca gggttgagat gtgtataaga gacaggcagc atactgtgcg cgacaccgcg   1500
ttcctgatgg aacagttgga gctgcgcgaa gagctggacg agatcgaaca ggcgaaagat   1560
gaagcgcggc tggaaagctt tatcaaacgt gtgaaaaaga tgtttgatac ccgccatcag   1620
ttgatggttg aacagttaga caacgagacg tgggacgcgg cggcggatac cgtgcgtaag   1680
ctgcgttttc tcgataaact gcgaagcagt gccgaacaac tcgaagaaaa actgctcgat   1740
ttttaa                                                              1746
```

<210> SEQ ID NO 43
<211> LENGTH: 8609
<212> TYPE: DNA
<213> ORGANISM: Artificial sequence
<220> FEATURE:
<223> OTHER INFORMATION: Reporter plasmid pPCB15

<400> SEQUENCE: 43

```
cgtatggcaa tgaaagacgg tgagctggtg atatgggata gtgttcaccc ttgttacacc     60
gttttccatg agcaaactga aacgttttca tcgctctgga gtgaatacca cgacgatttc    120
cggcagtttc tacacatata ttcgcaagat gtggcgtgtt acggtgaaaa cctggcctat    180
ttccctaaag ggtttattga gaatatgttt ttcgtctcag ccaatccctg ggtgagtttc    240
accagttttg atttaaacgt ggccaatatg gacaacttct tcgcccccgt tttcaccatg    300
ggcaaatatt atacgcaagg cgacaaggtg ctgatgccgc tggcgattca ggttcatcat    360
gccgtctgtg atggcttcca tgtcggcaga atgcttaatg aattacaaca gtactgcgat    420
gagtggcagg gcgggcgta attttttttaa ggcagttatt ggtgcctaga aatatttttat    480 ctgattaata agatgatctt cttgagatcg ttttggtctg cgcgtaatct cttgctctga    540
```

-continued

| | |
|---|---|
| aaacgaaaaa accgccttgc agggcggttt ttcgaaggtt ctctgagcta ccaactcttt | 600 |
| gaaccgaggt aactggcttg gaggagcgca gtcaccaaaa cttgtccttt cagtttagcc | 660 |
| ttaaccggcg catgacttca agactaactc ctctaaatca attaccagtg gctgctgcca | 720 |
| gtggtgcttt tgcatgtctt tccgggttgg actcaagacg atagttaccg gataaggcgc | 780 |
| agcggtcgga ctgaacgggg ggttcgtgca tacagtccag cttggagcga actgcctacc | 840 |
| cggaactgag tgtcaggcgt ggaatgagac aaacgcggcc ataacagcgg aatgacaccg | 900 |
| gtaaaccgaa aggcaggaac aggagagcgc acgagggagc cgccagggga aacgcctggt | 960 |
| atctttatag tcctgtcggg tttcgccacc actgatttga gcgtcagatt tcgtgatgct | 1020 |
| tgtcaggggg gcggagccta tggaaaaacg gctttgccgc ggccctctca cttccctgtt | 1080 |
| aagtatcttc ctggcatctt ccaggaaatc tccgccccgt tcgtaagcca tttccgctcg | 1140 |
| ccgcagtcga acgaccgagc gtagcgagtc agtgagcgag gaagcggaat atatcctgta | 1200 |
| tcacatattc tgctgacgca ccggtgcagc cttttttctc ctgccacatg aagcacttca | 1260 |
| ctgacaccct catcagtgcc aacatagtaa gccagtatat acactccgct agcgcccaat | 1320 |
| acgcaaaccg cctctccccg cgcgttggcc gattcattaa tgcagctggc acgacaggtt | 1380 |
| tcccgactgg aaagcgggca gtgagcgcaa cgcaattaat gtgagttagc tcactcatta | 1440 |
| ggcaccccag gctttacact ttatgcttcc ggctcgtatg ttgtgtggaa ttgtgagcgg | 1500 |
| ataacaattt cacacaggaa acagctatga ccatgattac gaattcgagc tcggtaccca | 1560 |
| aacgaattcg ccctttgac ggtctgcgca aaaaaacacg ttcaccttac tggcatttcg | 1620 |
| gctgagcagt tgctggctga tatcgatagc cgccttgatc agttactgcc ggttcagggt | 1680 |
| gagcgggatt gtgtgggtgc cgcgatgcgt gaaggcacgc tggcaccggg caaacgtatt | 1740 |
| cgtccgatgc tgctgttatt aacagcgcgc gatcttggct gtgcgatcag tcacggggga | 1800 |
| ttactggatt tagcctgcgc ggttgaaatg gtgcatgctg cctcgctgat ctggatgat | 1860 |
| atgccctgca tggacgatgc gcagatgcgt cggggcgtc ccaccattca cacgcagtac | 1920 |
| ggtgaacatg tggcgattct ggcggcggtc gctttactca gcaaagcgtt tggggtgatt | 1980 |
| gccgaggctg aaggtctgac gccgatagcc aaaactcgcg cggtgtcgga gctgtccact | 2040 |
| gcgattggca tgcagggtct ggttcagggc cagtttaagg acctctcgga aggcgataaa | 2100 |
| ccccgcagcg ccgatgccat actgctaacc aatcagttta aaaccagcac gctgttttgc | 2160 |
| gcgtcaacgc aaatgcgtc cattgcggcc aacgcgtcct gcgaagcgcg tgagaacctg | 2220 |
| catcgtttct cgctcgatct cggccaggcc tttcagttgc ttgacgatct taccgatggc | 2280 |
| atgaccgata ccggcaaaga catcaatcag gatgcaggta atcaacgct ggtcaattta | 2340 |
| ttaggctcag gcgcggtcga agaacgcctg cgacagcatt tgcgcctggc cagtgaacac | 2400 |
| ctttccgcgg catgccaaaa cggccattcc accaccaaac ttttattca ggcctggttt | 2460 |
| gacaaaaaac tcgctgccgt cagttaagga tgctgcatga gccattttgc ggtgatcgca | 2520 |
| ccgccctttt tcagccatgt tcgcgctctg caaaaccttg ctcaggaatt agtggcccgc | 2580 |
| ggtcatcgtg ttacgttttt tcagcaacat gactgcaaag cgctggtaac gggcagcgat | 2640 |
| atcggattcc agaccgtcgg actgcaaacg catcctcccg gttccttatc gcacctgctg | 2700 |
| cacctggccg cgcacccact cggaccctcg atgttacgac tgatcaatga aatggcacgt | 2760 |
| accagcgata tgctttgccg ggaactgccc gccgcttttc atgcgttgca gatagagggc | 2820 |
| gtgatcgttg atcaaatgga gccggcaggt gcagtagtcg cagaagcgtc aggtctgccg | 2880 |

-continued

```
tttgtttcgg tggcctgcgc gctgccgctc aaccgcgaac cgggtttgcc tctggcggtg    2940
atgcctttcg agtacggcac cagcgatgcg gctcgggaac gctataccac cagcgaaaaa    3000
atttatgact ggctgatgcg acgtcacgat cgtgtgatcg cgcatcatgc atgcagaatg    3060
ggtttagccc cgcgtgaaaa actgcatcat tgttttctc cactggcaca aatcagccag     3120
ttgatccccg aactggattt tccccgcaaa gcgctgccag actgctttca tgcggttgga    3180
ccgttacggc aaccccaggg gacgccgggg tcatcaactt cttattttcc gtccccggac    3240 aaacccgta ttttgcctc gctgggcacc ctgcagggac atcgttatgg cctgttcagg      3300
accatcgcca aagcctgcga agaggtggat gcgcagttac tgttggcaca ctgtggcggc    3360
ctctcagcca cgcaggcagg tgaactggcc cggggcgggg acattcaggt tgtggatttt    3420
gccgatcaat ccgcagcact ttcacaggca cagttgacaa tcacacatgg tgggatgaat    3480
acggtactgg acgctattgc ttcccgcaca ccgctactgg cgctgccgct ggcatttgat    3540
caacctggcg tggcatcacg aattgtttat catggcatcg gcaagcgtgc gtctcggttt    3600
actaccagcc atgcgctggc gcggcagatt cgatcgctgc tgactaacac cgattacccg    3660
cagcgtatga caaaaattca ggccgcattg cgtctggcag gcggcacacc agccgccgcc    3720
gatattgttg aacaggcgat gcggacctgt cagccagtac tcagtgggca ggattatgca    3780
accgcactat gatctcattc tggtcggtgc cggtctggct aatggcctta tcgcgctccg    3840
gcttcagcaa cagcatccgg atatgcggat cttgcttatt gaggcgggtc ctgaggcggg    3900
agggaaccat acctggtcct ttcacgaaga ggatttaacg ctgaatcagc atcgctggat    3960
agcgccgctt gtggtccatc actggcccga ctaccaggtt cgtttccccc aacgccgtcg    4020
ccatgtgaac agtggctact actgcgtgac ctcccggcat ttcgccggga tactccggca    4080
acagtttgga caacatttat ggctgcatac cgcggtttca gccgttcatg ctgaatcggt    4140
ccagttagcg gatggccgga ttattcatgc cagtacagtg atcgacggac ggggttacac    4200
gcctgattct gcactacgcg taggattcca ggcatttatc ggtcaggagt ggcaactgag    4260
cgcgccgcat ggtttatcgt caccgattat catggatgcg acggtcgatc agcaaaatgg    4320
ctaccgcttt gtttataccc tgccgctttc cgcaaccgca ctgctgatcg aagacacaca    4380
ctacattgac aaggctaatc ttcaggccga acgggcgcgt cagaacattc gcgattatgc    4440
tgcgcgacag ggttggccgt tacagacgtt gctgcgggaa gaacagggtg cattgcccat    4500
tacgttaacg ggcgataatc gtcagttttg gcaacagcaa ccgcaagcct gtagcggatt    4560
acgcgccggg ctgtttcatc cgacaaccgg ctactcccta ccgctcgcgg tggcgctggc    4620
cgatcgtctc agcgcgctgg atgtgtttac ctcttcctct gttcaccaga cgattgctca    4680 cttttgcccag caacgttggc agcaacaggg ttttttccgc atgctgaatc gcatgttgtt    4740
tttagccgga ccggccgagt cacgctggcg tgtgatgcag cgtttctatg cttacccga    4800 ggatttgatt gcccgcttt tatgcgggaaa actcaccgtg accgatcggc tacgcattct    4860
gagcggcaag ccgcccgttc ccgttttcgc ggcattgcag gcaattatga cgactcatcg    4920
ttgaagagcg actacatgaa accaactacg gtaattggtg cgggctttgg tggcctggca    4980
ctggcaattc gtttacaggc cgcaggtatt cctgttttgc tgcttgagca gcgcgacaag    5040
ccgggtggcc gggcttatgt ttatcaggag cagggcttta cttttgatgc aggccctacc    5100
gttatcaccg atcccagcgc gattgaagaa ctgtttgctc tggccggtaa acagcttaag    5160
gattacgtcg agctgttgcc ggtcacgccg ttttatcgcc tgtgctggga gtccggcaag    5220
gtcttcaatt acgataacga ccaggcccag ttagaagcgc agatacagca gttaatccg    5280
```

```
cgcgatgttg cgggttatcg agcgttcctt gactattcgc gtgccgtatt caatgagggc    5340
tatctgaagc tcggcactgt gccttttta tcgttcaaag acatgcttcg ggccgcgccc      5400
cagttggcaa agctgcaggc atggcgcagc gtttacagta aagttgccgg ctacattgag    5460
gatgagcatc ttcggcaggc gttttctttt cactcgctct tagtgggggg gaatccgttt   5520
gcaacctcgt ccatttatac gctgattcac gcgttagaac gggaatgggg cgtctggttt   5580
ccacgcggtg aaccggtgc gctggtcaat ggcatgatca agctgtttca ggatctgggc    5640
ggcgaagtcg tgcttaacgc ccgggtcagt catatgaaaa ccgttgggga caagattcag   5700
gccgtgcagt tggaagacgg cagacggttt gaaacctgcg cggtggcgtc gaacgctgat   5760
gttgtacata cctatcgcga tctgctgtct cagcatcccg cagccgctaa gcaggcgaaa   5820
aaactgcaat ccaagcgtat gagtaactca ctgtttgtac tctattttgg tctcaaccat   5880
catcacgatc aactcgccca tcataccgtc tgttttgggc cacgctaccg tgaactgatt    5940
cacgaaattt ttaaccatga tggtctggct gaggattttt cgctttattt acacgcacct    6000
tgtgtcacgg atccgtcact ggcaccggaa gggtgcggca gctattatgt gctggcgcct   6060
gttccacact taggcacggc gaacctcgac tgggcggtag aaggaccccg actgcgcgat   6120 cgtattttg actaccttga gcaacattac atgcctggct tgcgaagcca gttggtgacg     6180
caccgtatgt ttacgccgtt cgatttccgc gacgagctca atgcctggca aggttcggcc   6240
ttctcggttg aacctattct gacccagagc gcctggttcc gaccacataa ccgcgataag   6300
cacattgata atctttatct ggttggcgca ggcacccatc ctggcgcggg cattcccggc    6360
gtaatcggct cggcgaaggc gacggcaggc ttaatgctgg aggacctgat ttgacgaata   6420
cgtcattact gaatcatgcc gtcgaaacca tggcggttgg ctcgaaaagc tttgcgactg   6480
catcgacgct tttcgacgcc aaaacccgtc gcagcgtgct gatgctttac gcatggtgcc   6540
gccactgcga cgacgtcatt gacgatcaaa cactgggctt tcatgccgac cagccctctt    6600
cgcagatgcc tgagcagcgc ctgcagcagc ttgaaatgaa aacgcgtcag gcctacgccg   6660
gttcgcaaat gcacgagccc gcttttgccg cgtttcagga ggtcgcgatg gcgcatgata   6720
tcgctcccgc ctacgcgttc gaccatctgg aaggttttgc catggatgtg cgcgaaacgc    6780
gctacctgac actggacgat acgctgcgtt attgctatca cgtcgccggt gttgtgggcc   6840
tgatgatggc gcaaattatg ggcgttcgcg ataacgccac gctcgatcgc gcctgcgatc   6900
tcgggctggc tttccagttg accaacattg cgcgtgatat tgtcgacgat gctcaggtgg   6960
gccgctgtta tctgcctgaa agctggctgg aagaggaagg actgacgaaa gcgaattatg   7020
ctgcgccaga aaaccggcag gccttaagcc gtatcgccgg gcgactggta cgggaagcgg   7080
aaccctatta cgtatcatca atggccggtc tggcacaatt acccttacgc tcggcctggg   7140
ccatcgcgac agcgaagcag gtgtaccgta aaattggcgt gaaagttgaa caggccggta   7200
agcaggcctg ggatcatcgc cagtccacgt ccaccgccga aaaattaacg cttttgctga   7260
cggcatccgg tcaggcagtt acttcccgga tgaagacgta tccacccgt cctgctcatc     7320 tctggcagcg cccgatctag ccgcatgcct ttctctcagc gtcgcctgaa gtttagataa   7380
cggtggcgcg tacagaaaac caaaggacac gcagccctct tttcccctta cagcatgatg   7440
catacggtgg gccatgtata accgtttcag gtagcctttg cgcggtatgt agcggaacgg   7500
ccagcgctgg tgtaccagtc cgtcgtggac cataaaatac agtaaaccat aagcggtcat    7560
gcctgcacca atccactgga gcggccagat tcctgtactg ccgaagtaaa tcaggcaat    7620
```

```
cgacacaatg gcgaatacca cggcatagag atcgttaact tcaaatgcgc ctttacgcgg    7680
ttcatgatgt gaaagatgcc agccccaacc ccagccgtgc atgatgtatt tatgtgccag    7740
tgcagcaacc acttccatgc cgaccacggt gacaaacacg atcagggcat tccaaatcca    7800
caacataatt tctcaagggc gaattcgcgg ggatcctcta gagtcgacct gcaggcatgc    7860
aagcttggca ctggccgtcg ttttacaacg tcgtgactgg gaaaaccctg gcgttaccca    7920
acttaatcgc cttgcagcac atcccccttt cgccagctgg cgtaatagcg aagaggcccg    7980
caccgatcgc ccttcccaac agttgcgcag cctgaatggc gaatggcgct gatgtccggc    8040
ggtgcttttg ccgttacgca ccaccccgtc agtagctgaa caggagggac agctgataga    8100
aacagaagcc actggagcac ctcaaaaaca ccatcataca ctaaatcagt aagttggcag    8160
catcacccga cgcactttgc gccgaataaa tacctgtgac ggaagatcac ttcgcagaat    8220
aaataaatcc tggtgtccct gttgataccg ggaagccctg ggccaacttt tggcgaaaat    8280
gagacgttga tcggcacgta agaggttcca actttcacca taatgaaata agatcactac    8340
cgggcgtatt ttttgagtta tcgagatttt caggagctaa ggaagctaaa atggagaaaa    8400
aaatcactgg atataccacc gttgatatat cccaatggca tcgtaaagaa cattttgagg    8460
catttcagtc agttgctcaa tgtacctata accagaccgt tcagctggat attacggcct    8520
ttttaaagac cgtaaagaaa aataagcaca agttttatcc ggcctttatt cacattcttg    8580
cccgcctgat gaatgctcat ccggaattt                                      8609
```

MUTATIONS AFFECTING CAROTENOID PRODUCTION

This application claims the benefit of U.S. Provisional Application No. 60/435,612 filed Dec. 19, 2002.

FIELD OF THE INVENTION

This invention is in the field of microbiology. More specifically, this invention pertains to gene mutations which affect carotenoid production levels in microorganisms.

BACKGROUND OF THE INVENTION

Carotenoids are pigments that are ubiquitous throughout nature and synthesized by all oxygen evolving photosynthetic organisms, and in some heterotrophic growing bacteria and fungi. Industrial uses of carotenoids include pharmaceuticals, food supplements, electro-optic applications, animal feed additives, and colorants in cosmetics, to mention a few.

Because animals are unable to synthesize carotenoids de novo, they must obtain them by dietary means. Thus, manipulation of carotenoid production and composition in plants or bacteria can provide new or improved sources for carotenoids.

Carotenoids come in many different forms and chemical structures. Most naturally-occurring carotenoids are hydrophobic tetraterpenoids containing a $C_{40}$ methyl-branched hydrocarbon backbone derived from successive condensation of eight $C_5$ isoprene units (isopentenyl pyrophosphate, IPP). In addition, novel carotenoids with longer or shorter backbones occur in some species of nonphotosynthetic bacteria. The term "carotenoid" actually includes both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids are furthermore described as being acyclic, monocyclic, or bicyclic depending on whether the ends of the hydrocarbon backbones have been cyclized to yield aliphatic or cyclic ring structures (G. Armstrong, (1999) In Comprehensive Natural Products Chemistry, Elsevier Press, volume 2, pp 321–352).

The genetics of carotenoid pigment biosynthesis are well known (Armstrong et al., *J. Bact.*, 176: 4795–4802 (1994); *Annu. Rev. Microbiol.* 51:629–659 (1997)). This pathway is extremely well studied in the Gram-negative, pigmented bacteria of the genera Pantoea, formerly known as Erwinia. In both *E. herbicola* EHO-10 (ATCC 39368) and *E. uredovora* 20D3 (ATCC 19321), the crt genes are clustered in two operons, crt Z and crt EXYIB (U.S. Pat. No. 5,656,472, U.S. Pat. No. 5,545,816, U.S. Pat. No. 5,530,189, U.S. Pat. No. 5,530,188, and U.S. Pat. No. 5,429,939). Despite the similarity in operon structure, the DNA sequences of *E. uredovora* and *E. herbicola* crt genes show no homology by DNA-DNA hybridization (U.S. Pat. No. 5,429,939,).

The building block for carotenoids, IPP, is an isoprenoid. Isoprenoids constitute the largest class of natural products in nature, and serve as precursors for sterols (eukaryotic membrane stabilizers), gibberelinns and abscisic acid (plant hormones), menaquinone, plastoquinones, and ubiquinone (used as carriers for electron transport), as well as carotenoids and the phytol side chain of chlorophyll (pigments for photosynthesis). All isoprenoids are synthesized via a common metabolic precursor, isopentenyl pyrophosphate (IPP). Until recently, the biosynthesis of IPP was generally assumed to proceed exclusively from acetyl-CoA via the classical mevalonate pathway. However, the existence of an alternative mevalonate-independent pathway for IPP formation has been characterized for eubacteria and a green alga. *E. coli* contain genes that encode enzymes of the mevalonate-independent pathway of isoprenoid biosynthesis (FIG. 1). In this pathway, isoprenoid biosynthesis starts with the condensation of pyruvate with glyceraldehyde-3-phosphate (G3P) to form deoxy-D-xylulose via the enzyme encoded by the dxs gene. A host of additional enzymes are then used in subsequent sequential reactions, converting deoxy-D-xylulose to the final C5 isoprene product, isopentenyl pyrophosphate (IPP). IPP is converted to the isomer dimethylallyl pyrophophate (DMAPP) via the enzyme encoded by the idi gene. IPP is condensed with DMAPP to form C10 geranyl pyrophosphate (GPP) which is then elongated to C15 farnesyl pyrophosphate (FPP).

FPP synthesis is common in both carotenogenic and non-carotenogenic bacteria. *E. coli* do not normally contain the genes necessary for conversion of FPP to β-carotene (FIG. 1). Enzymes in the subsequent carotenoid pathway used to generate carotenoid pigments from FPP precursor can be divided into two categories: carotene backbone synthesis enzymes and subsequent modification enzymes. The backbone synthesis enzymes include geranyl geranyl pyrophosphate synthase (CrtE), phytoene synthase (CrtB), phytoene dehydrogenase (CrtI), and lycopene cyclase (CrtY/L), etc. The modification enzymes include ketolases, hydroxylases, dehydratases, glycosylases, etc.

Engineering *E. coli* for increased carotenoid production has previously focused on overexpression of key isoprenoid pathway genes from multi-copy plasmids. Various studies have report between a 1.5× and 50× increase in carotenoid formation in such *E. coli* systems upon cloning and transformation of plasmids encoding isopentenyl diphosphate isomerase (idi), geranylgeranyl pyrophosphate (GGPP) synthase (gps), deoxy-D-xylulose-5-phosphate (DXP) synthase (dxs), and DXP reductoisomerase (dxr) from various sources (Kim, S.-W., and Keasling, J. D., *Biotech. Bioeng.*, 72:408–415 (2001); Mathews, P. D., and Wurtzel, E. T., *Appl. Microbiol. Biotechnol.*, 53:396–400 (2000); Harker, M, and Bramley, P. M., *FEBS Letter.*, 448:115–119 (1999); Misawa, N., and Shimada, H., *J. Biotechnol.*, 59:169–181 (1998); Liao et al., *Biotechnol. Bioeng.*, 62:235–241 (1999); Misawa et al., *Biochem. J.*, 324:421–426 (1997); and Wang et al., *Biotech. Bioeng.*, 62:235–241 (1999)).

Alternatively, other attempts to genetically engineer microbial hosts for increased production of carotenoids have focused on directed evolution of gps (Wang et al., *Biotechnol. Prog.*, 16:922–926 (2000)) and overexpression of various isoprenoid and carotenoid biosynthetic genes in different microbial hosts using endogenous and exogenous promoters (Lagarde et al., *Appl. Env. Microbiol.*, 66:64–72 (2000); Szkopinska et al., *J. Lipid Res.*, 38:962–968 (1997); Shimada et al., *Appl. Env. Microb.*, 64:2676–2680 (1998); and Yamano et al., *Biosci. Biotech. Biochem.*, 58:1112–1114 (1994)).

Although these attempts at modulating carotenoid production have had some positive results, the production increases that can be effective by modulation of pathway enzymes is finite. For example, it has been noted that increasing isoprenoid precursor supply seems to be lethal (Sandmann, G., *Trends in Plant Science*, 6:14–17 (2001)), indicating limitations in the amount of carotenoid storage in *E. coli*. It is clear that alternate modifications will have to be made to achieve higher levels.

The problem to be solved therefore is to create a carotenoid overproducing organism for the production of new and useful carotenoids that do not involve direct manipulation of carotenoid or isoprenoid biosynthesis pathway genes. Applicants have solved the stated problem through the discovery that mutations in genes not involved in the isoprenoid or carotenoid biosynthetic pathways have a marked effect in increasing carotenoid production in a carotenoid producing microorganism.

SUMMARY OF THE INVENTION

The invention provides a carotenoid overproducing microorganism comprising the genes encoding a functional isoprenoid enzymatic biosynthetic pathway comprising a disrupted gene selected from the group consisting of deaD, mreC and yfhE. Carotenoid overproducing microorganisms of the invention will preferably contain:
  a) an upper isoprenoid enzymatic biosynthetic pathway comprising the genes dxs, dxr, ygbP (ispD), ychB (ispE), ygbB (ispF), lytB, idi, ispA, and ispB; and
  b) a lower isoprenoid enzymatic biosynthetic pathway comprising the genes crtE, crtB, crtI, and crtY, and optionally crtZ and crtW In another embodiment the invention provides a carotenoid overproducing *E. coli* comprising:
  a) an upper isoprenoid enzymatic biosynthetic pathway comprising the genes dxs, dxr, ygbP (ispD), ychB (ispE), ygbB (ispF), lytB, idi, ispA, and ispB;
  b) a lower isoprenoid enzymatic biosynthetic pathway comprising the genes crtE, crtB, crtI, and crtY;
  c) mutations selected from the group consisting of: a mutation in the thrS gene as set forth in SEQ ID NO: 35, a mutation in the rpsA gene as set forth in SEQ ID NO: 37, a mutation in the rpoC gene as set forth in SEQ ID NO: 38, a mutation in the yjeR gene as set forth in SEQ ID NO: 39, and a mutation in the rhoL gene as set forth in SEQ ID NO: 41;
  wherein the genes of the lower isoprenoid enzymatic biosynthetic pathway reside on an autonomously replicating plasmid comprising a replicon selected from the group consisting of p15A and pMB1.

Additionally the invention provides a method for the production of a carotenoid comprising:
  a) contacting the carotenoid overproducing microorganism of the invention with a fermentable carbon substrate;
  b) growing the carotenoid overproducing microorganism of step (a) for a time sufficient to produce a carotenoid; and
  c) optionally recovering the carotenoid form the carotenoid overproducing microorganism of step (b).

BRIEF DESCRIPTION OF THE DRAWINGS AND SEQUENCE DESCRIPTIONS

Figure 1:
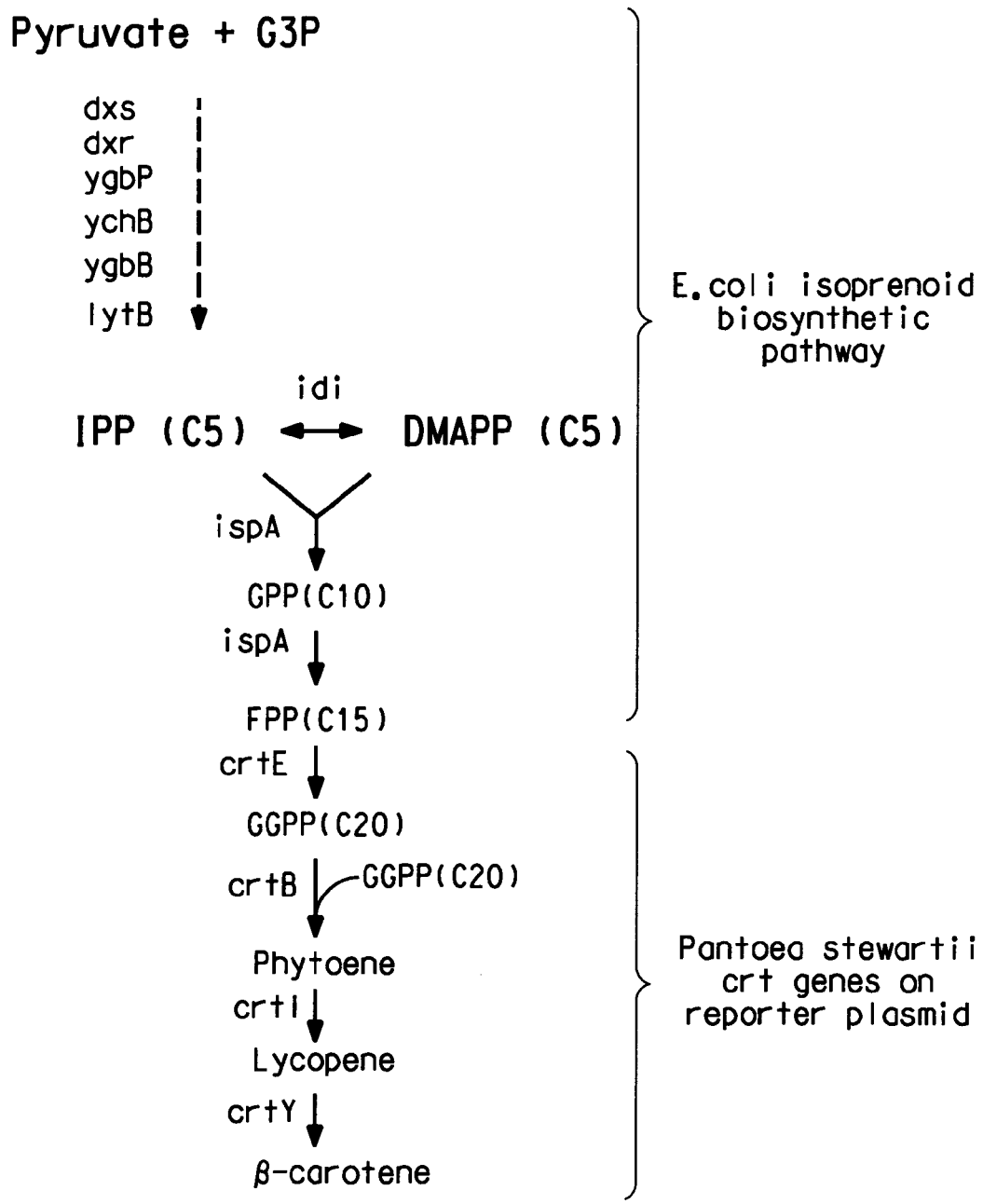
FIG. 1 shows the biosynthetic pathway for production of β-carotene from *E. coli* used in the present application.

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Nucleotide and Amino Acid Sequences for Carotenoid Biosynthesis Genes

| Gene/Protein Product | Source | Nucleotide SEQ ID NO | Amino Acid SEQ ID NO |
|---|---|---|---|
| CrtE | *Pantoea stewartii* | 1 | 2 |
| CrtX | *Pantoea stewartii* | 3 | 4 |
| CrtY | *Pantoea stewartii* | 5 | 6 |
| CrtI | *Pantoea stewartii* | 7 | 8 |
| CrtB | *Pantoea stewartii* | 9 | 10 |
| CrtZ | *Pantoea stewartii* | 11 | 12 |

SEQ ID NOs:13–14 are oligonucleotide primers used to amplify the carotenoid biosynthesis genes from *P. stewartii*.

SEQ ID NOs:15–16 are oligonucleotide primers used to identify the location of transposon insertions.

SEQ ID NOs:17–18 are oligonucleotide primers used to sequence the products amplified by SEQ ID NOs:15–16.

SEQ ID NOs:19–34 are oligonucleotide primers used to confirm transposon insertion sites.

SEQ ID NO: 35 is the nucleotide sequence of the mutated thrS gene with the Tn5 insertion.

SEQ ID NO: 36 is the nucleotide sequence of the mutated deaD gene with the Tn5 insertion.

SEQ ID NO: 37 is the nucleotide sequence of the mutated rpsA gene with the Tn5 insertion.

SEQ ID NO: 38 is the nucleotide sequence of the mutated rpoC gene with the Tn5 insertion.

SEQ ID NO: 39 is the nucleotide sequence of the mutated yjeR gene with the Tn5 insertion.

SEQ ID NO: 40 is the nucleotide sequence of the mutated mreC gene with the Tn5 insertion.

SEQ ID NO: 41 is the nucleotide sequence of the mutated rhoL gene with the Tn5 insertion.

SEQ ID NO: 42 is the nucleotide sequence of the mutated hscB (yfhE) gene with the Tn5 insertion.

SEQ ID NO: 43 is the nucleotide sequence for the reporter plasmid pPCB15.

DETAILED DESCRIPTION OF THE INVENTION

The invention relates to the discovery that mutations in certain genes, not part of the isoprenoid or carotenoid biosynthetic pathway have the effect of increasing carotenoid production. Carotenoid over-producing microorganisms are those that either naturally possess a complete pathway or those that have the pathway engineered by recombinant technology.

In this disclosure, a number of terms and abbreviations are used. The following definitions are provided.

"Open reading frame" is abbreviated ORF.

"Polymerase chain reaction" is abbreviated PCR.

The term "p15A" refers to a replicon for a family of plasmid vectors including pACYC based vectors.

The term "pMB1" refers to a replicon for a family of plasmid vectors including pUC and pBR based vectors The term "replicon" refers to a genetic element that behaves as an autonomous unit during replication. It contains sequences controlling replication of a plasmid including its origin of replication.

The term "isoprenoid" or "terpenoid" refers to the compounds and any molecules derived from the isoprenoid pathway including 10 carbon terpenoids and their derivatives, such as carotenoids and xanthophylls.

The "Isoprenoid Pathway" as used herein refers to the enzymatic pathway that is responsible for the production of isoprenoids. At a minimum the isoprenoid pathway contains the genes dxs, dxr, ygbP, ychB, ygbB, lytB, idi, ispA, and ispB which may also be referred to herein as the "Upper Isoprenoid Pathway" or "Upper Pathway". The "Carotenoid Biosynthetic Pathway" or "Lower Isoprenoid Pathway" or "Lower Pathway" refers to the genes encoding enzymes necessary for the production of carotenoid compounds and include, but are not limited to crtE, crtB, crtI, crtY, crtX, and crtZ.

The term "carotenoid biosynthetic enzyme" is an inclusive term referring to any and all of the enzymes encoded by the Pantoea crtEXYIB cluster. The enzymes include CrtE, CrtY, CrtI, CrtB, and CrtX.

A "disrupted gene" refers to a gene having a deletion or addition in the coding region of the gene such that there is a complete loss of the phenotype associated with that gene.

The term "dxs" refers to the enzyme D-1-deoxyxylulose 5-phosphate encoded by the *E. coli* dxs gene which catalyzes the condensation of pyruvate and D-glyceraldehyde 3-phosphate to D-1-deoxyxylulose 5-phosphate.

The term "idi" refers to the enzyme isopentenyl diphosphate isomerase encoded by the *E. coli* idi gene that converts isopentenyl diphosphate to dimethylallyl diphosphate.

The term "pPCB15" refers to the plasmid containing β-carotene biosynthesis genes Pantoea crtEXYIB. The plasmid was used as a reporter plasmid for monitoring β-carotene production in *E. coli* genetically engineered via the invented method (SEQ ID NO: 43).

The term "*E. coli*" refers to *Escherichia coli* strain K-12 derivatives, such as MG1655 (ATCC 47076).

The term "*Pantoea stewartii*" will be used interchangeably with *Erwinia stewartii* (Mergaert et al., *Int J. Syst. Bacteriol.*, 43:162–173 (1993)).

The term "*Pantoea ananatas*" is used interchangeably with *Erwinia uredovora* (Mergaert et al., *Int J. Syst. Bacteriol.*, 43:162–173 (1993)).

The term "*Pantoea* crtEXYIB cluster" refers to a gene cluster containing carotenoid synthesis genes crtEXYIB amplified from *Pantoea stewartii* ATCC 8199. The gene cluster contains the genes crtE, crtX, crtY, crtI, and crtB. The cluster also contains a crtZ gene organized in opposite direction adjacent to the crtB gene.

The term "CrtE" refers to geranylgeranyl pyrophosphate synthase enzyme encoded by crtE gene which converts trans-trans-farnesyl diphosphate+isopentenyl diphosphate to pyrophosphate+geranylgeranyl diphosphate.

The term "CrtY" refers to lycopene cyclase enzyme encoded by crtY gene which converts lycopene to β-carotene.

The term "CrtI" refers to phytoene dehydrogenase enzyme encoded by crtI gene which converts phytoene into lycopene via the intermediaries of phytofluene, zeta-carotene, and neurosporene by the introduction of 4 double bonds.

The term "CrtB" refers to phytoene synthase enzyme encoded by crtB gene which catalyzes reaction from pre-phytoene diphosphate (geranylgeranyl pyrophosphate) to phytoene.

The term "CrtX" refers to zeaxanthin glucosyl transferase enzyme encoded by crtX gene which converts zeaxanthin to zeaxanthin-β-diglucoside.

The term "CrtZ" refers to the β-carotene hydroxylase enzyme encoded by crtZ gene which catalyses hydroxylation reaction from β-carotene to zeaxanthin.

The term "thrS" refers to the threonyl-tRNA synthetase gene locus.

The term "deaD" refers to the RNA helicase gene locus.

The term "rpsA" refers to the 30S ribosomal subunit protein S1 gene locus.

The term "rpoC" refers to the RNA polymerase β' subunit gene locus.

The term "yjeR" refers to the oligo-ribonuclease gene locus.

The term "mreC" refers to the rod-shape determining protein gene locus.

The term "rhoL" refers to the rho operon leader peptide gene locus.

The terms "hscB" or "yfhE" refer to the heat shock cognate protein gene locus.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "complementary" is used to describe the relationship between nucleotide bases that are capable to hybridizing to one another. For example, with respect to DNA, adenosine is complementary to thymine and cytosine is complementary to guanine.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Operon", in bacterial DNA, is a cluster of contiguous genes transcribed from one promoter that gives rise to a polycistronic mRNA.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence encoding regulatory signals capable of affecting mRNA processing or gene expression.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "fermentable carbon substrate" refers to the carbon source metabolized by a carotenoid overproducing microorganism. Typically fermentable carbon substrates will include, but are not limited to, carbon sources selected from the group consisting of monosaccharides, oligosaccharides, polysaccharides, and one-carbon substrates or mixtures thereof.

The term "carotenoid overproducing microorganism" refers to a microorganism of the invention which has been genetically modified by the up-regulation or down-regulation of various genes to produce a carotenoid compound a levels greater than the wildtype or unmodified host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention relates to microorganisms that produce carotenoid compounds and methods for increasing carotenoid production in microorganisms having a functional isoprenoid biosynthetic pathway. Specifically, it has been found that mutations in genes having no direct relationship to the carotenoid biosynthetic pathway have been found to increase carbon flux through that pathway. For example, complete disruption of the deaD, mreC or yfhE genes was effective at increasing the production of carotenoid from an engineered host. Additionally, where genes of the lower carotenoid pathway reside on a plasmid having either a p15A or pMB1 replicon, mutations in the thrS, rpsA, rpoC, yjeR, and rhoL genes were found to be similarly effective.

Genes Involved in Carotenoid Production.

The enzyme pathway involved in the biosynthesis of carotenoids can be conveniently viewed in two parts, the upper isoprenoid pathway providing for the conversion of pyruvate and glyceraldehyde-3-phosphate to farnesyl pyrophosphate and the lower carotenoid biosynthetic pathway, which provides for the synthesis of phytoene and all subsequently produced carotenoids. The upper pathway is ubiquitous in many microorganisms. In the present invention it will only be necessary to introduce genes that comprise the lower pathway for the biosynthesis of the desired carotenoid. The key division between the two pathways concerns the synthesis of farnesyl pyrophosphate (FPP). Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. Where FPP synthesis is not provided by the host cell, it will be necessary to introduce the genes necessary for the production of FPP. Each of these pathways will be discussed below in detail.

The Upper Isoprenoid Pathway

Isopentenyl pyrophosphate (IPP) biosynthesis occurs through either of two pathways. First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria, green algae, and higher plants (Horbach et al., *FEMS Microbiol. Lett.*, 111:135–140 (1993); Rohmer et al, *Biochem.*, 295: 517–524 (1993); Schwender et al., *Biochem.*, 316: 73–80 (1996); and Eisenreich et al., *Proc. Natl. Acad. Sci. USA*, 93: 6431–6436 (1996)).

Many steps in both isoprenoid pathways are known (FIG. 1). For example, the initial steps of the alternate pathway leading to the production of IPP have been studied in *Mycobacterium tuberculosis* by Cole et al. (*Nature*, 393: 537–544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP. Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). Finally, the enzyme encoded by the ygbB gene converts 4-diphosphocytidyl-2C-methyl-D-erythritol 2-phosphate to 2C-methyl-D-erythritol 2,4-cyclodiphosphate in a CTP-dependent manner. This gene has also been recently renamed, and belongs to the isp gene cluster. Specifically, the new name for the ygbB gene is ispF (SwissProtein Accession #P36663).

It is known that 2C-methyl-D-erythritol 2,4-cyclodiphosphate can be further converted into IPP to ultimately produce carotenoids in the carotenoid biosynthesis pathway. However, the reactions leading to the production of isopentenyl monophosphate from 2C-methyl-D-erythritol 2,4-cyclodiphosphate are not yet well-characterized. The enzymes encoded by the lytB and gcpE genes (and perhaps others) are thought to participate in the reactions leading to formation of isopentenyl pyrophosphate (IPP) and dimethylallyl pyrophosphate (DMAPP).

IPP may be isomerized to DMAPP via IPP isomerase, encoded by the idi gene, however this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via isomerization of IPP to dimethylallyl pyrophosphate (DMAPP). This reaction is followed by a sequence of two prenyltransferase reactions catalyzed by ispA, leading to the creation of geranyl pyrophosphate (GPP; a 10-carbon molecule) and farnesyl pyrophosphate (FPP; 15-carbon molecule).

Genes encoding elements of the upper pathway are known from a variety of plant, animal, and bacterial sources, as shown in Table 2.

TABLE 2

Sources of Genes Encoding the Upper Isoprene Pathway

| Gene | GenBank ® Accession Number and Source Organism |
| --- | --- |
| dxs (D-1-deoxyxylulose 5-phosphate synthase) | AF035440, *Escherichia coli*<br>Y18874, *Synechococcus* PCC6301<br>AB026631, *Streptomyces* sp. CL190<br>AB042821, *Streptomyces griseolosporeus*<br>AF111814, *Plasmodium falciparum*<br>AF143812, *Lycopersicon esculentum*<br>AJ279019, *Narcissus pseudonarcissus*<br>AJ291721, *Nicotiana tabacum* |
| dxr (1-deoxy-D-xylulose 5-phosphate reductoisomerase) | AB013300, *Escherichia coli*<br>AB049187, *Streptomyces griseolosporeus*<br>AF111813, *Plasmodium falciparum*<br>AF116825, *Mentha* × *piperita*<br>AF148852, *Arabidopsis thaliana*<br>AF182287, *Artemisia annua*<br>AF250235, *Catharanthus roseus*<br>AF282879, *Pseudomonas aeruginosa*<br>AJ242588, *Arabidopsis thaliana*<br>AJ250714, *Zymomonas mobilis* strain ZM4<br>AJ292312, *Klebsiella pneumoniae*<br>AJ297566, *Zea mays* |
| ispD (2-C-methyl-D-erythritol 4-phosphate cytidylyltransferase) | AB037876, *Arabidopsis thaliana*<br>AF109075, *Clostridium difficile*<br>AF230736, *Escherichia coli*<br>AF230737, *Arabidopsis thaliana* |
| ispE (4-diphosphocytidyl-2-C-methyl-D-erythritol kinase) | AF216300, *Escherichia coli*<br>AF263101, *Lycopersicon esculentum*<br>AF288615, *Arabidopsis thaliana* |
| ispF (2-C-methyl-D-erythritol 2,4-cyclodiphosphate synthase) | AB038256, *Escherichia coli* mecs gene<br>AF230738, *Escherichia coli*<br>AF250236, *Catharanthus roseus* (MECS)<br>AF279661, *Plasmodium falciparum*<br>AF321531, *Arabidopsis thaliana* |
| lytB | AF027189, *Acinetobacter* sp. BD413<br>AF098521, *Burkholderia pseudomallei*<br>AF291696, *Streptococcus pneumoniae*<br>AF323927, *Plasmodium falciparum*<br>M87645, *Bacillus subtillis*<br>U38915, *Synechocystis* sp.<br>X89371, *Campylobacter jejuni* |
| gcpE (1-hydroxy-2-methyl-2-(E)-butenyl 4-diphosphate synthase) | O67496, *Aquifex aeolicus*<br>P54482, *Bacillus subtilis*<br>Q9pky3, *Chlamydia muridarum*<br>Q9Z8H0, *Chlamydophila pneumoniae*<br>O84060, *Chlamydia trachomatis*<br>P27433, *Escherichia coli*<br>P44667, *Haemophilus influenzae*<br>Q9ZLL0, *Helicobacter pylori* J99<br>O33350, *Mycobacterium tuberculosis*<br>S77159, *Synechocystis* sp.<br>Q9WZZ3, *Thermotoga maritima*<br>O83460, *Treponema pallidum*<br>Q9JZ40, *Neisseria meningitidis*<br>Q9PPM1, *Campylobacter jejuni*<br>Q9RXC9, *Deinococcus radiodurans*<br>AAG07190, *Pseudomonas aeruginosa*<br>Q9KTX1, *Vibrio cholerae* |
| ispA (FPP synthase) | AB003187, *Micrococcus luteus*<br>AB016094, *Synechococcus elongatus*<br>AB021747, *Oryza sativa* FPPS1 gene for farnesyl diphosphate synthase<br>AB028044, *Rhodobacter sphaeroides*<br>AB028046, *Rhodobacter capsulatus*<br>AB028047, *Rhodovulum sulfidophilum*<br>AF112881 and AF136602, *Artemisia annua* |

TABLE 2-continued

Sources of Genes Encoding the Upper Isoprene Pathway

| Gene | GenBank ® Accession Number and Source Organism |
|---|---|
| | AF384040, *Mentha × piperita* |
| | D00694, *Escherichia coli* |
| | D13293, *B. stearothermophilus* |
| | D85317, *Oryza sativa* |
| | X75789, *Arabidopsis thaliana* |
| | Y12072, *G. arboreum* |
| | Z49786, *H. brasiliensis* |
| | U80605, *Arabidopsis thaliana* farnesyl diphosphate synthase precursor (FPS1) mRNA, complete cds |
| | X76026, *K. lactis* FPS gene for farnesyl diphosphate synthetase, QCR8 gene for bc1 complex, subunit VIII |
| | X82542, *P. argentatum* mRNA for farnesyl diphosphate synthase (FPS1) |
| | X82543, *P. argentatum* mRNA for farnesyl diphosphate synthase (FPS2) |
| | BC010004, *Homo sapiens*, farnesyl diphosphate synthase (farnesyl pyrophosphate synthetase, dimethylallyltranstransferase, geranyltranstransferase), clone MGC 15352 IMAGE, 4132071, mRNA, complete cds |
| | AF234168, *Dictyostelium discoideum* farnesyl diphosphate synthase (Dfps) |
| | L46349, *Arabidopsis thaliana* farnesyl diphosphate synthase (FPS2) mRNA, complete cds |
| | L46350, *Arabidopsis thaliana* farnesyl diphosphate synthase (FPS2) gene, complete cds |
| | L46367, *Arabidopsis thaliana* farnesyl diphosphate synthase (FPS1) gene, alternative products, complete cds |
| | M89945, Rat farnesyl diphosphate synthase gene, exons 1–8 |
| | NM_002004, *Homo sapiens* farnesyl diphosphate synthase (farnesyl pyrophosphate synthetase, dimethylallyltranstransferase, geranyltranstransferase) (FDPS), mRNA |
| | U36376, *Artemisia annua* farnesyl diphosphate synthase (fps1) mRNA, complete cds |
| | XM_001352, *Homo sapiens* farnesyl diphosphate synthase (farnesyl pyrophosphate synthetase, dimethylallyltranstransferase, geranyltranstransferase) (FDPS), mRNA |
| | XM_034497, *Homo sapiens* farnesyl diphosphate synthase (farnesyl pyrophosphate synthetase, dimethylallyltranstransferase, geranyltranstransferase) (FDPS), mRNA |
| | XM_034498, *Homo sapiens* farnesyl diphosphate synthase (farnesyl pyrophosphate synthetase, dimethylallyltranstransferase, geranyltranstransferase) (FDPS), mRNA |
| | XM_034499, *Homo sapiens* farnesyl diphosphate synthase (farnesyl pyrophosphate synthetase, dimethylallyltranstransferase, geranyltranstransferase) (FDPS), mRNA |
| | XM_034500, *Homo sapiens* farnesyl diphosphate synthase (farnesyl pyrophosphate synthetase, dimethylallyltranstransferase, geranyltranstransferase) (FDPS), mRNA |

The most preferred source of genes for the upper isoprenoid pathway in the present invention are the endogenous genes in *E. coli* MG1655.

The Carotenoid Biosynthetic Pathway—Lower Isoprenoid Pathway

The division between the upper isoprenoid pathway and the lower carotenoid pathway is somewhat subjective. Because FPP synthesis is common in both carotenogenic and non-carotenogenic bacteria, the Applicants considers the first step in the lower carotenoid biosynthetic pathway to begin with the prenyltransferase reaction converting farnesyl pyrophosphate (FPP) to geranylgeranyl pyrophosphate (GGPP). The gene crtE, encoding GGPP synthetase, is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by phytoene synthase.

Lycopene, which imparts a "red"-colored spectra, is produced from phytoene through four sequential dehydrogenation reactions by the removal of eight atoms of hydrogen. This series of dehydrogenation reactions is catalyzed by phytoene desaturase. Intermediaries in this reaction are phytofluene, zeta-carotene, and neurosporene.

Lycopene cyclase (crtY) converts lycopene to β-carotene.

β-carotene is converted to zeaxanthin via a hydroxylation reaction resulting from the activity of β-carotene hydroxylase (encoded by the crtZ gene). β-cryptoxanthin is an intermediate in this reaction.

β-carotene is converted to canthaxanthin by β-carotene ketolase (encoded by the crtW gene). Echinenone in an intermediate in this reaction. Canthaxanthin can then be converted to astaxanthin by β-carotene hydroxylase (encoded by the crtZ gene). Adonbirubrin is an intermediate in this reaction.

Zeaxanthin can be converted to zeaxanthin-β-diglucoside. This reaction is catalyzed by zeaxanthin glucosyl transferase (crtX).

Zeaxanthin can be converted to astaxanthin by β-carotene ketolase encoded by a crtW or crtO gene. Adonixanthin is an intermediate in this reaction.

Spheroidene can be converted to spheroidenone by spheroidene monooxygenase (encoded by crtA).

Neurosporene can be converted to spheroidene and lycopene can be converted to spirilloxanthin by the sequential actions of hydroxyneurosporene synthase, methoxyneurosporene desaturase, and hydroxyneurosporene-O-methyltransferase encoded by the crtC, crtD and crtF genes, respectively.

β-carotene can be converted to isorenieratene by β-carotene desaturase encoded by crtU.

Genes encoding elements of the lower carotenoid biosynthetic pathway are known from a variety of plant, animal, and bacterial sources, as shown in Table 3.

TABLE 3

Sources of Genes Encoding the Lower Carotenoid Biosynthetic Pathway

| Gene | Genbank Accession Number and Source Organism |
|---|---|
| crtE (GGPP Synthase) | AB000835, *Arabidopsis thaliana* |
|  | AB016043 and AB019036, *Homo sapiens* |
|  | AB016044, *Mus musculus* |
|  | AB027705 and AB027706, *Daucus carota* |
|  | AB034249, *Croton sublyratus* |
|  | AB034250, *Scoparia dulcis* |
|  | AF020041, *Helianthus annuus* |
|  | AF049658, *Drosophila melanogaster* signal recognition particle 19 kDa protein (srp 19) gene, partial sequence; and geranylgeranyl pyrophosphate synthase (quemao) gene, complete cds |
|  | AF049659, *Drosophila melanogaster* geranylgeranyl pyrophosphate synthase mRNA, complete cds |
|  | AF139916, *Brevibacterium linens* |
|  | AF279807, *Penicillium paxilli* geranylgeranyl pyrophosphate synthase (ggs1) gene, complete |
|  | AF279808 *Penicillium paxilli* dimethylallyl tryptophan synthase (paxD) gene, partial cds; and cytochrome P450 monooxygenase (paxQ), cytochrome P450 monooxygenase (paxP), PaxC (paxC), monooxygenase (paxM), geranylgeranyl pyrophosphate synthase (paxG), PaxU (paxU), and metabolite transporter (paxT) genes, complete cds |
|  | AJ010302, *Rhodobacter sphaeroides* |
|  | AJ133724, *Mycobacterium aurum* |
|  | AJ276129, *Mucor circinelloides f. lusitanicus* carG gene for geranylgeranyl pyrophosphate synthase, exons 1–6 |
|  | D85029 *Arabidopsis thaliana* mRNA for geranylgeranyl pyrophosphate synthase, partial cds |
|  | L25813, *Arabidopsis thaliana* |
|  | L37405, *Streptomyces griseus* geranylgeranyl pyrophosphate synthase (crtB), phytoene desaturase (crtE) and phytoene synthase (crtI) genes, complete cds |
|  | U15778, *Lupinus albus* geranylgeranyl pyrophosphate synthase (ggps1) mRNA, complete cds |
|  | U44876, *Arabidopsis thaliana* pregeranylgeranyl pyrophosphate synthase (GGPS2) mRNA, complete cds |
|  | X92893, *C. roseus* |
|  | X95596, *S. griseus* |
|  | X98795, *S. alba* |
|  | Y15112, *Paracoccus marcusii* |
| crtX (Zeaxanthin glucosylase) | D90087, *E. uredovora* |
|  | M87280 and M90698, *Pantoea agglomerans* |
| crtY (Lycopene-β-cyclase) | AF139916, *Brevibacterium linens* |
|  | AF152246, *Citrus x paradisi* |

TABLE 3-continued

Sources of Genes Encoding the Lower Carotenoid Biosynthetic Pathway

| Gene | Genbank Accession Number and Source Organism |
|---|---|
| | AF218415, *Bradyrhizobium* sp. ORS278 |
| | AF272737, *Streptomyces griseus* strain IFO13350 |
| | AJ133724, *Mycobacterium aurum* |
| | AJ250827, *Rhizomucor circinelloides f. lusitanicus* carRP gene for lycopene cyclase/phytoene synthase, exons 1–2 |
| | AJ276965, *Phycomyces blakesleeanus* carRA gene for phytoene synthase/lycopene cyclase, exons 1–2 |
| | D58420, *Agrobacterium aurantiacum* |
| | D83513, *Erythrobacter longus* |
| | L40176, *Arabidopsis thaliana* lycopene cyclase (LYC) mRNA, complete cds |
| | M87280, *Pantoea agglomerans* |
| | U50738, *Arabodopsis thaliana* lycopene epsilon cyclase mRNA, complete cds |
| | U50739 *Arabidosis thaliana* lycopene β cyclase mRNA, complete cds |
| | U62808, *Flavobacterium* ATCC21588 |
| | X74599 *Synechococcus* sp. lcy gene for lycopene cyclase |
| | X81787 *N. tabacum* CrtL-1 gene encoding lycopene cyclase |
| | X86221, *C. annuum* |
| | X86452, *L. esculentum* mRNA for lycopene β-cyclase |
| | X95596, *S. griseus* |
| | X98796, *N. pseudonarcissus* |
| crtI (Phytoene desaturase) | AB046992, *Citrus unshiu* CitPDS1 mRNA for phytoene desaturase, complete cds |
| | AF039585 *Zea mays* phytoene desaturase (pds1) gene promoter region and exon 1 |
| | AF049356 *Oryza sativa* phytoene desaturase precursor (Pds) mRNA, complete cds |
| | AF139916, *Brevibacterium linens* |
| | AF218415, *Bradyrhizobium* sp. ORS278 |
| | AF251014, *Tagetes erecta* |
| | AF364515, *Citrus x paradisi* |
| | D58420, *Agrobacterium aurantiacum* |
| | D83514, *Erythrobacter longus* |
| | L16237, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | L39266, *Zea mays* phytoene desaturase (Pds) mRNA, complete cds |
| | M64704, Soybean phytoene desaturase |
| | M88683, *Lycopersicon esculentum* phytoene desaturase (pds) mRNA, complete cds |
| | S71770, carotenoid gene cluster |
| | U37285, *Zea mays* |
| | U46919, *Solanum lycopersicum* phytoene desaturase (Pds) gene, partial cds |
| | U62808, *Flavobacterium* ATCC21588 |
| | X55289, *Synechococcus pds* gene for phytoene desaturase |
| | X59948, *L. esculentum* |
| | X62574, *Synechocystis* sp. pds gene for phytoene desaturase |
| | X68058 *C. annuum* pds1 mRNA for phytoene desaturase |
| | X71023 *Lycopersicon esculentum* pds gene for phytoene desaturase |
| | X78271, *L. esculentum* (Ailsa Craig) PDS gene |
| | X78434, *P. blakesleeanus* (NRRL1555) carB gene |
| | X78815, *N. pseudonarcissus* |
| | X86783, *H. pluvialis* |
| | Y14807, *Dunaliella bardawil* |
| | Y15007, *Xanthophyllomyces dendrorhous* |
| | Y15112, *Paracoccus marcusii* |

TABLE 3-continued

Sources of Genes Encoding the Lower Carotenoid Biosynthetic Pathway

| Gene | Genbank Accession Number and Source Organism |
|---|---|
| crtB (Phytoene synthase) | Y15114, Anabaena PCC7210 crtP gene<br>Z11165, R. capsulatus<br>AB001284, Spirulina platensis<br>AB032797, Daucus carota PSY mRNA for phytoene synthase, complete cds<br>AB034704, Rubrivivax gelatinosus<br>AB037975, Citrus unshiu<br>AF009954, Arabidopsis thaliana phytoene synthase (PSY) gene, complete cds<br>AF139916, Brevibacterium linens<br>AF152892, Citrus x paradisi<br>AF218415, Bradyrhizobium sp. ORS278<br>AF220218, Citrus unshiu phytoene synthase (Psy1) mRNA, complete cds<br>AJ010302, Rhodobacter<br>AJ133724, Mycobacterium aurum<br>AJ278287, Phycomyces blakesleeanus carRA gene for lycopene cyclase/phytoene synthase,<br>AJ304825<br>Helianthus annuus mRNA for phytoene synthase (psy gene)<br>AJ308385<br>Helianthus annuus mRNA for phytoene synthase (psy gene)<br>D58420, Agrobacterium aurantiacum<br>L23424<br>Lycopersicon esculentum phytoene synthase (PSY2) mRNA, complete cds<br>L25812, Arabidopsis thaliana<br>L37405, Streptomyces griseus geranylgeranyl pyrophosphate synthase (crtB), phytoene desaturase (crtE) and phytoene synthase (crtI) genes, complete cds<br>M38424<br>Pantoea agglomerans phytoene synthase (crtE) gene, complete cds<br>M87280, Pantoea agglomerans<br>S71770, carotenoid gene cluster<br>U32636<br>Zea mays phytoene synthase (Y1) gene, complete cds<br>U62808, Flavobacterium ATCC21588<br>U87626, Rubrivivax gelatinosus<br>U91900, Dunaliella bardawil<br>X52291, Rhodobacter capsulatus<br>X60441, L. esculentum GTom5 gene for phytoene synthase<br>X63873<br>Synechococcus PCC7942 pys gene for phytoene synthase<br>X68017<br>C. annuum psy1 mRNA for phytoene synthase<br>X69172<br>Synechocystis sp. pys gene for phytoene synthase<br>X78814, N. pseudonarcissus |
| crtZ (β-carotene hydroxylase) | D58420, Agrobacterium aurantiacum<br>D58422, Alcaligenes sp.<br>D90087, E. uredovora<br>M87280, Pantoea agglomerans<br>U62808, Flavobacterium ATCC21588<br>Y15112, Paracoccus marcusii |
| crtW (β-carotene ketolase) | AF218415, Bradyrhizobium sp. ORS278<br>D45881, Haematococcus pluvialis<br>D58420, Agrobacterium aurantiacum<br>D58422, Alcaligenes sp.<br>X86782, H. pluvialis<br>Y15112, Paracoccus marcusii |
| crtO (β-C4-ketolase) | X86782, H. pluvialis<br>Y15112, Paracoccus marcusii |
| crtU (β-carotene dehydrogenase) | AF047490, Zea mays<br>AF121947, Arabidopsis thaliana<br>AF139916, Brevibacterium linens<br>AF195507, Lycopersicon esculentum |

TABLE 3-continued

Sources of Genes Encoding the Lower Carotenoid
Biosynthetic Pathway

| Gene | Genbank Accession Number and Source Organism |
|---|---|
|  | AF272737, *Streptomyces griseus* strain IFO13350 |
|  | AF372617, *Citrus x paradisi* |
|  | AJ133724, *Mycobacterium aurum* |
|  | AJ224683, *Narcissus pseudonarcissus* |
|  | D26095 and U38550, *Anabaena* sp. |
|  | X89897, *C. annuum* |
|  | Y15115, *Anabaena* PCC7210 crtQ gene |
| crtA | AJ010302, *Rhodobacter sphaeroides* |
| (spheroidene monooxygenase) | Z11165 and X52291, *Rhodobacter capsulatus* |
| crtC | AB034704, *Rubrivivax gelatinosus* |
| (hydroxyneurosporene synthase) | AF195122 and AJ010302, *Rhodobacter sphaeroides* |
|  | AF287480, *Chlorobium tepidum* |
|  | U73944, *Rubrivivax gelatinosus* |
|  | X52291 and Z11165, *Rhodobacter capsulatus* |
|  | Z21955, *M. xanthus* |
| crtD | AJ010302 and X63204, *Rhodobacter sphaeroides* |
| (carotenoid 3,4-desaturase) | U73944, *Rubrivivax gelatinosus* |
|  | X52291 and Z11165, *Rhodobacter capsulatus* |
| crtF | AB034704, *Rubrivivax gelatinosus* |
| (1-OH-carotenoid methylase) | AF288602, *Chloroflexus aurantiacus* |
|  | AJ010302, *Rhodobacter sphaeroides* |
|  | X52291 and Z11165, *Rhodobacter capsulatus* |

The most preferred source of genes for the lower carotenoid biosynthetic pathway in the present invention are from *Pantoea stewartii* (ATCC No. 8199). Sequences of these preferred genes are presented as the following SEQ ID numbers: the crtE gene (SEQ ID NO: 1), the crtX gene (SEQ ID NO: 3), crtY (SEQ ID NO: 5), the crtI gene (SEQ ID NO: 7), the crtB gene (SEQ ID NO: 9) and the crtZ gene (SEQ ID NO: 11).

Gene Mutations

The invention relates to the discovery that certain mutations of chromosomal genes unexpectedly resulted in the increased production of carotenoids. Several of the mutations were complete gene disruptions whereas others were mutations in the carboxyl end of essential genes that resulted in an alteration, but not complete loss of gene function. Genes having complete disruptions included the deaD, mreC, and yfhE genes. Genes where only partial function was lost included the thrS, rpsA, rpoC, yjeR, and rhoL genes.

In the case where the disruptions occur in the deaD, mreC and yfhE genes, the elements of the upper and lower isoprenoid pathway may be either integrated into the cell genome or present, in whole or in part, on an autonomously replicating plasmid. However, in the case of the partial mutations in the thrS, rpsA, rpoC, yjeR, and rhoL genes, it is essential to the invention that genes belonging to the lower isoprenoid pathway (needed for the production of the desired carotenoid compound) be present on a plasmid and that plasmid be antisense RNA regulated as is the case with plasmids having the p15A and pMB1 replicons.

The copy number of two types of ColE1 plasmids, p15A and pMB1 derived replicons, is regulated by the antisense mechanism (Tomizawa, J., *Cell*, 38:861–870 (1984)). A transcript (RNA II) from the ColE1 primer promoter forms a persistent hybrid with the template DNA near the replication origin. The hybridized RNA II is cleaved by RNAase H to form the primer for replication initiation. Binding of the antisense RNA (RNA I) to RNA II inhibits the hybridization and thus prevents primer formation for replication. Rop is a small protein that when bound to both RNA molecules, increases the stability of the RNA I/RNA II complex, thus decreasing the likelihood of replication.

Methods of constructing plasmids suitable in the present invention are common and well known in the art (Sambrook et al., supra). For example, typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell, are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, ara, tet, trp, $IP_L$, $IP_R$, T7, tac, and trc (useful for expression in *Escherichia coli*) as well as the amy, apr, npr promoters and various phage promoters useful for expression in Bacillus.

Termination control regions may also be derived from various genes native to the preferred hosts. Optionally, a termination site may be unnecessary, however, it is most preferred if included.

Similarly methods of making the present mutations are common and well known in the art and any suitable method may be employed. For example, where sequence of the gene to be mutated is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.*, 171:4617–4622 (1989), Balbas et al., *Gene*, 136:211–213 (1993), Gueldener et al., *Nucleic Acids Res.*, 24:2519–2524 (1996), and Smith et al., *Methods Mol. Cell. Biol.*, 5:270–277 (1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, M A., or Deshpande, Mukund V., *Appl. Biochem. Biotechnol.*, 36, 227, (1992).

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7, and the EZ::TN Transposon Insertion Systems, available from Epicentre Technologies, Madison, Wiss., based upon the Tn5 bacterial transposable element).

In the context of the present invention, random mutagenesis was performed using EZ:TN™ <KAN-2> Tnp Transposome™ kit (Epicentre Technologies, Madison, Wiss.). Eight chromosomal mutations were isolated that increased β-carotene production in *E. coli*. These included Tn5 insertions in three non-essential genes (deaD, mreC, hscB) that likely disrupted their functions, and Tn5 insertions in the carboxyl end of five essential genes (thrS, rpsA, rpoC, yjeR, rhoL) that likely altered their functions.

Carotenoid Production

The mutations described by the present invention are in housekeeping genes. Since transcription, translation and protein biosynthetic apparatus is the same irrespective of the microorganisms and the feedstock, these mutations are likely to have similar effect in many host strains that can be used for carotenoid production including, but are not limited to, fungal or yeast species such as *Aspergillus, Trichoderma, Saccharomyces, Pichia, Candida, Hansenula*, or bacterial species such as *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Methylobacterium, Alcaligenes, Synechocystis, Synechococcus, Anabaena, Thiobacillus, Methanobacterium, Klebsiella, Myxococcus*, and *Staphylococcus*.

Large-scale microbial growth may utilize a fermentable carbon substrate covering a wide range of simple or complex carbohydrates, organic acids and alcohols, and/or saturated hydrocarbons such as methane or carbon dioxide in the case of photosynthetic or chemoautotrophic hosts. Carotenoids produced in the hosts include, but not limited to, antheraxanthin, adonixanthin, astaxanthin, canthaxanthin, capsorubrin,β-cryptoxanthin, didehydrolycopene, didehydrolycopene, β-carotene, ζ-carotene, δ-carotene, γ-carotene, keto-γ-carotene, ψ-carotene, ε-carotene, β,ψ-carotene, torulene, echinenone, gamma-carotene, zeta-carotene, alpha-cryptoxanthin, diatoxanthin, 7,8-didehydroastaxanthin, fucoxanthin, fucoxanthinol, isorenieratene, β-isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, zeaxanthin, and C30-carotenoids.

DESCRIPTION OF THE PREFERRED EMBODIMENTS

Using random transposon mutagenesis, several mutations to non-isoprenoid/carotenoid biosynthetic pathway genes have been discovered. These mutations serve to increase production of β-carotene in an *E. coli* strain harboring a reporter plasmid expressing genes involved in carotenoid biosynthesis.

Figure 5:
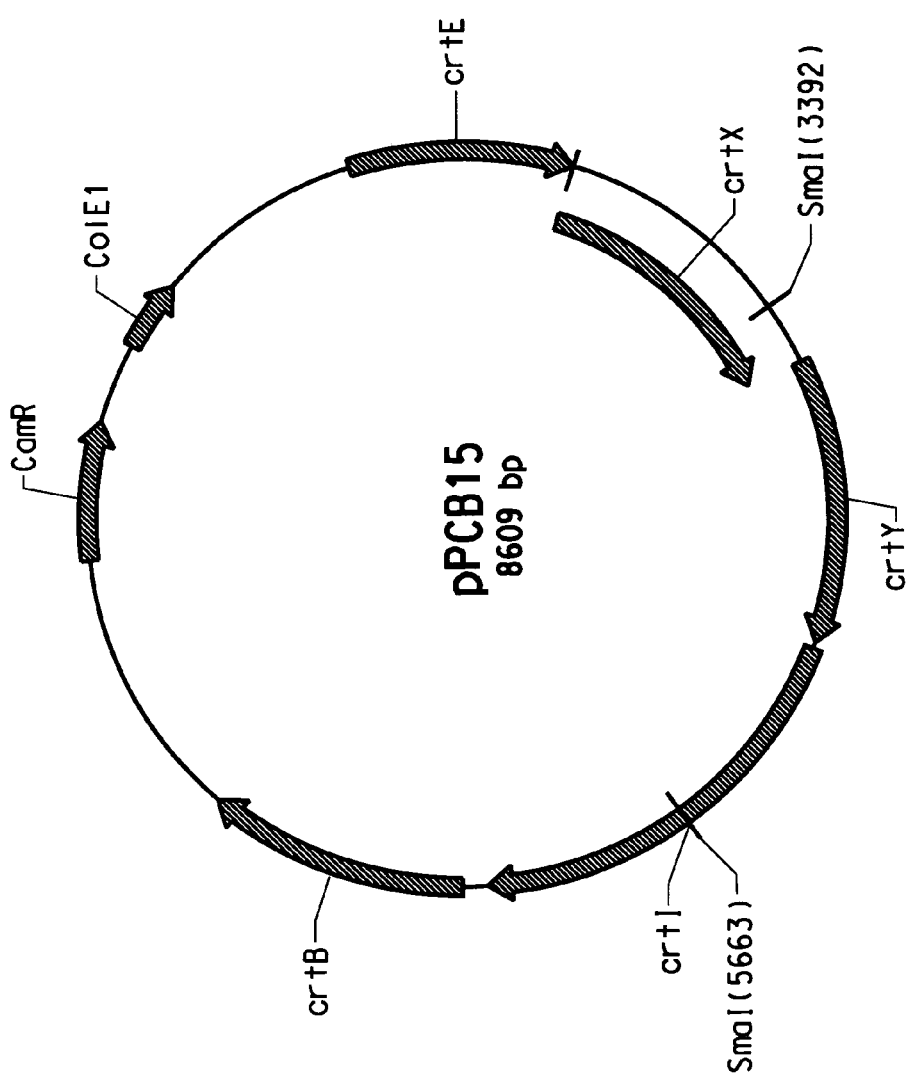
FIG. 5 shows the pPCB15 plasmid encoding carotenoid biosynthetic genes used in the present application.

In one embodiment, the *Pantoea stewartii* (ATCC No. 8199) crtEXYIB gene cluster was cloned into a vector, creating reporter plasmid pPCB15 (Examples 1 and 3, FIG. 5; SEQ ID NO. 43). Identification of the individual genes was verified by sequence analysis (Example 2, Table 4).

Plasmid pPCB15 was transformed into *E. coli* MG 1655, creating a strain capable of β-carotene production. The level of β-carotene production in *E. coli* MG 1655 (pPCB15) was used as the control.

Figure 2:
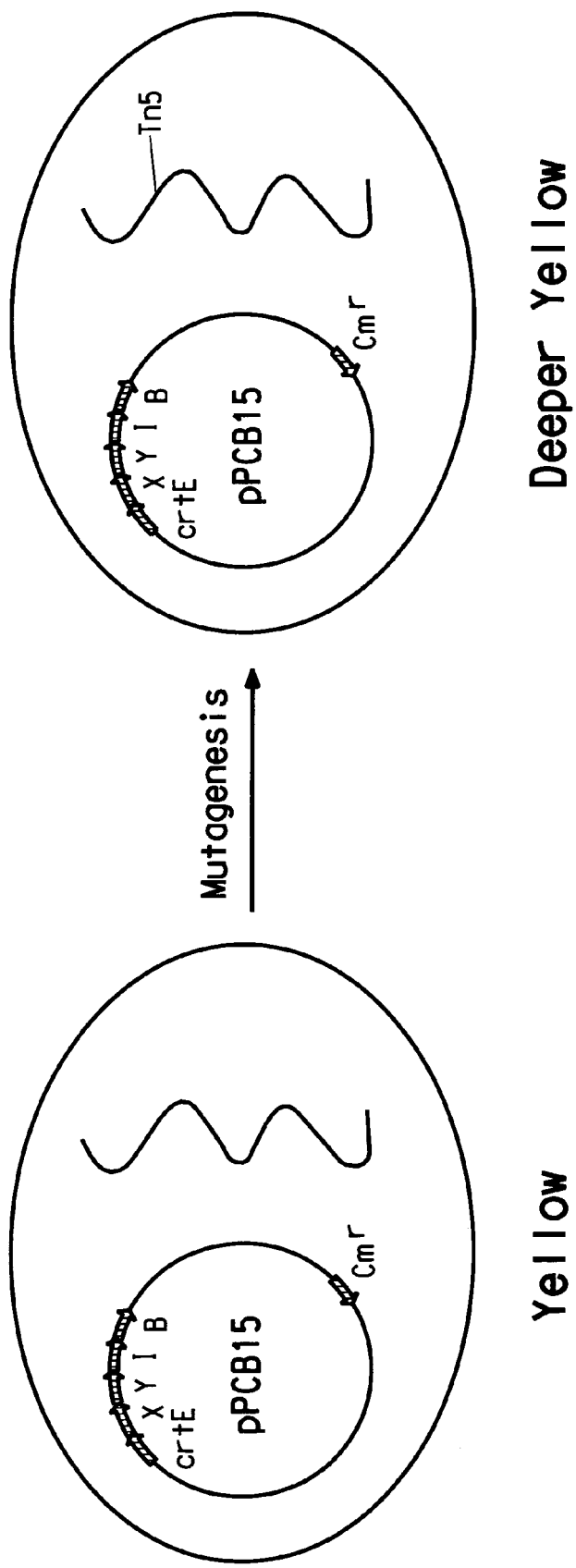
FIG. 2 shows the strategy for mutagenesis and screening of *E. coli* chromosomal mutants that increase carotenoid production.
Figure 3:
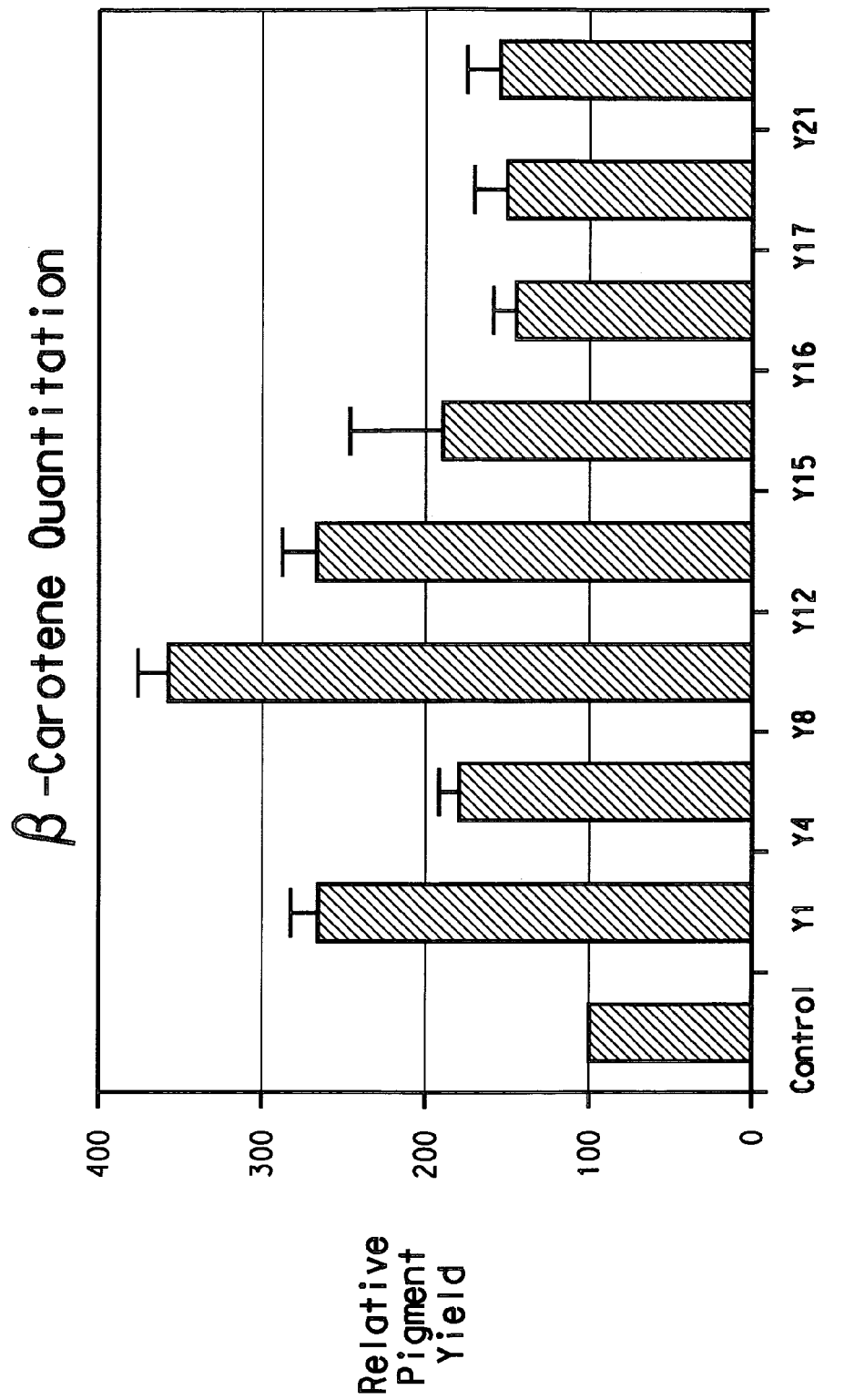
FIG. 3 shows the β-carotene production in *E. coli* mutants created in the present invention.

In another embodiment, chrosomomal transposon mutagenesis was done on the *E. coli* strain containing pPCB15 (Example 3, FIG. 2). Resulting strains that developed a deeper yellow color in comparison to the control strain were selected and analyzed (Example 4; FIGS. 2 and 3). Three mutant strains (Y1, Y8, and Y12) exhibited a 2.5–3.5 fold increase in production of β-carotene while mutants Y4, Y15, Y16, Y17, and Y21 showed a 1.5–2.0 fold increase.

Figure 4A:
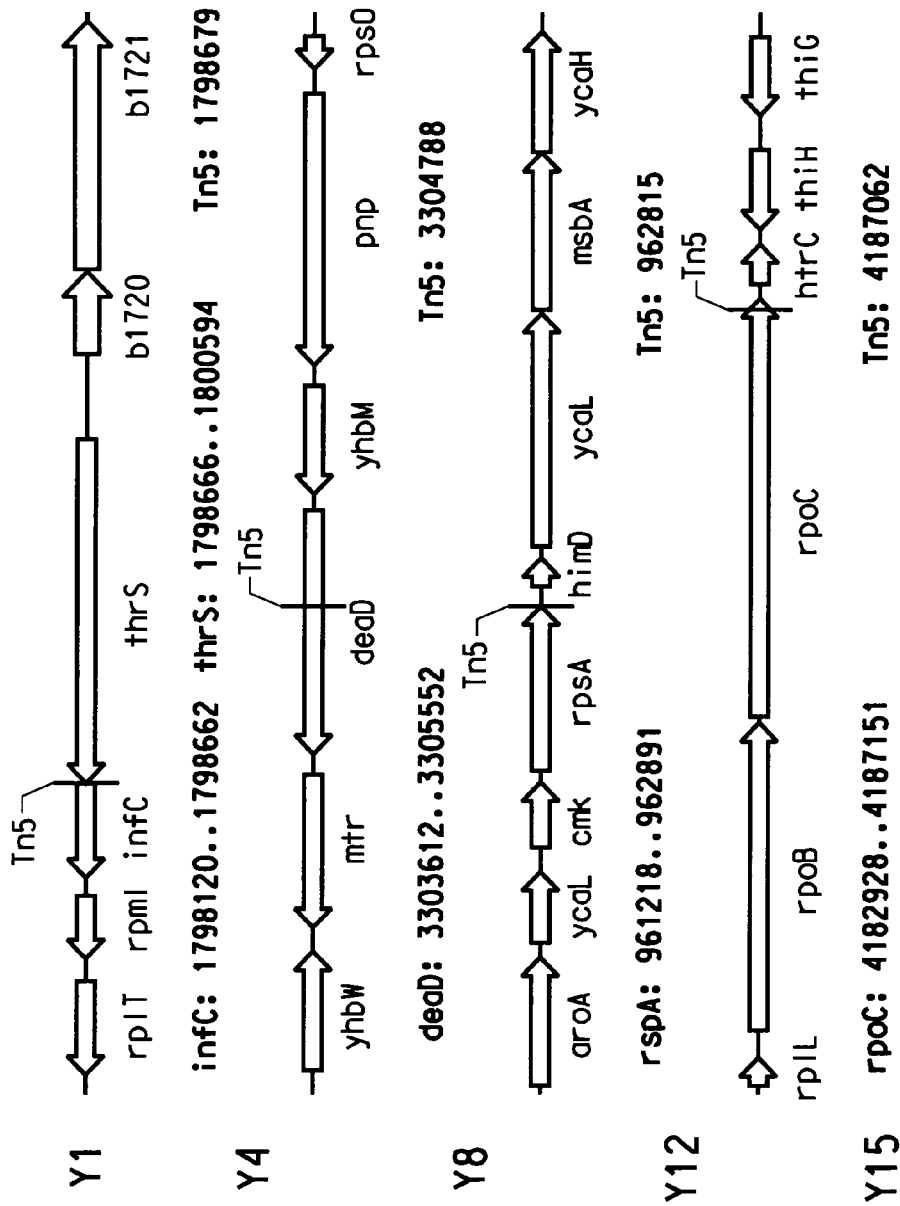
FIG. 4 shows the genetic organization of the regions of the *E. coli* chromosome where transposon insertions were located in the various *E. coli* mutants of the present invention.
Figure 4B:
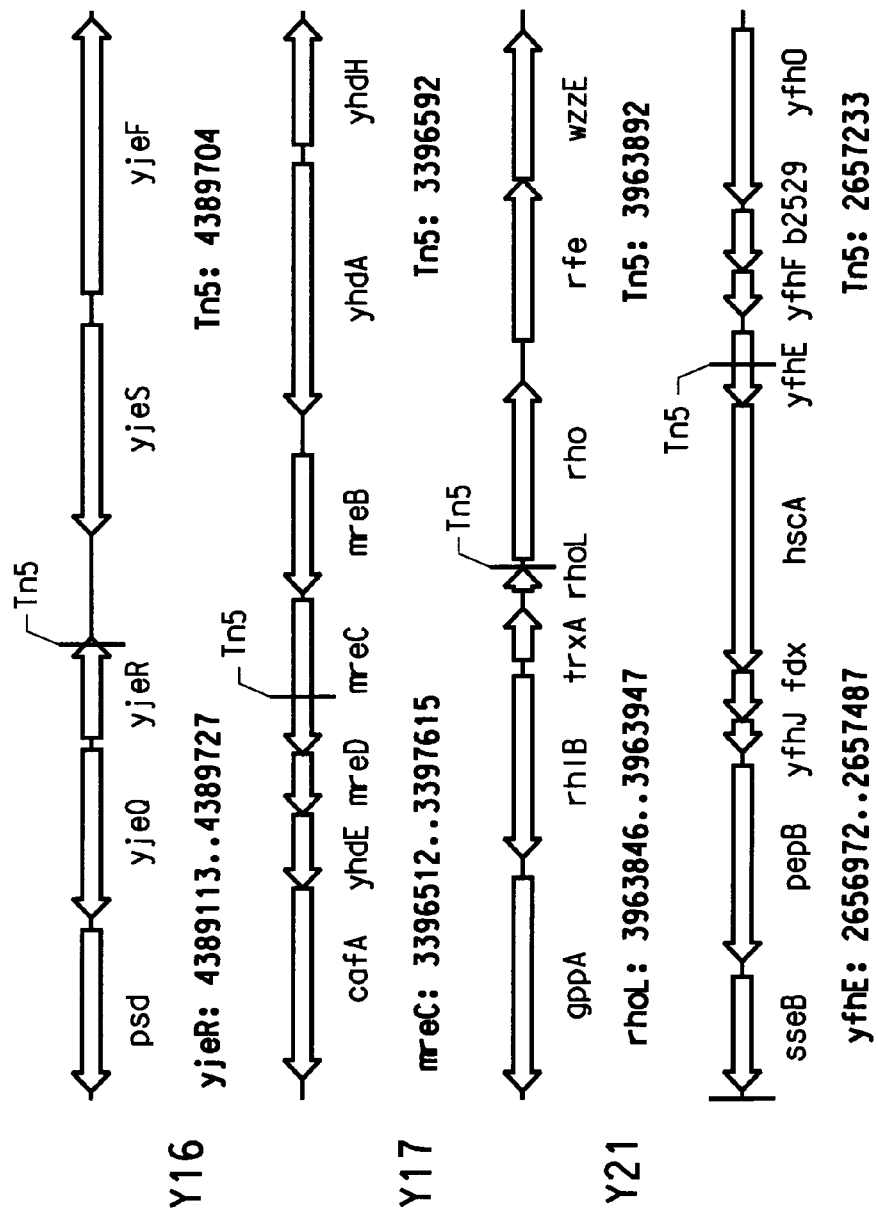

In another embodiment, the transposon insertion sites on the *E. coli* chromosome were mapped and confirmed using PCR fragment analysis (Examples 5 and 6, Table 5, FIG. 4). In a preferred embodiment, the identified mutant genes containing a Tn5 insertion are selected from the group consisting of thrS (SEQ ID NO. 35), deaD (SEQ ID NO. 36), rpsA (SEQ ID NO. 37), rpoC (SEQ ID NO. 38), yjeR (SEQ ID NO: 39), mreC (SEQ ID NO. 40), rhoL (SEQ ID NO. 41), and hscB(yfhE) (SEQ ID NO. 42).

In another embodiment, a mutated gene selected from one of SEQ ID NOs: 35–42 is engineered into a carotenoid producing microorganism (one naturally possessing the isoprenoid/carotenoid pathway or one that had the pathway engineered by recombinant technology) to increase carotenoid production. In a preferred embodiment, two or more of the mutant genes are incorporated into a carotenoid producing microorganism to optimize carotenoid production. In a more preferred embodiment, the carotenoid producing microorganism is a recombinantly modified *E. coli* strain.

Several strains of *E. coli* capable of increased carotenoid production have been created. Mutations to genes not considered part of either the isoprenoid or carotenoid biosynthetic pathways were created, mapped, and sequenced. These novel mutant sequences can be used alone or in combination with others to create strains of *E. coli* exhibiting enhanced carotenoid production.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

GENERAL METHODS

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes, and materials used for the growth and maintenance of bacterial cells were obtained from Aldrich Chemicals (Milwaukee, Wiss.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wiss.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "μL" mean microliters, "mL" means milliliters, and "L" means liters.

Example 1

Cloning of β-Carotene Production Genes from *Pantoea stewartii*

Primers were designed using the sequence from *Erwinia uredovora* to amplify a fragment by PCR containing the crt genes. These sequences included 5'-3':

| | |
|---|---|
| ATGACGGTCTGCGCAAAAAAACACG | SEQ ID 13 |
| GAGAAATTATGTTGTGGATTTGGAATGC | SEQ ID 14 |

Chromosomal DNA was purified from *Pantoea stewartii* (ATCC no. 8199) and Pfu Turbo polymerase (Stratagene, La Jolla, Calif.) was used in a PCR amplifcation reaction under the following conditions: 94° C., 5 min; 94° C. (1 min)-60° C. (1 min)-72° C. (10 min) for 25 cycles, and 72° C. for 10 min. A single product of approximately 6.5 kb was observed following gel electrophoresis. Taq polymerase (Perkin Elmer, Foster City, Calif.) was used in a ten minute 72° C. reaction to add additional 3' adenosine nucleotides to the fragment for TOPO cloning into pCR4-TOPO (Invitrogen, Carlsbad, Calif.) to create the plasmid pPCB13. Following transformation to *E. coli* DH5α (Life Technologies, Rockville, Md.) by electroporation, several colonies appeared to be bright yellow in color indicating that they were producing a carotenoid compound. Following plasmid isolation as instructed by the manufacturer using the Qiagen (Valencia, Calif.) miniprep kit, the plasmid containing the 6.5 kb amplified fragment was transposed with pGPS1.1 using the GPS-1 Genome Priming System kit (New England Biolabs, Inc., Beverly, Mass.). A number of these transposed plasmids were sequenced from each end of the transposon. Sequence was generated on an ABI Automatic sequencer using dye terminator technology (U.S. Pat. No. 5,366,860, EP 272007) using transposon specific primers. Sequence assembly was performed with the Sequencher program (Gene Codes Corp., Ann Arbor, Mich.).

Example 2

Identification and Characterization of *Pantoea stewartii* Genes

Genes encoding crtE, X, Y, I, B, and Z cloned from *Pantoea stewartii* were identified by conducting BLAST (Basic Local Alignment Search Tool; Altschul, S. F., et al., *J. Mol. Biol.* 215:403–410 (1993)) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequences obtained were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J., *Nature Genetics*, 3:266–272 (1993)) provided by the NCBI.

All comparisons were done using either the BLASTNnr or BLASTXnr algorithm. The results of the BLAST comparison is given in Table 4 which summarize the sequences to which they have the most similarity. Table 4 displays data based on the BLASTXnr algorithm with values reported in expect values. The Expect value estimates the statistical significance of the match, specifying the number of matches, with a given score, that are expected in a search of a database of this size absolutely by chance.

TABLE 4

| ORF Name | Gene Name | Similarity Identified | SEQ ID base | SEQ ID Peptide | % Identity[a] | % Similarity[b] | E-value[c] | Citation |
|---|---|---|---|---|---|---|---|---|
| 1 | crtE | Geranylgeranyl pryophosphate synthetase (or GGPP synthetase, or farnesyltranstransferase) EC 2.5.1.29 gi\|117509\|sp\|P21684\|CRTE_PANAN GERANYLGERANYL PYROPHOSPHATE SYNTHETASE (GGPP SYNTHETASE) (FARNESYLTRANSFERASE) | 1 | 2 | 83 | 88 | e−137 | Misawa et al., J. Bacteriol. 172 (12), 6704–6712 (1990) |
| 2 | crtX | Zeaxanthin glucosyl transferase EC 2.4.1.— gi\|1073294\|pir\|\|S52583 crtX protein - *Erwinia herbicola* | 3 | 4 | 75 | 79 | 0.0 | Lin et al., Mol. Gen. Genet. 245 (4), 417–423 (1994) |
| 3 | crtY | Lycopene cyclase gi\|1073295\|pir\|\|S52585 lycopene cyclase - *Erwinia herbicola* | 5 | 6 | 83 | 91 | 0.0 | Lin et al., Mol. Gen. Genet. 245 (4), 417–423 (1994) |
| 4 | crtI | Phytoene desaturaseEC 1.3.—.— gi\|1073299\|pir\|\|S52586 phytoene dehydrogenase (EC 1.3.—.—) - *Erwinia herbicola* | 7 | 8 | 89 | 91 | 0.0 | Lin et al., Mol. Gen. Genet. 245 (4), 417–423 (1994) |
| 5 | crtB | Phytoene synthaseEC2.5.1.— gi\|1073300\|pir\|\|S52587 prephytoene pyrophosphate synthase - *Erwinia herbicola* | 9 | 10 | 88 | 92 | e−150 | Lin et al., Mol. Gen. Genet. 245 (4), 417–423 (1994) |
| 6 | crtZ | Beta-carotene hydroxylase gi\|117526\|sp\|P21688\|CRTZ_PANAN BETA-CAROTENE HYDROXYLASE HYDROXYLASE | 11 | 12 | 88 | 91 | 3e−88 | Misawa et al., J. Bacteriol. 172 (12), 6704–6712 (1990) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, thatare expected in a search of a database of this size absolutely by chance.

Example 3

Isolation of Chromosomal Mutations that Increase Carotenoid Production

Wild type *E. coli* is non-carotenogenic and synthesizes only the farnesyl pyrophosphate precursor for carotenoids. When the crtEXYIB gene cluster from *Pantoea stewartii* was introduced into *E. coli*, β-carotene was synthesized and the cells exhibit a yellow color characteristic of β-carotene. *E. coli* chromosomal mutations which increase carotenoid production should result in colonies that are more intensely pigmented or show deeper yellow in color (FIG. 2).

The plasmid pPCB15 (cam$^R$)(SEQ ID NO. 43) encodes the carotenoid biosynthesis gene cluster (crtEXYIB) from *Pantoea Stewartii* (ATCC no. 8199). The pPCB15 plasmid was constructed from ligation of SmaI digested pSU18 (Bartolome et al., *Gene*, 102:75–78 (1991)) vector with a blunt-ended PmeI/NotI fragment carrying crtEXYIB from pPCB13 (Example 1). *E. coli* MG1655 transformed with pPCB15 was used for transposon mutagenesis. Mutagenesis was performed using EZ:TN™ <KAN-2> Tnp Transposome™ kit (Epicentre Technologies, Madison, Wiss.) according to manufacture's instructions. A 1 µL volume of the transposome was electroporated into 50 µL of highly electro-competent MG1655(pPCB15) cells. The mutant cells were spread onto LB-Noble Agar (Difco laboratories, Detroit, Mich.) plates with 25 µg/mL kanamycin and 25 µg/mL chloramphenicol, and grown at 37° C. overnight. Tens of thousands of mutant colonies were visually examined for production of increased levels of β-carotene as evaluated by deeper yellow color development. The candidate mutants were re-streaked to fresh LB-Noble agar plates and glycerol frozen stocks made for further characterization.

Example 4

Quantitation of Carotenoid Production

To confirm that the mutants selected for increased production β-carotene by visually screening for deeper yellow colonies in Example 3 indeed produced more β-carotene, the carotenoids were extracted from cultures grown from each mutant strain and quantified spectrophotometrically. Each candidate mutant strain was cultured in 10 mL LB medium with 25 µg/mL chloramphenicol in 50 mL flasks overnight shaking at 250 rpm. MG1655(pPCB15) was used as the control. Carotenoids were extracted from each cell pellet for 15 min into 1 mL acetone, and the amount of β-carotene produced was measured at 455 nm. Cell density was measured at 600 nm. The ratio OD455/OD600 was used to normalize β-carotene production for different cultures. β-carotene production was also verified by HPLC. Among all the mutant clones tested, eight showed increased β-carotene production. The averages of three independent measurements with standard deviations were calculated and are indicated in FIG. 3. Mutants Y1, Y8 and Y12 showed 2.5–3.5 fold increase in production of β-carotene. Mutants Y4, Y15, Y16, Y17 and Y21 showed 1.5–2 fold increase in production of β-carotene.

Example 5

Mapping of the Transposon Insertions on the *E. coli* Chromosome

The transposon insertion site in each mutant was identified by PCR and sequencing directly from chromosomal DNA of the mutant strains. A modified single-primer PCR method (Karlyshev et al., *BioTechniques*, 28:1078-82, 2000) was used. For this method, a 100 µL volume of overnight culture was heated at 99° C. for 10 min in a PCR machine. Cell debris was removed by centrifugation at 4000 g for 10 min. A 1 µL volume of supernatant was used in a 50 µL PCR reaction using either Tn5PCRF (5'-GCTGAGTTGAAG-GATCAGATC-3';SEQ ID NO:15) or Tn5PCRR (5'-CGAG-CAAGACGTTTCCCGTTG-3';SEQ ID NO:16) primer. PCR was carried out as follows: 5 min at 95° C.; 20 cycles of 92° C. for 30 sec, 60° C. for 30 sec, 72° C. for 3 min; 30 cycles of 92° C. for 30 sec, 40° C. for 30 sec, 72° C. for 2 min; 30 cycles of 92° C. for 30 sec, 60° C. for 30 sec, 72° C. for 2 min. A 10 µL volume of each PCR product was electrophoresed on an agarose gel to evaluate product length. A 40 µL volume of each PCR product was purified using the Qiagen PCR cleanup kit, and sequenced using sequencing primers Kan-2 FP-1 (5'-ACCTACAA-CAAAGCTCTCATCAACC-3';SEQ ID NO:17) or Kan-2 RP-1 (5'-GCAATGTAACATCAGAGATTTTGAG-3';SEQ ID NO:18) provided by the EZ:TN™ <KAN-2> Tnp Transposome™ kit. The chromosomal insertion site of the transposon was identified as the junction between the Tn5 transposon and MG1655 chromosome DNA by aligning the sequence obtained from each mutant with the *E. coli* genomic sequence of MG1655 (GenBank® Accession number U00096). Table 5 summarizes the chromosomal insertion sites of the mutants that showed increased carotenoid production. The numbers refer to the standard base pair (bp) numbers in the *E. coli* genome. The majority of the harboring transposons are involved in transcription, translation or RNA stability. Five of the insertion sites (thrS, rpsA, rpoC, yjeR, and rhoL) were previously reported to be essential for viability of the *E. coli* cell. The transposon insertions we obtained in these five genes (thrS, rpsA, rpoC, yjeR, and rhoL) were located very close to the carboxyl terminal end of the gene and most likely resulted in functional although truncated proteins. The genes affected in another set of five mutants (thrS, rpoC, mreC, rhoL, and hscB) were part of demonstrated or predicted operons. FIG. 4 shows the neighborhood organization of the genes containing the transposon insertions.

TABLE 5

Localization of the transposon insertions in *E. coli* chromosome

| Mutant | Transposon insertion Site | Gene disrupted | Function | Operon | Essential gene | Reference |
|--------|---------------------------|----------------|----------|--------|----------------|-----------|
| Y1 | 1798679 | thrS: 1798666–1800594 | threonyl-tRNA synthetase | thrS-infC-rpmI-rplT | Yes | Johnson EJ, 1977 J Bacteriol 129: 66–70 |
| Y4 | 3304788 | deaD: 3303612–3305552 | RNA helicase | | No | Toone WM, 1991 J Bacteriol 173: 3291–302 |
| Y8 | 962815 | rpsA: 961218–962891 | 30 S ribosomal subunit protein S1 | | Yes | Kitakawa M, 1982 Mol Gen Genet 185: 445–7 |

TABLE 5-continued

Localization of the transposon insertions in *E. coli* chromosome

| Mutant | Transposon insertion Site | Gene disrupted | Function | Operon | Essential gene | Reference |
|---|---|---|---|---|---|---|
| Y12 | 4187062 | rpoC: 4182928–4187151 | RNA polymerase β' subunit | rpoB-rpoC | Yes | Post, L.E, 1979 Proc Natl Acad Sci USA. 76: 1697–1701 |
| Y15 | 4389704 | yjeR: 4389113–4389727 | oligo-ribonuclease | | Yes | Ghosh S, 1999 Proc Natl Acad Sci USA. 96: 4372–7. |
| Y16 | 3396592 | mreC: 3396512–3397615 | rod shape-determining protein | mreB-mreC-mreD | No | Wachi M, 1987 J Bacteriol 169: 4935–40 |
| Y17 | 3963892 | rhoL: 3963846–3963947 | rho operon leader peptide | rhoL-rho | Yes | Das A, 1976 Proc Natl Acad Sci USA. 73: 1959–63 |
| Y21 | 2657233 | yfhE (hscB): 2656972–2657487 | heat shock cognate protein | hscB-hscA-fdx-yfhJ | Unknown | Takahashi Y, 1999 J Biochem (Tokyo) 126: 917–26 |

Example 6

Confirmation of Transposon Insertions in *E. coli* Chromosome

To confirm the transposon insertion sites in Example 5, chromosome specific primers were designed 400–800 bp upstream and downstream from the transposon insertion site for each mutant. The list of the primer sequences is summarized in Table 6. Three sets of PCR reactions were performed for each mutant. The first set (named as PCR 1) uses a chromosome specific upstream primer paired with a chromosome specific downstream primer. The second set (PCR 2) uses a chromosome specific upstream primer paired with a transposon specific primer (either Kan-2 FP-1 or Kan-2 RP-1, depending on the orientation of the transposon in the chromosome). The third set (PCR 3) uses a chromosome specific downstream primer paired with a transposon specific primer. PCR conditions are: 5 min at 95° C.; 30 cycles of 92° C. for 30 sec, 55° C. for 30 sec, 72° C. for 1 min; then 5 min at 72° C. Wild type MG1655(pPCB15) cells served as control cells. For the control cells, the expected wild type bands were detected in PCR1, and no mutant band was detected in PCR2 or PCR3. For all the eight mutants, no wild type bands were detected in PCR1, and the expected mutant bands were detected in both PCR2 and PCR3. The size of the products in PCR2 and PCR3 correlated well with the insertion sites in each specific gene. Therefore, the mutants contained the transposon insertions as mapped in Table 5. They were most likely responsible for the phenotype of increased carotenoid production in each of the mutants.

TABLE 6

List of chromosome specific primers used for mutant confirmation

| Primer | Sequence | SEQ ID NO |
|---|---|---|
| Y1_F | 5'-agcaccatgatcatctggcg-3' | 19 |
| Y1_R | 5'-cggttgcgctggaagaaaac-3' | 20 |
| Y4_F | 5'-caccctgtgccattttcagc-3' | 21 |
| Y4_R | 5'-cgttctgggtatggcccaga-3' | 22 |
| Y8_1_F | 5'-aaagctaacccgtggcagca-3' | 23 |
| Y8_1_R | 5'-tttgcgttccccgaggcata-3' | 24 |
| Y12_F | 5'-ttccgaaatggcgtcagctc-3' | 25 |
| Y12_R | 5'-atctctacattgattatgagtattc-3' | 26 |
| Y15_F | 5'-ggatcgatcttgagatgacc-3' | 27 |
| Y15_R | 5'-gctttcgtaattttcgcatttctg-3' | 28 |
| Y16_F | 5'-cacgccaagttgcgcaagta-3' | 29 |
| Y16_R | 5'-gcagaaaatggtgactcagg-3' | 30 |
| Y17_F | 5'-ggcgatcctcgtcgatttct-3' | 31 |
| Y17_R | 5'-acgcagacgagagtttgcgt-3' | 32 |
| Y21_F | 5'-accgaatgcccttgctgttg-3' | 33 |
| Y21_R | 5'-gggtgttcaggtatggctta-3' | 34 |

What is claimed is:

1. A carotenoid overproducing *E. coli* comprising the genes encoding a functional isoprenoid enzymatic biosynthetic pathway comprising a deaD disrupted gene.

2. The carotenoid overproducing *E. coli* of claim 1 wherein the isoprenoid enzymatic biosynthetic pathway comprises:
   a) an upper isoprenoid enzymatic biosynthetic pathway comprising the genes dxs, dxr, ygbP, ychB, ygbB, lytB, idi, ispA, and ispB; and
   b) a lower isoprenoid enzymatic biosynthetic pathway comprising the genes crtE, crtB, cdl, and crtY.

3. The carotenoid overproducing *E. coli* of claim 2 wherein the lower pathway optionally comprises genes selected from the group consisting of crtZ and crtW.

4. The carotenoid overproducing *E. coli* of either of claims 2 or 3 wherein the lower pathway genes reside on an autonomously replicating plasmid.

5. The carotenoid overproducing *E. coli* of claim 4 wherein the autonomously replicating plasmid comprises a replicon selected from the group consisting of p15A and pMB1.

6. The carotenoid overproducing *E. coli* of either of claims 2 or 3 wherein the lower pathway genes are chromosomally integrated.

7. A carotenoid overproducing *E. coli* according to claim 1 wherein the disrupted deaD gene has the sequence as set forth in SEQ ID NO:36.

8. A method for the production of a carotenoid comprising:
   a) contacting the carotenoid overproducing *E. coli* of any of claims 1–3 with a fermentable carbon substrate;
   b) growing the carotenoid overproducing *E. coli* of step (a) for a time sufficient to produce a carotenoid; and
   c) optionally recovering the carotenoid form the carotenoid overproducing *E. coli* of step (b).

9. A method according to claim 8 wherein the carotenoid is selected from the group consisting of antheraxanthin, adonixanthin, astaxanthin, canthaxanthin, capsorubrin, β-cryptoxanthin, didehydrolycopene, didehydrolycopene, β-carotene, ζ-carotene, δ-carotene, γ-carotene, keto-γ-carotene, ψ-carotene, ε-carotene, β,ψ-carotene, torulene, echinenone, alpha-cryptoxanthin, diatoxanthin, 7,8-didehydroastaxanthin, fucoxanthin, fucoxanthinol, isorenieratene, β-isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, zeaxanthin, and C30-carotenoids.

* * * * *